(12) United States Patent
Nilsson et al.

(10) Patent No.: US 7,915,300 B2
(45) Date of Patent: Mar. 29, 2011

(54) CYSTEINE PROTEASE INHIBITORS

(75) Inventors: Magnus Nilsson, Huddinge (SE);
Xiao-Xiong Zhou, Huddinge (SE);
Lourdes Oden, Huddinge (SE); Bjorn Classon, Huddinge (SE); Rolf Noren, Huddinge (SE); Urszula Grabowska, Little Chesterford (GB); Philip Jackson, Little Chesterford (GB); Philip Fallon, Little Chesterford (GB); Andrew Carr, Little Chesterford (GB); Mark Liley, Little Chesterford (GB); Matt Tozer, Essex (GB); Tony Johnson, Essex (GB); Victor Diaz, Essex (GB); Laia Crespo, Essex (GB); Jussi Kangasmetsa, Essex (GB); Thierry Bonnaud, Essex (GB)

(73) Assignee: Medivir AB, Huddinge (SE)

( * ) Notice: Subject to any disclaimer, the term of this patent is extended or adjusted under 35 U.S.C. 154(b) by 659 days.

(21) Appl. No.: 10/584,930

(22) PCT Filed: Jan. 6, 2005

(86) PCT No.: PCT/GB2005/050003
§ 371 (c)(1),
(2), (4) Date: Mar. 31, 2008

(87) PCT Pub. No.: WO2005/066180
PCT Pub. Date: Jun. 21, 2005

(65) Prior Publication Data
US 2008/0234260 A1 Sep. 25, 2008

(30) Foreign Application Priority Data

Jan. 8, 2004 (SE) .................................. 0400022
May 26, 2004 (SE) .................................. 0401332

(51) Int. Cl.
*A61K 31/407* (2006.01)
*A61K 31/34* (2006.01)
*C07D 487/04* (2006.01)
*C07D 307/00* (2006.01)

(52) U.S. Cl. ........ 514/412; 514/421; 514/469; 514/470; 548/453; 549/465

(58) Field of Classification Search .................. 514/412, 514/421, 469, 470; 548/453; 549/465
See application file for complete search history.

(56) References Cited

FOREIGN PATENT DOCUMENTS

| WO | 98/50533 | 11/1998 |
| WO | WO 98/50533 | 11/1998 |
| WO | WO 01/58886 A1 | 8/2001 |
| WO | 02/057270 | 7/2002 |
| WO | WO 02/057270 | 7/2002 |
| WO | WO 02057270 A1 * | 7/2002 |
| WO | 02/088106 | 11/2002 |
| WO | WO 02/088106 | 11/2002 |
| WO | WO 2005/056529 A1 | 6/2005 |
| WO | WO 2005/065578 A2 | 7/2005 |
| WO | WO 2005/066159 A1 | 7/2005 |
| WO | WO 2005/066180 A1 | 7/2005 |
| WO | WO 2007/006716 A1 | 1/2007 |
| WO | WO 2008/007127 A1 | 1/2008 |

OTHER PUBLICATIONS

Preliminary STN search_10584930_02262010.*
Wu and Farrelly, Toxicology 236:1-6, 2007.*
Third Party Observations filed on behalf of Amura Therapeutics Limited, Jan. 5, 2009.
Applicant's Response to Examination Report in Corresponding European Application, Mar. 2, 2009.
Applicants Cover Letter, Jun. 29, 2007, in European Opposition.
Applicants Cover Letter, Jan. 14, 2008, in European Opposition.
Clyde-Watson et al., Third Party Observations filed on behalf of Amura Therapeutics Limited . . . , Sep. 3, 2007, EPO—Munich.
Teuten et al., Applicant Medivir AB, D4—Supplementary Experimental Data, Jun. 29, 2007, EPO—Munich.

(Continued)

*Primary Examiner* — Yong Chu
(74) *Attorney, Agent, or Firm* — Birch, Stewart, Kolasch and Birch, LLP

(57) ABSTRACT

A compound of the formula II

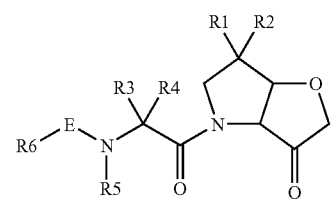

wherein
one of $R^1$ and $R^2$ is halo and the other is H or halo;
$R^3$ is $C_1$-$C_4$ straight or branched chain, optionally fluorinated, alkyl;
$R^4$ is H; or
$R^3$ together with $R^4$ and the adjoining backbone carbon defines:
a spiro-$C_5$-$C_7$ cycloalkyl, optionally substituted with 1 to 3 substituents selected from halo, hydroxyl, $C_1$-$C_4$ alkyl or $C_1$-$C_4$ haloalkyl; or optionally bridged with a methylene group; or
a $C_4$-$C_6$ saturated heterocycle having a hetero atom selected from O, NRa, S, S(=O)$_2$; where Ra is H, $C_1$-$C_4$ alkyl or $CH_3C$(=O);
$R^5$ is independently selected from H or methyl;
E is —C(=O)—, —S(=O)$_m$—, —NR$^5$S(=O)$_m$—, —NR$^5$C(=O)—, —OC(=O)—,
$R^6$ is a stable, optionally substituted, monocyclic or bicyclic, carbocycle or heterocycle;
m is independently 0,1 or 2;
are inhibitors of cathepsin K and useful in the treatment or prophylaxis of osteoporosis.

29 Claims, No Drawings

OTHER PUBLICATIONS

Wolfe et al., Scope and Limitations of the Pd/BINAP-Catalyzed Amination of Aryl Bromides, J. Org. Chem, 2000, vol. 65, pp. 1144-1157.

Watts, et al., "Functionalised 2,3-dimethyl-3-aminotetrahydrofuran-4-one and N-(3-oxo-hexahydrocyclcopenta[b]furan-3a-yl)acylamide based scaffolds: synthesis and cysteinyl proteinase inhibition", Bioorganic and Medicinal Chemistry, 2004 12:2903-2925.

Quibell, "Bicyclic peptidomimetic tetrahydrofuro[3,2-b]pyrrol-3-one and hexahydrofuro[3,2-b]pyridine-3-one based scaffolds: synthesis and cysteinyl proteinase inhibition", Bioorganic and Medicinal Chemistry, 2004 12:5689-5710.

International Search Report (Form PCT/ISA/210), 2006.

Written Opinion of the Searching Authority (Form PCT/ISA/237), 2006.

* cited by examiner

US 7,915,300 B2

CYSTEINE PROTEASE INHIBITORS

This application is the national stage of International Application No. PCT/GB05/50003 filed on Jan. 6, 2005, which claims priority under 35 USC §119 (a)-(d) of Application No. 0400022-0 filed in Sweden on Jan. 8, 2004 and Application No. 0401332-2 filed in Sweden on May 26, 2004.

FIELD OF THE INVENTION

This invention relates to inhibitors of cysteine proteases, especially those of the papain superfamily. The invention provides novel compounds useful in the prophylaxis or treatment of disorders stemming from misbalance of physiological proteases such as cathepsin K.

DESCRIPTION OF RELATED ART

The papain superfamily of cysteine proteases is widely distributed in diverse species including mammals, invertebrates, protozoa, plants and bacteria. A number of mammalian cathepsin enzymes, including cathepsins B, F, H, K, L, O and S, have been ascribed to this superfamily, and inappropriate regulation of their activity has been implicated in a number of metabolic disorders including arthritis, muscular dystrophy, inflammation, glomerulonephritis and tumour invasion. Pathogenic cathepsin like enzymes include the bacterial gingipains, the malarial falcipains I, II, III et seq and cysteine proteases from *Pneumocystis carinii*, *Trypanosoma cruzei* and *brucei*, *Crithidia fusiculata*, *Schistosoma* spp.

The inappropriate regulation of cathepsin K has been implicated in a number of disorders including osteoporosis, gingival diseases such as gingivitis and periodontitis, Paget's disease, hypercalcaemia of malignancy and metabolic bone disease. In view of its elevated levels in chondroclasts of osteoarthritic synovium, cathepsin K is implicated in diseases characterised by excessive cartilege or matrix degradation, such as osteoarthritis and rheumatoid arthritis. Metastatic neoplastic cells typically express high levels of proteolytic enzymes that degrade the surrounding matrix and inhibition of cathepsin K may thus assist in treating neoplasias.

International patent application no WO02057270 discloses compounds of the formula I

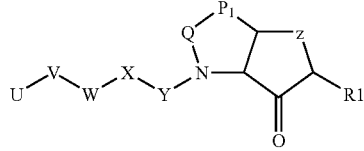

where UVWXY broadly corresponds to the P3 and P2 of dipeptide cysteine protease inhibitors, Z is inter alia O, S, methylene or —NR—, $R^1$ is alkyl, alkylaryl etc and P1 and Q1 are each methylene, optionally substituted with various carbon chains and cyclic groups. The compounds are alleged to be useful for the treatment of protozoal infections such as trypanosomes.

We have now discovered that introduction of a halogen atom at a particular ring position produces an increase in potency against cathepsin K.

BRIEF DESCRIPTION OF THE INVENTION

In accordance with the invention, there is provided compounds of the formula II:

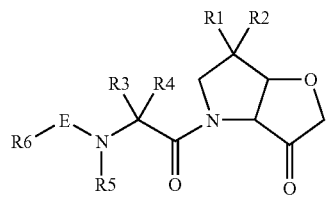

wherein
one of $R^1$ and $R^2$ is halo and the other is H or halo;
$R^3$ is $C_1$-$C_5$ straight or branched chain, optionally fluorinated, alkyl;
$R^4$ is H; or
$R^3$ together with $R^4$ and the adjacent backbone carbon atom defines
a spiro-$C_5$-$C_7$ cycloalkyl, optionally substituted with 1 to 3 substituents selected from halo, hydroxyl, $C_1$-$C_4$ alkyl or $C_1$-$C_4$ haloalkyl; or optionally bridged with a methylene group; or
a $C_4C_6$ saturated heterocycle having a hetero atom selected from O, NRa, S, S(=O)$_2$; where Ra is H, $C_1$-$C_4$ alkyl or $CH_3C$(=O);
$R^5$ is independently selected from H or methyl;
E is —(=O)—, —S(=O)$_m$—, —NR$^5$S(=O)$_m$, —NR$^5$C(=O)—, —OC(=O)—;
$R^6$ is a stable, optionally substituted, monocyclic or bicyclic, carbocycle or heterocycle wherein the or each ring has 4, 5 or 6 ring atoms and 0 to 3 hetero atoms selected from S, O and N and wherein the optional substituents comprise 1 to 3 members selected from $R_7$;
$R^7$ is independently selected from halo, oxo, nitrile, nitro, $C_1$-$C_4$ alkyl, —NRaRb, —XNRbR$^9$, —NRbC$_1$-$C_4$alkylR$^9$, NH2CO—, X—R$^9$, X—O—R$^9$, O—X—R9, X—C(=O)R$^9$, X—(C=O)NRaR$^9$, X—NRbC(=O)R$^9$, X—NHSO$_m$R$^9$, X—S(=O)$_m$R$^9$, X—C(=O)OR$^9$, X—NRbC(=O)OR$^9$;
$R^9$ is independently H, $C_1$-$C_4$ alkyl, $C_3$-$C_6$ cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, phenyl, any of which is optionally substituted with $R_{10}$;
$R_{10}$ is independently selected from hydroxy, —X—R$^9$, —XNRaRb, —XNRbR$^9$, —NRbC$_1$-$C_4$alkylR$^9$, nitro, cyano, carboxy, oxo, $C_1$-$C_4$ alkyl, $C_1$-$C_4$-alkoxy, $C_1$-$C_4$ alkanoyl, carbamoyl;
X is independently a bond or $C_1$-$C_4$ alkyl;
Rb is selected from H, $C_1$-$C_4$ alkyl
m is independently 0,1 or 2;
and pharmaceutically acceptable salts thereof.

Without in any way wishing to be bound by theory, or the ascription of tentative binding modes for specific variables, P1, P2 and P3 as used herein are provided for convenience only and have their conventional meanings and denote those portions of the inhibitor believed to fill the S1, S2 and S3 subsites respectively of the enzyme, where S1 is adjacent the cleavage site and S3 remote from the cleavage site.

Preferably the stereochemistry of the P1 group is as depicted in the partial structure below:

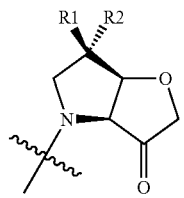

Preferably the halogen of R¹ and/or R² is chlorine and most preferably fluorine. It is currently preferred that $R^2$ is halo, especially fluorine and $R^1$ is H, but the invention extends to compounds wherein $R^1$ is halo, especially F and $R^2$ is H or $R^2$ and $R^2$ are each F.

It will be appreciated that the P1 group may exist in alternative forms, such as

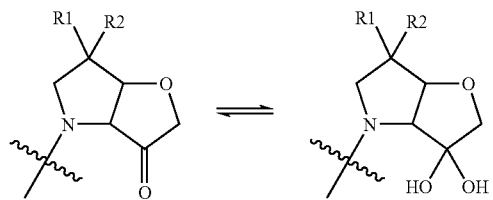

and the invention extends to all such alternative forms.

Preferably the stereochemistry of the P2 group corresponds to an L-amino acid as depicted in the partial structure below:

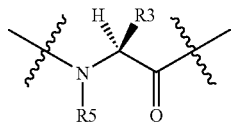

but the invention also extends to D-isomers.

The invention also includes all isomers and enantiomers at other chiral centres.

Currently preferred P2 groups include those wherein $R^4$ is H and wherein $R^3$ is iso-butyl. A further preferred P2 group is homo-t-butyl, that is —CH₂C(CH₃)₃

Alternative preferred P2 groups included those wherein $R^3$ and $R^4$ together define spirocycloalkyl, such as cyclopentyl, cycloheptyl and especially cyclohexyl.

If a P2 cycloalkyl is substituted, the substitution is typically para to the linkage to the backbone. Representative substituents include monofluoro, difluoro, monohydroxy, geminal hydroxyl & methyl substituents, monomethyl or geminal methyl.

Alternative P2 groups include those wherein $R^3$ and $R^4$ together define a 6 membered, saturated heterocycle, wherein a hetero atom selected from O, S, S(=O)₂ or NRx where X is H or methyl, situated at the position corresponding to para or meta to the point of attachment to the backbone.

Representative P2 groups in accordance with the two paragraphs immediately above include

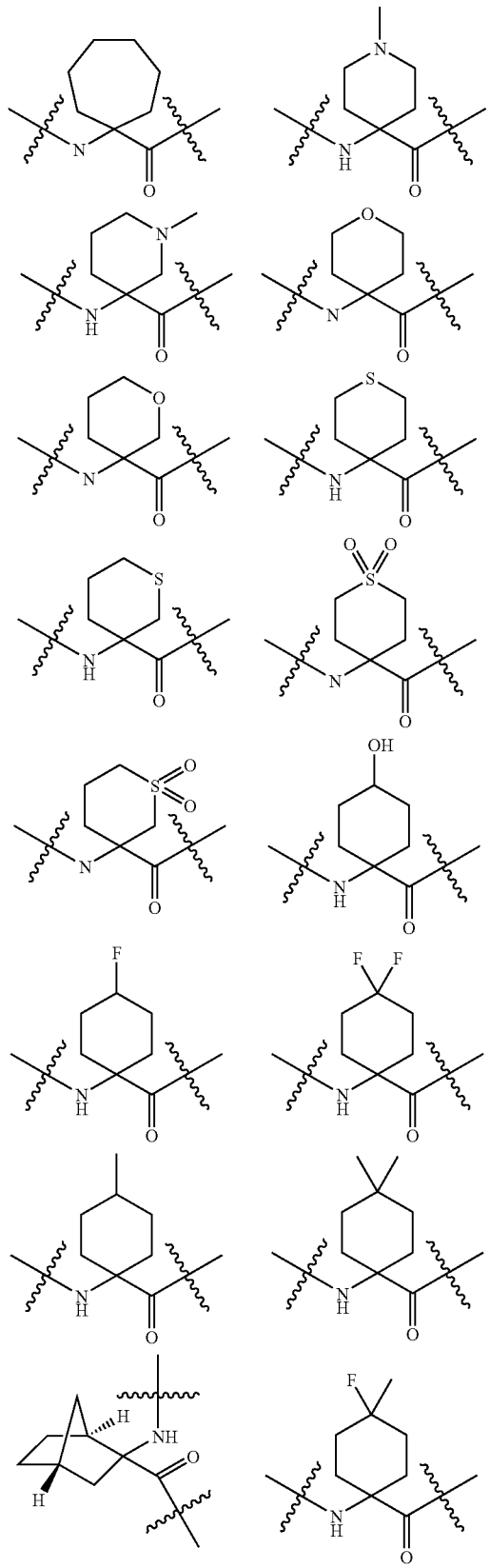

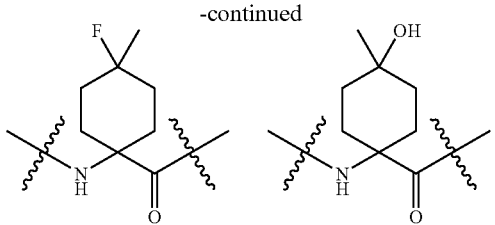

Currently preferred P2 groups include

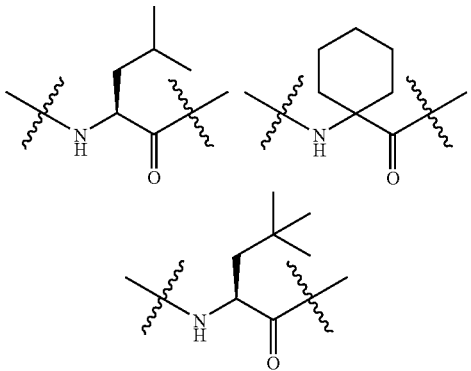

It is currently preferred that $R^5$ is H.

Preferred E groups include —S(=O)$_m$—, especially —S(=O)$_2$—, and most preferably —C(=O)—.

Typically $R^6$ is a monocyclic ring with 5 or especially 6 ring atoms, or a bicyclic ring structure comprising a 6 membered ring fused to a 4, 5 or 6 membered ring.

Typical $R^6$ groups include saturated or unsaturated heterocycles or saturated or unsaturated carbocycles, any of which are optionally substituted as described above. Illustrative variants include $C_{3-8}$ cycloalkyl, phenyl, benzyl, tetrahydronaphthyl, indenyl, indanyl, heterocyclyl such as from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, any of which may be substituted as described above.

The saturated heterocycle thus includes radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidinylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione, whereas the unsaturated heterocycle include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl. In each case the heterocycle may be condensed with a phenyl ring to form a bicyclic ring system.

Preferred monocyclic $R^6$ groups include substituted pyridyl, substituted pyrimidyl, substituted phenyl, particularly phenyl substituted with a cyclic group such as pyrrolidine-1-yl, piperidine-1-yl, 4-methylpiperidin-1-yl, 4-(piperidin-3-ylmethyl)-piperidin-1-yl, morpholin-4-yl, 4-methylpiperazin-1-yl, 2-morpholin-4-yl-ethylamino, 2-morpholin-4-yl-ethyloxy, 1-pyrid-2-ylmethylamino, piperazin-1-yl, piperid-4-yl or N-piperazinyl, N-substituted with Ra or piperidin-1-yl which is 4-substituted with —NRaRb. A phenyl $R^6$ is conveniently substituted at the 3 or 4 position (para or meta), for example with such a cyclic group.

Alternative cyclic substituents to a monocyclic $R^6$ (such as phenyl) include aryl groups such as phenyl or a 5 or 6 membered heteroaryl group such as thiophene, furyl, triazole, thiazole, diazole, pyrazole or pyrrolidine. Favoured cyclic substituents in this context include thiazol-2-yl, pyrid-3-yl and especially pyrid-2-yl, thien-2-yl or thiazol-5-yl. This cyclic substituent (ie $R^7$) is typically bonded direct to such $R^6$ species (ie X is a bond), but may also for example comprise an amine spacer such as —NH—, —N(Me), —CH$_2$NH, —CH$_2$N(Me)-, a $C_1$-$C_3$alkyl spacer such as —CH$_2$— or a $C_1$-$C_3$-alkyloxy spacer such as ethyloxy Any of the cyclic substituents to $R^6$ in the immediately preceding paragraph may be substituted as described above with $R^{10}$. For example a heterocycle $R^7$ group such as thiazolyl can be substituted with $C_1$-$C_4$ alkyl such as methyl.

Preferably, any of the cyclic substituents to $R^6$ in the two immediately preceding paragraphs may itself be substituted with a cyclic group (that is $R^7$ comprises an $R^9$ moiety) typically a saturated heterocyclic group such as piperidine, piperazine or morpholine, which saturated cyclic group is optionally substituted, for example with $C_1$-$C_3$ alkyl, fluoro, diflouro, $C_1$-$C_3$alkyloxy or $C_1$-$C_3$alkyloxy$C_1$-$C_3$alkyl. As provided in the definition of $R^7$, this saturated cyclic group (ie $R^9$) may be spaced from the $R^6$ group by X (eg $C_1$-$C_3$alkyl), amine (eg —NH—), amide, sulphonamide etc, but is typically bonded directly or via methylene.

Representative $R^9$ groups in accordance with the immediately preceding paragraph include heterocycles such as pyrrolidine-1-yl, piperidine-1-yl, 4-methylpiperidin-1-yl, 4-(piperidin-3-ylmethyl)piperidin-1-yl, morpholin-4-yl, 4-methylpiperazin-1-yl, 2-morpholin-4-yl-ethylamino, 2-morpholin-4-yl-ethyloxy, 1-pyrid-2-ylmethylamino, piperazin-1-yl, piperid-4-yl or N-piperazinyl, N-substituted with Ra or piperidin-1-yl which is 4-substituted with —NRaRb, Currently preferred $R^9$ substituents include 4-substituted piperazin-4-yl, such as 4-methyl-piperazin-4-yl or 4-methyloxyethyl-piperazin-4-yl, piperid-1-ylmethyl which is optionally 4-substituted with fluoro or diflouro or morpholinylmethyl.

Alternative preferred substituents to a monocyclic $R^6$ (such as phenyl) include —NRaRb, —CH$_2$NRaRb, $C_1$-$C_4$ straight or branched alkyl or —O—$R^9$.

Representative $R^6$ groups thus include:

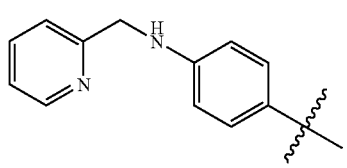

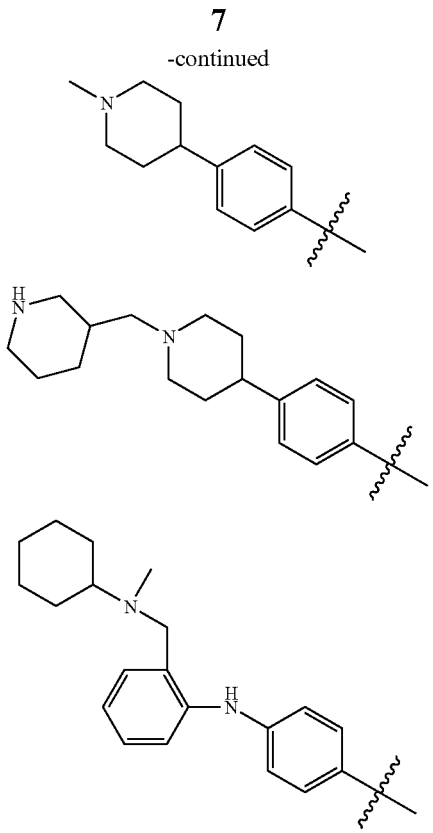

Further representative R[6] groups include

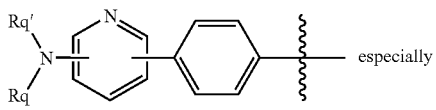 especially

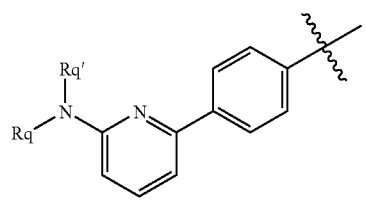

where Rq and Rq' are independently selected from H, $C_1$-$C_4$ alkyl or $C_1$-$C_4$alkanoyl or together define an unsaturated 5-7 membered ring, such as piperidine, piperazine or morpholine, which may in turn be substituted with groups corresponding to R[10], particularly $C_1$-$C_4$ alkyl, fluoro or difluoro.

Currently preferred R[6] groups include

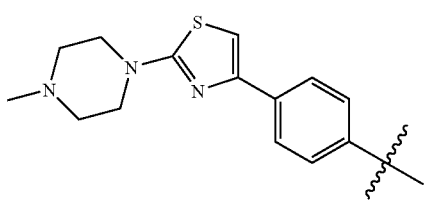

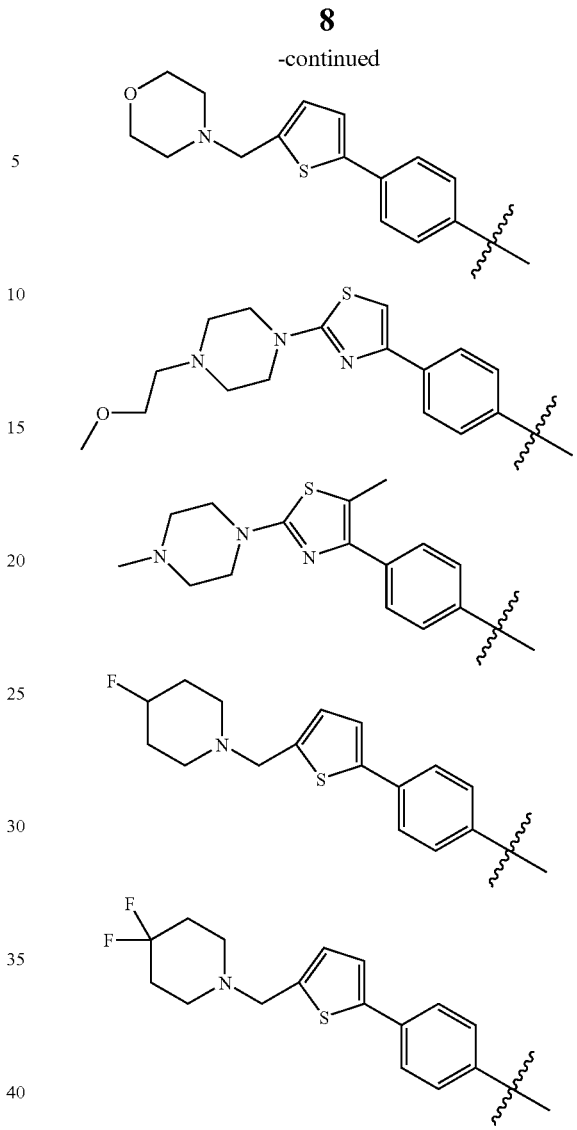

Representative bicyclic groups for R[6] include naphthyl-enyl, especially naphthylen-2-yl; benzo[1,3]dioxolyl, especially benzo[1,3]dioxol-5-yl, benzofuranyl, especially benzofuran-2-yl, and especially $C_1$-$C_6$ alkoxy substituted benzofuranyl, more especially 5-(2-piperazin-4-carboxylic acid tert-butyl ester-ethoxy)benzofuran-2-yl, 5-(2-morpholino-4-yl-ethoxy)-benzofuran-2-yl, 5-(2-piperazin-1-yl-ethoxy)benzofuran-2-yl, 5-(2-cyclohexyl-ethoxy)-benzofuran-2-yl; 7-methoxy-benzofuran-2-yl, 5-methoxy-benzofuran-2-yl, 5,6-dimethoxy-benzofuran-2-yl, especially halogen substituted benzofuranyl, more especially 5-fluoro-benzofuran-2-yl, 5,6-difluoro-benzofuran-2-yl, especially $C_1$-$C_6$alkyl substituted benzofuranyl, most especially 3-methyl-benzofuran-2-yl; benzo[b]thiophenyl, especially benzo[bithiophen-2-yl]; especially $C_1$-$C_6$alkoxy substituted benzo[b]thipheny], more especially 5,6-dimethoxy-benzo[b]thiophen-2-yl, quinolinyl, especially quinolin-2-yl, quinolin-3-yl, quinolinyl, quinolin-6-yl, and quinolin-S-yl; quinoxalinyl, especially quinoxalin-2-yl; 1,8-naphthyridinyl, especially 1,8-naphthyridin-2-yl; indolyl, especially indol-2-yl, especially indol-6-yl, indol-5-yl, especially $C_1$-$C_6$alkyl substituted indolyl, more especially N-methylindol-2-yl; furo[3,2-b]pyridinyl, especially furo[3,2-b]pyridin-2-yl, and $C_1$-$C_6$-alkyl substituted furo[3,2-b]pyridinyl, especially 3-methyl-furo[3,2-b]pyridin-2-yl; thieno[3,2-b]thiophene, especially thieno[3,2-b]thiophene-2-yl, more especially $C_1$-$C_6$alkyl substituted thieno[3,2-b]thiophene-2-yl, more especially 5-tert-buty]-3-methylthieno[3,2-b]thiophene-2-yl.

Favoured $R^6$ groups include bicyclic rings such as napthyl, quinoloyl, benzofuranyl, benzothienyl, indolyl and indolinyl, particularly where the linkage is to the 2 position of the ring. Favoured substituents to a bicyclic $R^6$ group include pyrrolidine-1-yl, piperidine-1-yl, 4-methylpiperidin-1-yl, 4-(piperidin-3-ylmethyl)-piperidin-1-yl, morpholin-4-yl, 4-methylpiperazin-1-yl, 2-morpholinyl-4-yl-ethylamino, 2-morpholin-4-yl-ethyloxy, 1-pyrid-2-ylmethylamino, piperazin-1-yl, piperid-4-yl or N-piperazinyl, N-substituted with Ra or piperidin-1-yl which is 4-substituted with —NRaRb. Especially preferred substituents, particularly in conjunction with benzofuranyl include 2-morpholin-4-yl-ethyloxy and N-methyl-piperidin-4-yloxy and those defined below.

A currently favoured bicyclic $R^6$ group is optionally substituted benzothiazol or benzofuryl or benzoxazolyl, including those wherein the substituent is —$OR^9$ or —$NRbR^9$. For example, favoured $R^6$ groups include benzofur-2-yl, unsubstituted or substituted in the 5 position with a saturated heterocycle such as piperidine, piperazine or morpholine, which is optionally substituted with $C_1$-$C_3$ alkyl and/or spaced from the benzofuryl by oxy, methyloxy or ethyloxy. Particularly favoured benzofuryl $R^6$ groups thus include:

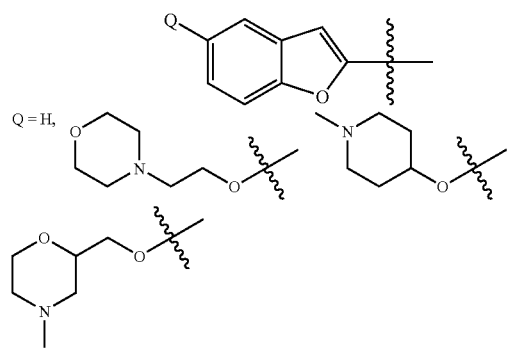

Returning to formula II in general:

X is typically methylene or especially a bond.

$C_1$-$C_n$ alkyl, where n is 4, on its own or within compound expressions such as $C_1$-$C_4$ alkoxy, includes methyl, ethyl, n-propyl, iso-propyl, n-butyl, iso-butyl, sec-butyl, t-butyl, cyclopropyl, methylcyclopropyl and the like, extended in a likewise fashion for other values of n. For example $C_5$ alkyl includes homo-t-butyl (—$CH_2C(CH_3)_3$).

Halogen or halo includes bromo, chloro and especially fluoro.

Haloalkyl means an alkyl group as defined above where at least one carbon atom bears 1 to 3 halogen atoms, preferably fluorine atoms. Representative haloalkyl group includes fluoromethyl, difluoromethyl, trifluoromethyl, 2, fluoroethyl, 2,2difluorethyl, 2,2,2trifluorethyl and the like.

The P1 building block employed in the present invention represent novel compounds and forms an additional aspect of the invention. Accordingly, this further aspect of the invention provides compounds of the formula

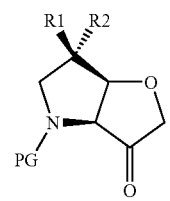

where R1 and R2 are as defined above and PG is a nitrogen protecting group as defined below, especially formyl, acetyl, benzoyl, pivaloyl, t-butylacetyl, phenylsulfonyl, benzyl, Fmoc, t-butoxycarbonyl (BOC) and benzyloxycarbonyl (Cbz). This aspect of the invention further includes the corresponding unprotected amines (ie PG=H).

The preferred embodiment of this aspect of the invention comprises compounds of the formula

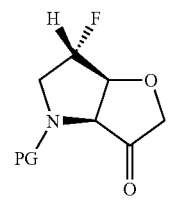

where PG is as described above.

The invention further embraces various novel P3 building blocks as illustrated in the examples below, as the acid or protected with a carboxy protecting group.

Favoured compounds of the invention include those permutations formed by independent selection of a P3, P2 and P1 member from each of Tables A, B and C:

TABLE A

P1 groups

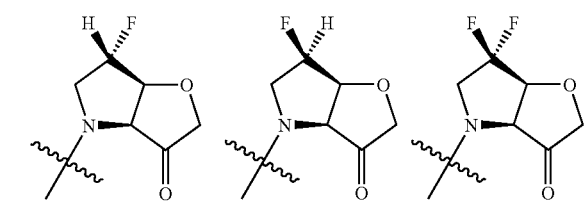

TABLE B

P2 groups

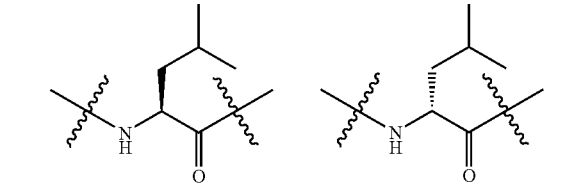

TABLE B-continued
P2 groups
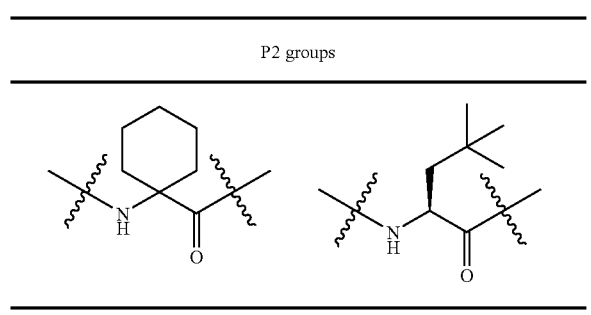
TABLE C
P3 groups
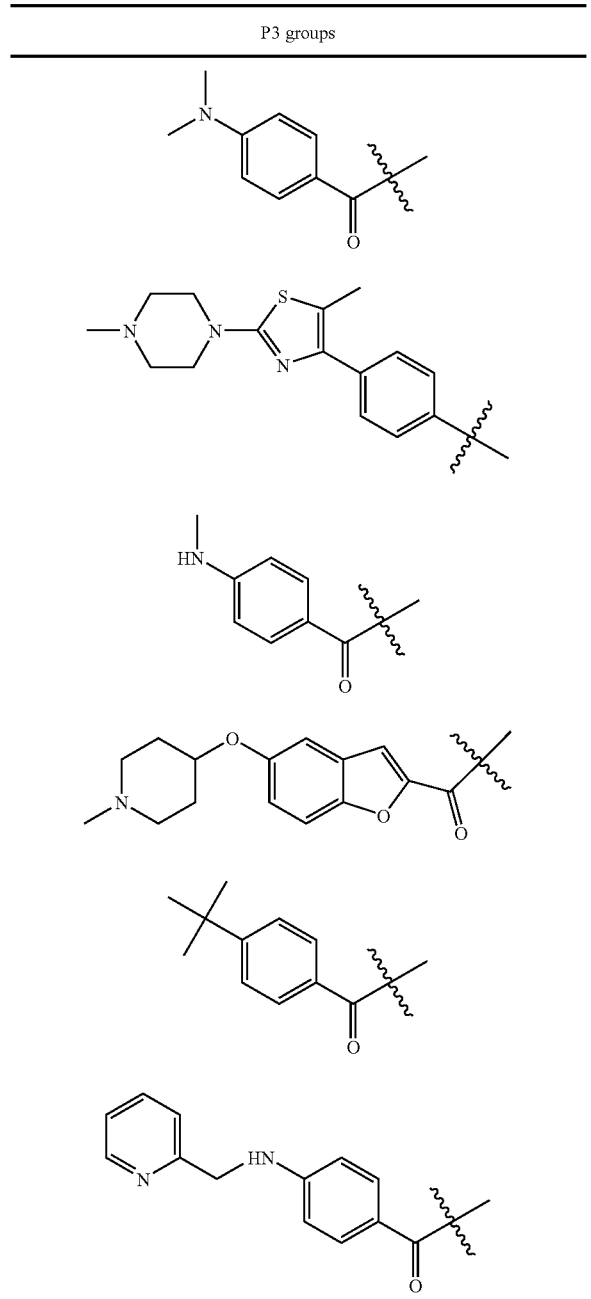
TABLE C-continued
P3 groups
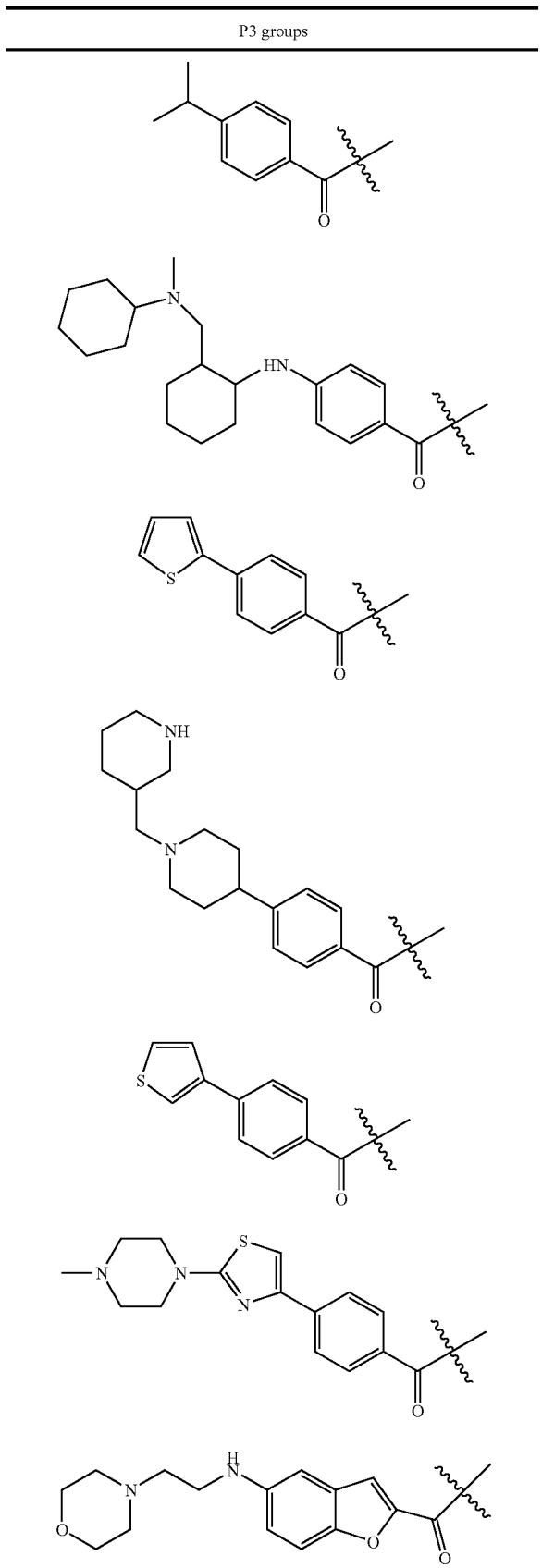

TABLE C-continued
P3 groups
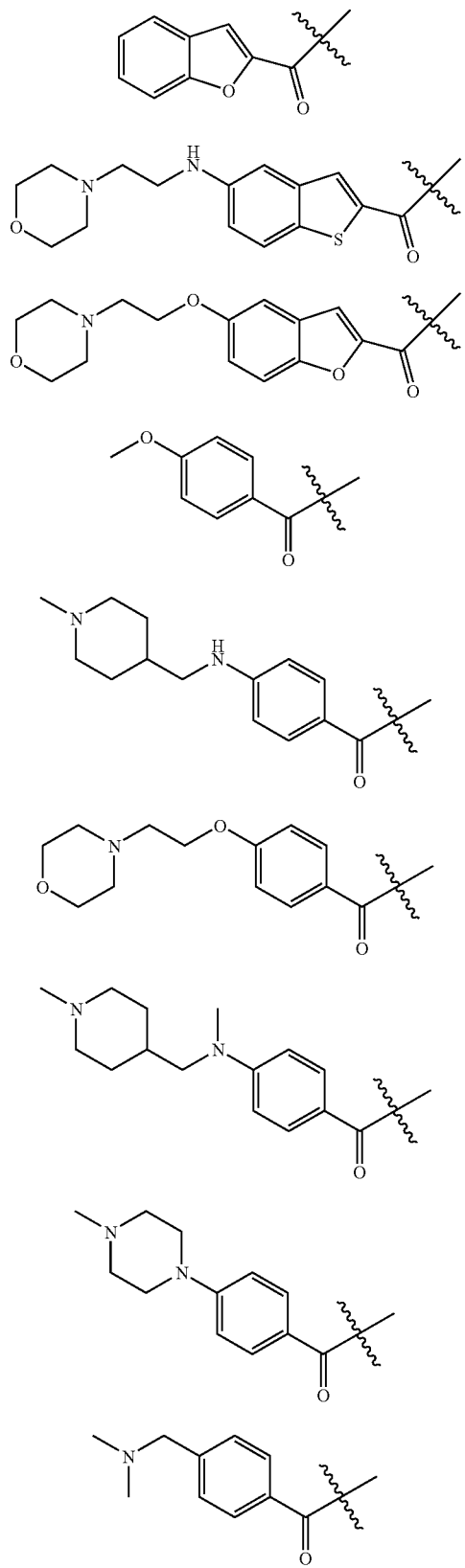
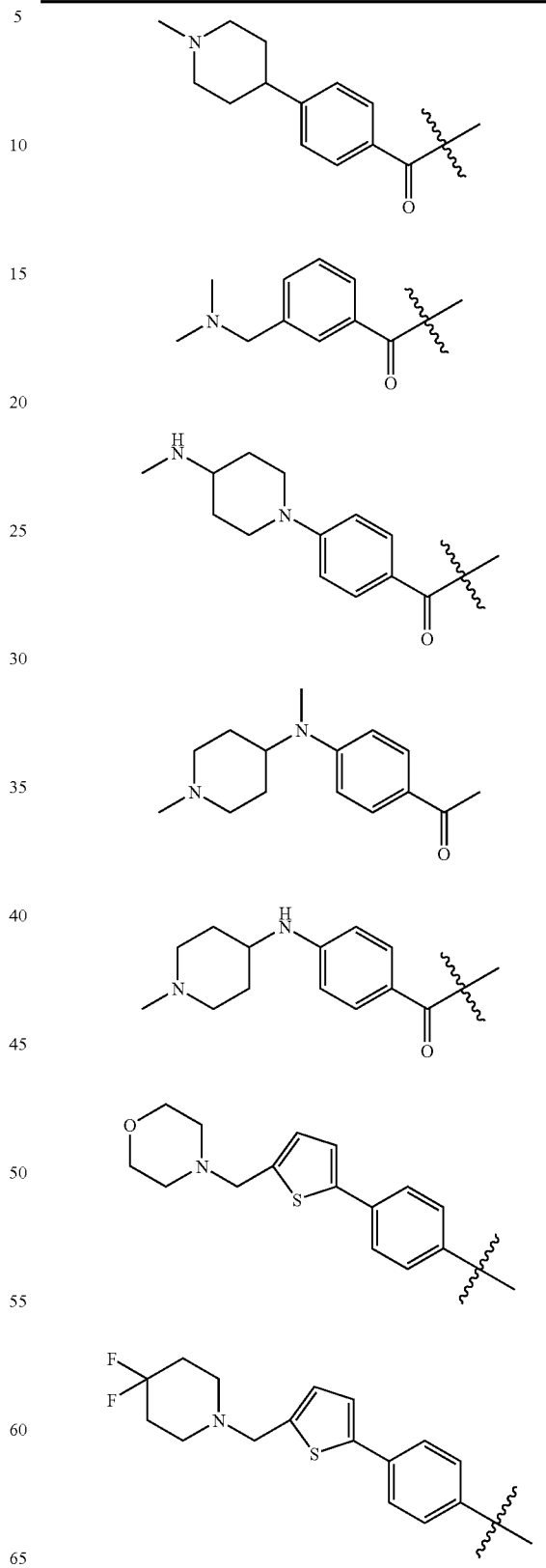

TABLE C-continued

P3 groups

[Chemical structures of P3 groups]

Additional aspects of the invention include a pharmaceutical composition comprising a compound as defined above and a pharmaceutically acceptable carrier or diluent therefor.

A further aspect of the invention is the use of a compound as defined above in the manufacture of a medicament for the treatment of disorders mediated by cathepsin K, such as:
- osteoporosis,
- gingival diseases such as gingivitis and periodontitis,
- Paget's disease,
- hypercalcaemia of malignancy
- metabolic bone disease
- diseases characterised by excessive cartilege or matrix degradation, such as osteoarthritis and rheumatoid arthritis,
- bone cancers including neoplasia,
- pain.

The compounds of the invention can form salts which form an additional aspect of the invention. Appropriate pharmaceutically acceptable salts of the compounds of Formula II include salts of organic acids, especially carboxylic acids, including but not limited to acetate, trifluoroacetate, lactate, gluconate, citrate, tartrate, maleate, malate, pantothenate, isethionate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-napthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids. The compounds of Formula II may in some cases be isolated as the hydrate.

It will be appreciated that the invention extends to prodrugs, solvates, complexes and other forms releasing a compound of formula II in vivo.

While it is possible for the active agent to be administered alone, it is preferable to present it as part of a pharmaceutical formulation. Such a formulation will comprise the above defined active agent together with one or more acceptable carriers/excipients and optionally other therapeutic ingredients. The carrier(s) must be acceptable in the sense of being compatible with the other ingredients of the formulation and not deleterious to the recipient.

The formulations include those suitable for rectal, nasal, topical (including buccal and sublingual), vaginal or parenteral (including subcutaneous, intramuscular, intravenous and intradermal) administration, but preferably the formulation is an orally administered formulation. The formulations may conveniently be presented in unit dosage form, e.g. tablets and sustained release capsules, and may be prepared by any methods well known in the art of pharmacy.

Such methods include the step of bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of Formula II or its pharmaceutically acceptable salt in conjunction or association with a pharmaceutically acceptable carrier or vehicle. If the manufacture of pharmaceutical formulations involves intimate mixing of pharmaceutical excipients and the active ingredient in salt form, then it is often preferred to use excipients which are non-basic in nature, i.e. either acidic or neutral.

Formulations for oral administration in the present invention may be presented as discrete units such as capsules, cachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion and as a bolus etc.

With regard to compositions for oral administration (e.g. tablets and capsules), the term suitable carrier includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring or the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

The appropriate dosage for the compounds or formulations of the invention will depend upon the indication and the patient and is readily determined by conventional animal trials. Dosages providing intracellular (for inhibition of physiological proteases of the papain superfamily) concentrations of the order 0.01-100 µM, more preferably 0.01-10 µM, such as 0.1-25 µM are typically desirable and achievable.

Compounds of the invention are prepared by a variety of solution and solid phase chemistries.

The compounds are typically prepared as building blocks reflecting the P1, P2 and P3 moieties of the end product inhibitor. Without in any way wishing to be bound by theory, or the ascription of tentative binding modes for specific variables, the notional concepts P1, P2 and P3 as used herein are provided for convenience only and have substantially their conventional Schlecter & Berger meanings and denote those portions of the inhibitor believed to fill the S1, S2, and S3 subsites respectively of the enzyme, where S1 is adjacent the cleavage site and S3 remote from the cleavage site. Compounds defined by Formula I are intended to be within the scope of the invention, regardless of binding mode.

Broadly speaking the P1 building block will be an N-protected-6-fluoro-3-oxo-hexahydro-furo[3,2-b]pyrrole, P2 will be an N-protected amino acid, whereas P3 typically comprises a capping group such as a substituted, heteroaroyl or aroyl moiety.

The suitably protected individual building blocks can first be prepared and subsequently coupled together i.e. P2+P1→P2–P1. Alternatively, precursors of the building blocks can be coupled together and modified at a later stage of the synthesis of the inhibitor sequence. Further building blocks, precursors of building blocks or prefabricated bigger fragments of the desired structure, can then be coupled to the growing chain, e.g. $R^3$-E-P2*+P1→$R^3$-E-P2–P1 or $R^3$-E*+ P2–P1→$R^3$-E-P2–P1, where * denotes an activated form.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (pnitrophenyl ester, N-hydroxysuccinimido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", 2nd rev ed., Springer-Verlag, Berlin, Germany, (1993) hereafter simply referred to as Bodanszky, the contents of which are hereby incorporated by reference. Examples of suitable coupling agents are N,N'-dicyclohexylcarbodiimide, 1-hydroxybenzotriazole in the presence of N,N'-dicyclohexylcarbodiimide or N-ethyl-N'-[(3dimethylamino)propyl]carbodiimide. A practical and useful coupling agent is the commercially available (benzotriazol-1-yloxy)tris-(dimethylamino)phosphonium hexafluorophosphate, either by itself or in the present of 1-hydroxybenzotriazole or 4-DMAP. Another practical and useful coupling agent is commercially available 2-(IH-benzotriazol-1-yl)-N,N,N',N'-tetramethyluronium tetrafluoroborate. Still another practical and useful coupling agent is commercially available 0-(7-azabenzotrizol-1-yl)-N, N,N', N'-tetramethyluronium hexafluorophosphate.

The coupling reaction is conducted in an inert solvent, e. g. dichloromethane, acetonitrile or dimethylformamide. An excess of a tertiary amine, e. g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent non-natural amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1 981), hereafter referred to simply as Greene, the disclosures of which are hereby incorporated by reference.

The alpha-carboxyl group of the C-terminal residue is usually protected as an ester that can be cleaved to give the carboxylic acid. Protecting groups that can be used include 1) alkyl esters such as methyl, trimethylsilyl and t.butyl, 2) aralkyl esters such as benzyl and substituted benzyl, or 3) esters that can be cleaved by mild base or mild reductive means such as trichloroethyl and phenacyl esters.

The alpha-amino group of each amino acid to be coupled is typically N-protected. Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted bensyloxycarbonyls, and 9-fluorenylmethyloxycarbonyl (Fmoc); 3) aliphatic carbamate groups such as tertbutyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such asphenylthiocarbonyl and dithiasuccinoyl. The preferred alpha-amino protecting group is either Boc or Fmoc. Many amino acid derivatives suitably protected for peptide synthesis are commercially available.

The alpha-amino protecting group is typically cleaved prior to the next coupling step. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature usually 20-22° C.

Any of the natural or non-natural amino acids having side chain functionalities will typically be protected during the preparation of the peptide using any of the above described groups. Those skilled in the art will appreciate that the selection and use of appropriate protecting groups for these side chain functionalities depend upon the amino acid and presence of other protecting groups in the peptide. In the selection of such protecting groups it is desirable that the group is not removed during the deprotection and coupling of the alpha-amino group.

For example, when Boc is used as the alpha-amino protecting group, the following side chain protecting groups are suitable: p-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the alpha-amine protection, usually tert. butyl based protecting groups are acceptable. For instance, Boc can be used for lysine and arginine, tert.butyl ether for serine, threonine and hydroxyproline, and tert-butyl ester for aspartic acid and glutamic acid. Triphenylmethyl (Trityl) moiety can be used to protect the sulfide containing side chain of cysteine.

Once the inhibitor sequence is completed any protecting groups are removed in whatever manner is dictated by the choice of protecting groups. These procedures are well known to those skilled in the art.

The first stage in a synthesis of compounds of the general formula II is typically the preparation in solution of a functionalized P1 building block. Different nomenclature of compounds according to the present invention can be used. For convenience the carbohydrate nomenclature will generally be used herein. A typical scheme towards a bicyclic P1 group starts with the ring closure of a suitably protected intermediate which is available in 4 steps from 1,2:5,6-di-O-isopropylidene-D-allofuranose, described by Mayer zum Reckendorf, Chem. Ber. 101 (1968), 3802-3807, giving a precursor of 3S, 4R stereochemistry.

Scheme 1.

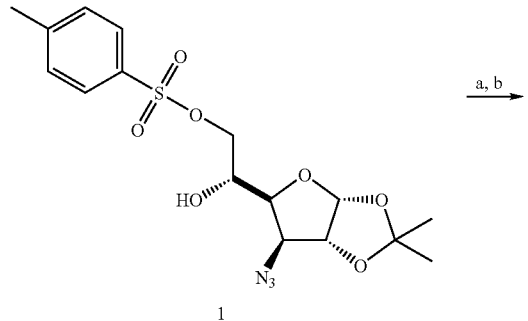

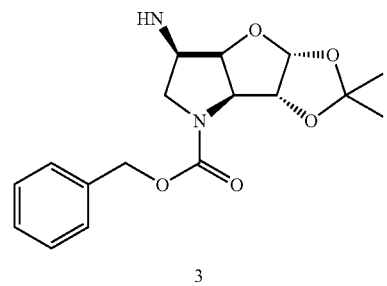

a) H$_2$, Pd/C, methanol. b) benzylchloroformate, pyridine, dichloromethane

In Scheme 1 the azide group of derivative 1 is reduced for example by catalytic hydrogenation using palladium on charcoal or other catalysts suitable, in a suitable solvent such as an alcohol, like ethanol or methanol into the free amine. The obtained nucleophilic nitrogen reacts spontaneously, or optionally in the presence of a suitable base like such as triethyl amine or sodium acetate, with the C-6 position forming a 5,5-bicycle. The leaving group at C-6 is not limited to sulfonate esters, but also other leaving groups such as halogen could be used throughout the synthesis of compounds according to the present invention. The reduction of the azide residue into an amine could also be performed by other methods known from literature, such as treating the azide derivative with a trialkyl- or triarylphosphine followed by hydrolysis of the formed imine derivative. After the ring closure the amine may be N-protected with a suitable protecting group such as a carbamate, like benzyl carbamate of compound 3 or any other similar protecting group which is normally not cleaved with acid. Suitable protecting groups which can be found in: Protective groups in organic chemistry, 3$^{rd}$ edition, 1999, Theodora W. Greene and Peter G. M. Wuts (Wiley&sons).

For a 3R, 4S bicycle a similar approach could be used starting from 3-azido-3-deoxy-1,2:5,6-di-O-isopropylidene-D-gulofuranose which can be prepared as described in Tetrahedron Asymmetry, 10 (1999) 1855-1859. This intermediate can then be treated as described in Scheme 2.

Scheme 2.

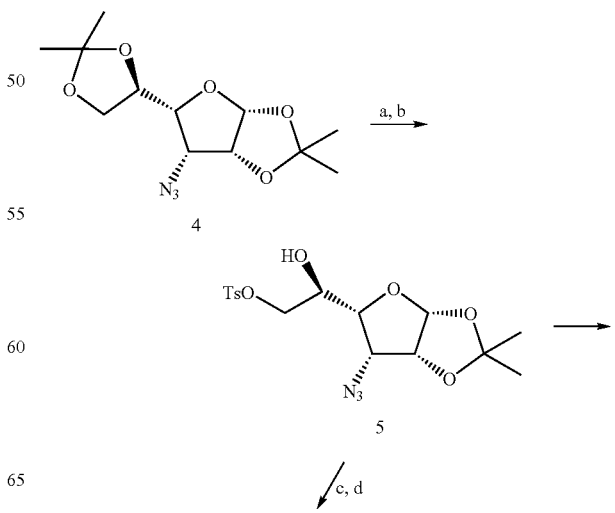

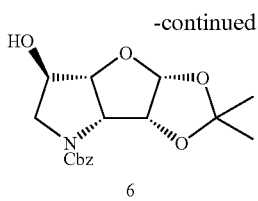

6 a) aq. acetic acid.
b) p-toluenesulfonyl chloride, pyridine, DCM,
c) H₂, Pd/C, methanol.
b) benzylchloroformate, pyridine, dichloromethane.

Compound 4 can be treated with a mild acid, such as diluted acetic acid or similar, which can selectively hydrolyze the 5,6-acetal of compound 4, to obtain a diol. The primary alcohol can be selectively reacted with an alkyl- or arylsulfonyl chloride like p-toluenesulfonyl chloride to give compound 5. The azide group of derivative 5 is reduced for example by catalytic hydrogenation using palladium on charcoal or other catalysts suitable, in a suitable solvent such as an alcohol, like ethanol or methanol into the free amine. The obtained nucleophilic nitrogen reacts spontaneously, or optionally in the presence of a suitable base like such as triethyl amine or sodium acetate, with the C-6 position forming a 5,5-bicycle which can be N-protected with a suitable protecting group such as its benzyl carbamate (Cbz) to give compound 6.

Alternatively 3-azido-3-deoxy-1,2:5,6-di-O-isopropylidene-D-idofuranose (Bull. Chem. Soc. Japan, 57, 1(1984), 237-241) could be a suitable starting material for the 3R, 4S bicycle according to Scheme 3.

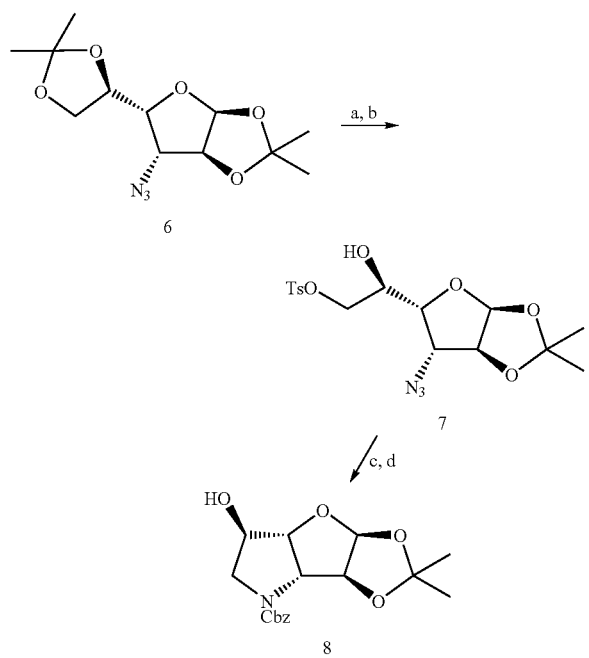

Scheme 3.

a) aq. acetic acid.
b) p-toluenesulfonyl chloride, pyridine, DCM,
c) H₂, Pd/C, methanol.
b) benzylchloroformate, pyridine, dichloromethane.

Compound 6 can be treated with a mild acid, such as diluted acetic acid or similar, which can selectively hydrolyze the 5,6-acetal of compound 6, to obtain a diol. The primary alcohol can be selectively reacted with an alkyl- or arylsulfonyl chloride like p-toluenesulfonyl chloride to give compound 7. The azide group of derivative 7 is reduced for example by catalytic hydrogenation using palladium on charcoal or other catalysts suitable, in a suitable solvent such as an alcohol, like ethanol or methanol into the free amine. The obtained nucleophilic nitrogen reacts spontaneously, or optionally in the presence of a suitable base like such as triethyl amine or sodium acetate, with the C-6 position forming a 5,5-bicycle which can be N-protected with a suitable protecting group such as its benzyl carbamate (Cbz) to give compound 8.

The ring closure is not limited to the substrates shown above but could also be applied to derivatives as depicted in Scheme 4.

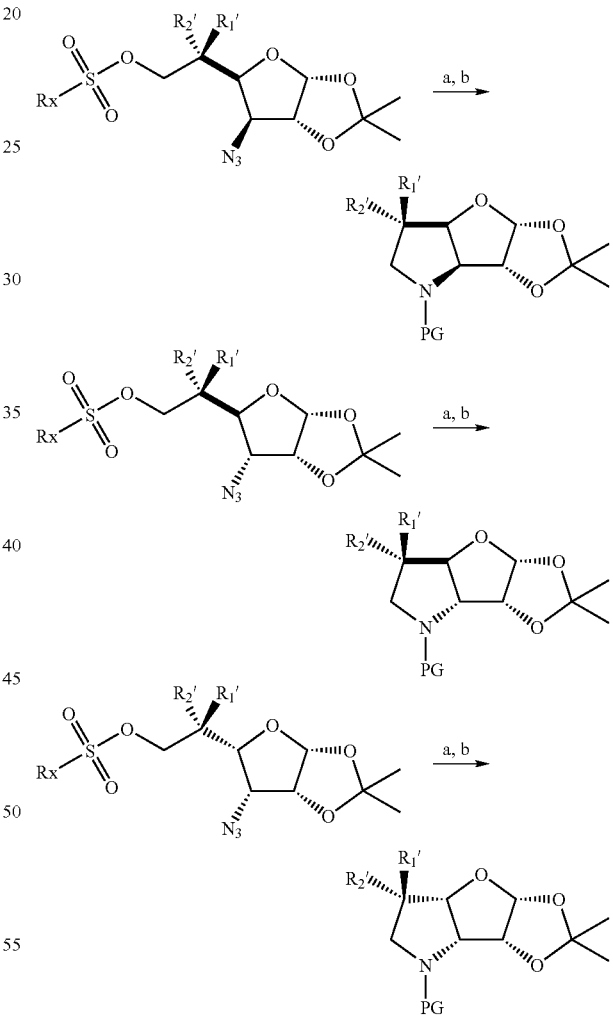

a) reduction of azide into an amine followed by ring closure.
b) protection of amine.

Rx in Scheme 4 may be chosen from methyl, trifluoromethyl, p-methylphenyl or similar residues present in readily available alkylsulfonylhalides, preferably a bulky Rx suitable for regioselective reaction on the primary alcohol of a diol as described in Chem. Ber. 101 (1968), 3802-3807. $R^{1'}$ and $R^{2'}$ are $R^1$ and $R^2$ as defined. Pg could be a suitable protecting group such as a carbamate, like benzyl carbamate or any similar protecting group which is not normally cleaved with acid.

Further substrates for the ring closure reaction could be compounds depicted in Scheme 5.

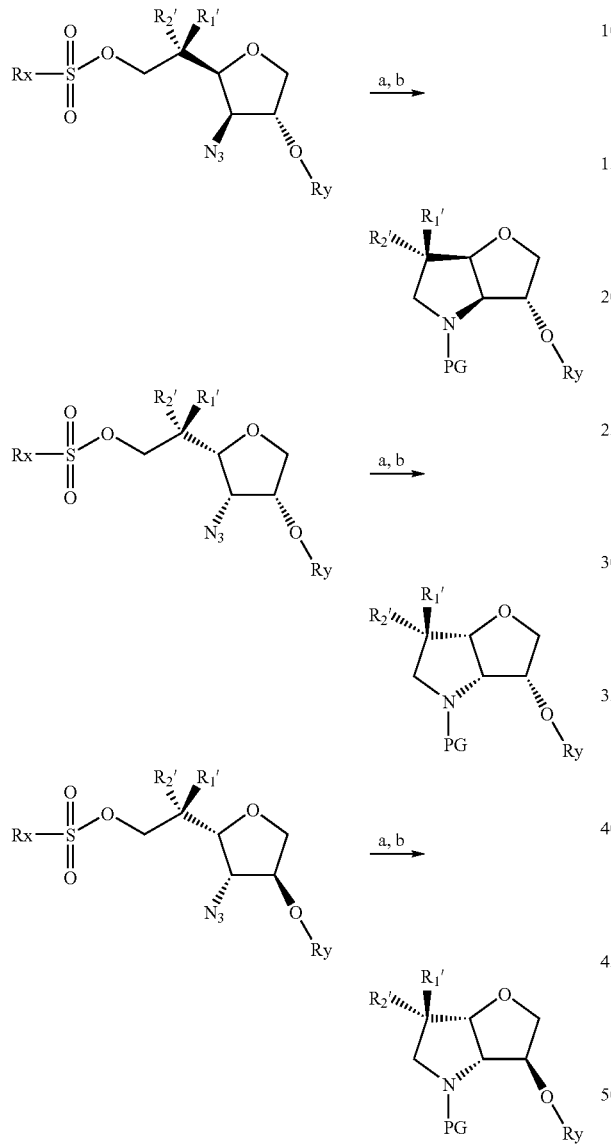

a) reduction of azide into an amine followed by ring closure.
b) protection of amine (optional).

Rx in Scheme 5 can be chosen from methyl, trifluoromethyl, p-methylphenyl or similar residues present in readily available alkylsulfonylhalides, preferably a bulky Rx suitable for regioselective reaction on the primary alcohol of a diol as described in Chem. Ber. 101 (1968), 3802-3807. $R^{1'}$ and $R^{2'}$ are $R^1$ and $R^2$ as defined above. Ry can be hydrogen or a hydroxyl protective group, preferably an ether type protective group. Preferably Ry is hydrogen. PG could be a suitable N-protecting group such as a carbamate, for derivatives in Scheme 5, Ry is typically hydrogen.

Other methodologies to obtain a 5,5-bicycle is disclosed by G. Lin and Z. Shi, Tetrahedron, 53, 4, 1369-1382, 1997.

Further modification of the 5,5-bicyclic compound obtained in scheme 1 is outlined in Scheme 6.

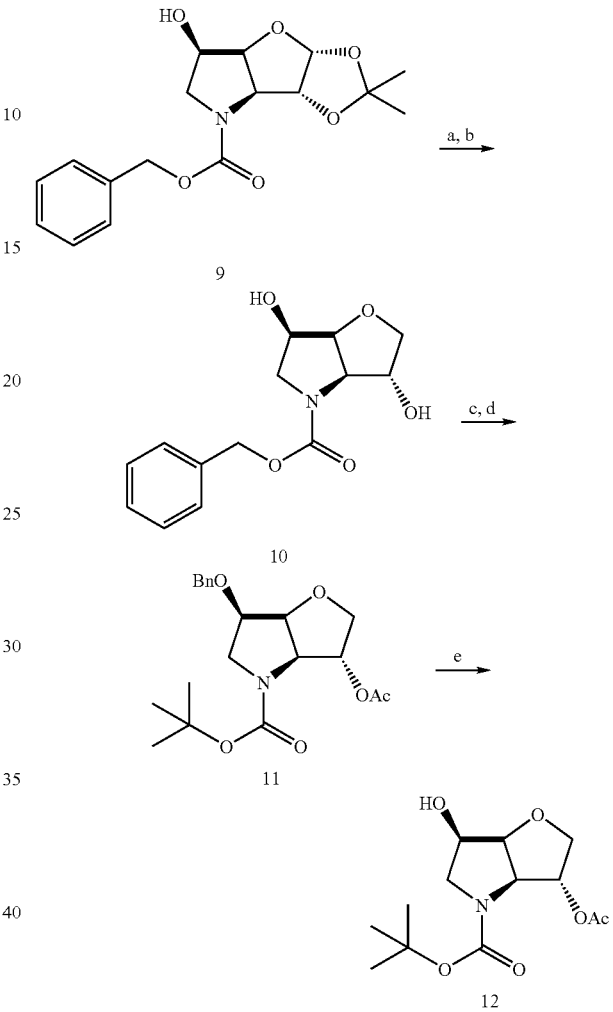

a) benzyl bromide, sodium hydride, DMF.
b) $BF_3 \cdot Et_2O$, $Et_3SiH$, DCM.
c) $H_2$, Pd/C, $Boc_2O$, 1:1 EtOAc-EtOH.
d) pyridine, acetic anhydride.
e) $H_2$, Pd/C, EtOAc Compound 9 is protected with a suitable acid stable protecting group such as substituted methyl ether, in particular a benzyl ether, by treating the mono-ol 9 with a base such as sodium hydride or sodium hydroxide in an aprotic solvent such as N,N-dimethylformamide (DMF) in the presence of the desired alkylating agent such as the benzyl halide, in particular benzyl bromide. The obtained material can then be reduced into compound 10 according to methods described by G. J. Ewing and M. J. Robins, Org. Lett. 1, 4, 1999, 635-636, or by references therein. Preferably the reduction is performed with excess boron trifluoride etherate in the presence of a reducing agent such as trialkylsilane, in particular with excess triethylsilane in a suitable non-protic solvent such as dichloromethane. Catalytic hydrogenation of compound 10 using for example palladium-on-charcoal in a suitable solvent or solvent mixture such as ethyl acetate-ethanol in a hydrogen atmosphere, in the presence of di-tert-butyl dicarbonate followed by treatment of the product with acetic anhydride in pyridine gives intermediate 11. By repeated catalytic hydrogenation, as described above, the mono-ol 12 is obtained.

A fluorine can be introduced on compound 12, and the bicyclic compound then N-deprotected according to Scheme 7.

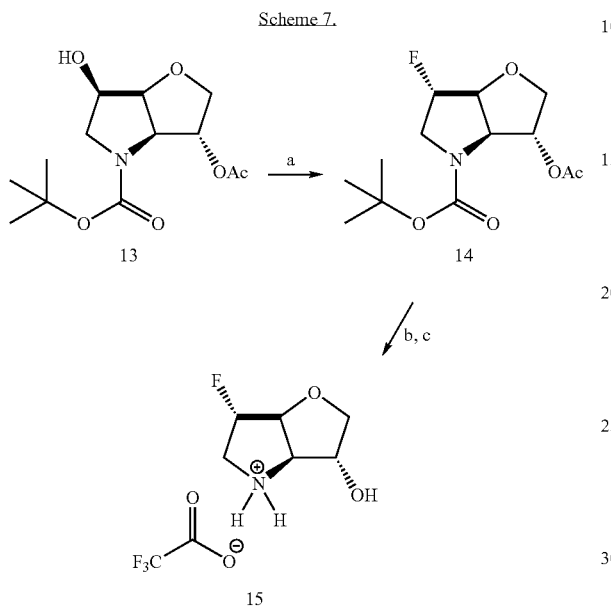

a) Deoxo-Fluor®, dichloromethane.
b) methanolic sodium methoxide.
c) 1:1 dichloromethane-trifluoroacetic acid.

Compound 13 can be treated with a fluorinating agent such as [bis-(2-methoxyethyl)aminosulfur trifluoride] (Deoxo-Fluor®) or with similar fluorinating agents such as diethylaminosulfur trifluoride (DAST) which gives the product 14 with inversion of configuration at C-5. Compound 14 is then deacetylated by treatment for example with methanolic sodium methoxide, or any similar alkaline solutions with an inorganic base such as sodium hydroxide or sodium carbonate, followed by N-deprotection using acidic conditions such as dichloromethane-trifluoroacetic acid solutions or other methods which could be found in: Protective Groups in Organic Chemistry, 3$^{rd}$ edition, 1999, Theodora W. Greene and Peter G. M. Wuts (Wiley & Sons).

Alternatively the epimeric fluorine can be obtained by treating derivative 9 above according to Scheme 8.

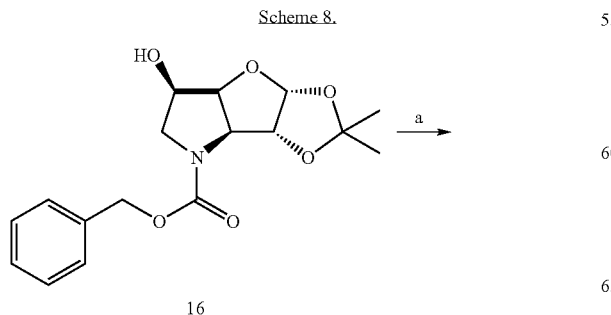

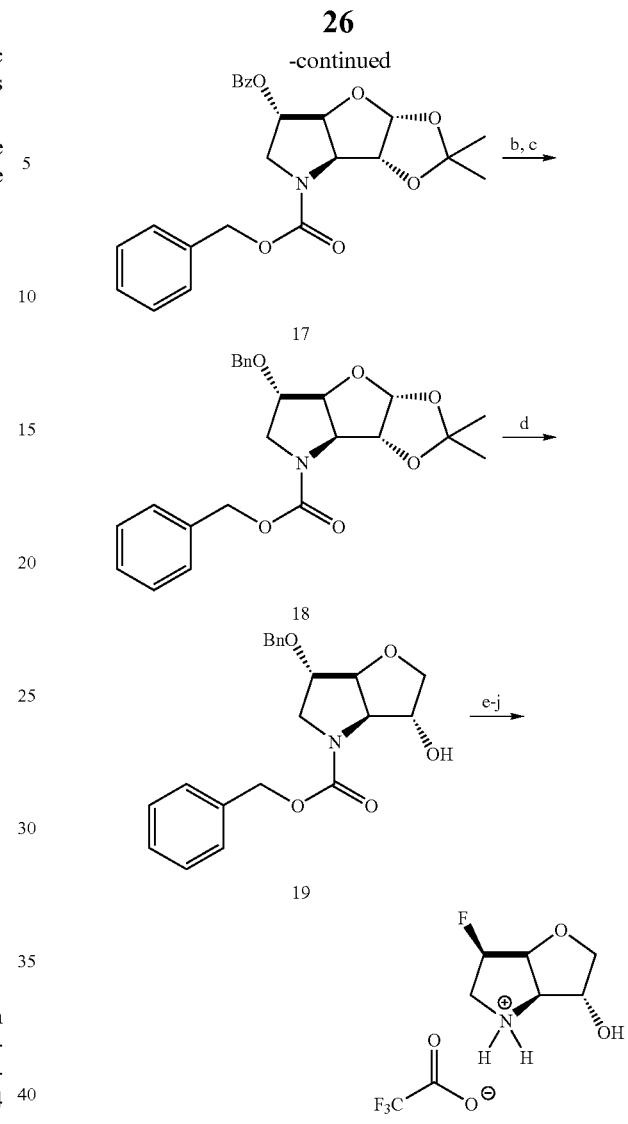

a) diisopropylazodicarboxylate, benzoic acid, PPh$_3$, THF. b) methanolic sodium methoxide. c) benzyl bromide, sodium hydride, DMF. d) BF$_3$•Et$_2$O, Et$_3$SiH, dichloromethane. e) H$_2$, Pd/C, Boc$_2$O, 1:1 EtOAc-EtOH. f) pyridine, acetic anhydride. g) H$_2$, Pd/C, EtOAc. h) Deoxo-Fluor®, dichloromethane. i) methanolic sodium methoxide. j) 1:1 dichloromethane-thrifluoroacetic acid.

Inversion of configuration at C-5 can be accomplished by reacting compound 16 under Mitsunobo conditions which gives a benzoate ester. Ester hydrolysis with methanolic sodium methoxide followed by treatment of the mono-ol with benzyl bromide provides benzyl protected epimer 17. Reaction steps d-j in Scheme 8 are as described for Schemes 6 and 7.

A further route to a "difluoro derivative" wherein R$^1$ and R$^2$ are fluoro is shown in Scheme 9.

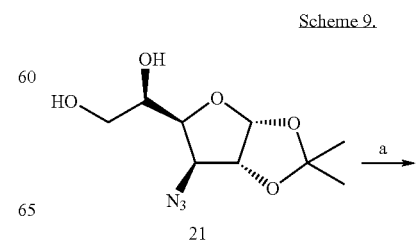

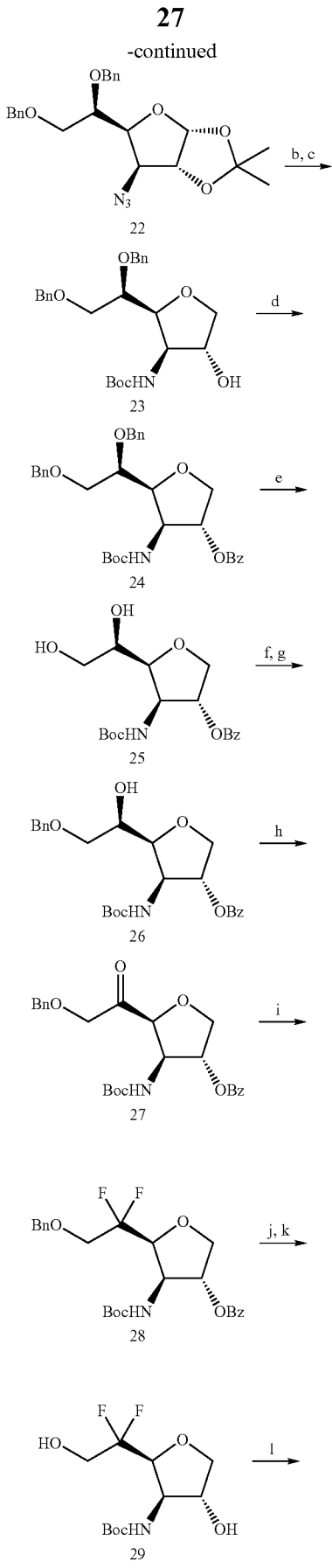

a) benzyl bromide, sodium hydride, DMF. b) Et₃SiH, BF₃·Et₂O or trimethylsilyl trifluoromethanesulfonate, DCM. c) H₂, Pd/C, Boc₂O, EtOAc-EtOH. d) benzoyl chloride, pyridine, DCM. e) H₂, Pd/C, EtOAc. f) Bu₂SnO, toluene, reflux. g) benzyl bromide, cesium fluoride, DMF. h) Dess-Martin periodinane. i) Deoxo-Fluor® or diethylaminosulfur trifluoride, DCM. j) methanolic sodium methoxide. k) H₂, Pd/C, EtOAc. l) p-toluenesulfonyl chloride, pyridine, DCM. m) DCM, trifluoroacetic acid. n) triethylamine, dichloromethane.

The synthesis of the P1 building block can be started from compound 21 (3-azido-3-deoxy-1,2-O-isopropylidene-D-allofuranose) which is described by Mayer zum Reckendorf, Chem. Ber. 101 (1968), 3802-3807. Treatment of compound 21 with a benzylating agent like benzyl bromide or benzyl chloride in the presence of a base, such as sodium hydride or sodium hydroxide in a aprotic polar solvent, such as N,N-dimethylformamide gives derivative 22. Compound 22 is then treated with a trialkyl silane, such as triethyl silane, with an excess of a Lewis acid such as boron trifluoride etherate or trimethylsilyl trifluoromethanesulfonate, in a aprotic solvent such as dichloromethane. The resulting azide can then be selectively reduced by catalytic hydrogenation using for example Palladium on charcoal in the presence of di-tert-butyl carbonate to obtain compound 23. Alternatively the azide could be reduced with other methods known from literature such as triphenylphosphine-water, followed by protection giving a suitable carbamate. In order to avoid problems with regioselectivity in the following steps, compound 23 could be treated with an acylating agent such as an acyl chloride or acid anhydride, such as benzoyl chloride, in neat organic base such as pyridine or triethyl amine, or in a mixture of an aprotic solvent such as dichloromethane and a base to give compound 24. Catalytic hydrogenation of compound 24 as described above gives diol 25. Selective benzylation at the primary alcohol of compound 25 can be accomplished by several methods known from the literature. In Scheme 9 the diol is refluxed with dibutyl tin oxide in a suitable solvent such as toluene to form a tin acetal. The tin acetal can then be reacted with a small excess of benzyl bromide and cesium fluoride in DMF giving the desired compound 26. Oxidation of 26 with a suitable oxidizing agent such as Dess-Martin periodinane in dichloromethane converts the secondary alcohol into the keto compound 27 suitable to convert into the difluoride 28. This can be accomplished by treating compound 27 with an excess fluorinating agent such as Deoxo-Fluor®, or with diethylaminosulfur trifluoride (DAST), in an aprotic solvent such as dichloromethane or 1,2-dichloroethane. The benzoate ester of compound 28 can be cleaved with alkali such as methanolic sodium methoxide, followed by debenzylation using catalytic hydrogenation to obtain diol 29. Selective introduction of a sulfonate ester at the primary alcohol can be accomplished by treating the compound 29 with a small excess of alkyl- or arylsulfonyl chloride in the presence of a base such as pyridine in suitable solvent such as dichloromethane, adding the sufonylating agent at reduced temperature and slowly increase up to room temperature, which gives mono-ol 30. Treatment of compound 30 under acidic conditions such as mixtures of dichlormethane-trifluoroacetic acid liberates the amine, and treating the product with a base such as triethyl amine promotes the internal ring closure which gives building block 31.

Alternative routes to 5,5-bicycles are shown in Schemes 10 and 11.

In Scheme 11 an alternative route to a difluoro-5,5-bicycle is depicted.

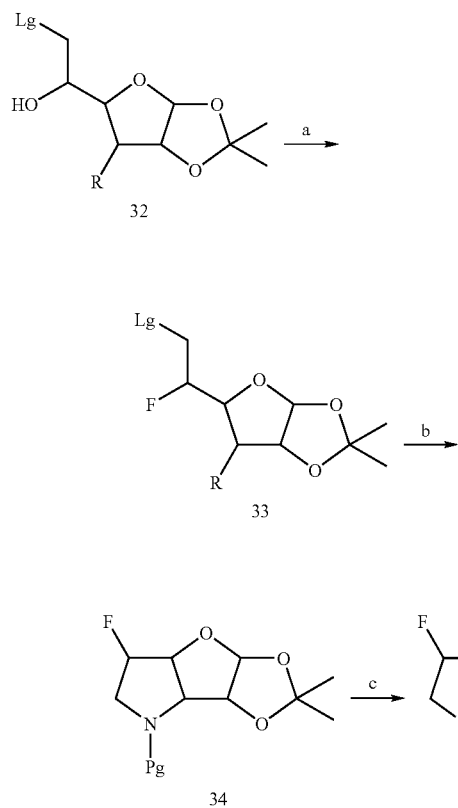

Scheme 10.

a) fluorinating agent. b) reduction of amine or N-deprotection, optionally followed by N-protection. c) reducing agent.

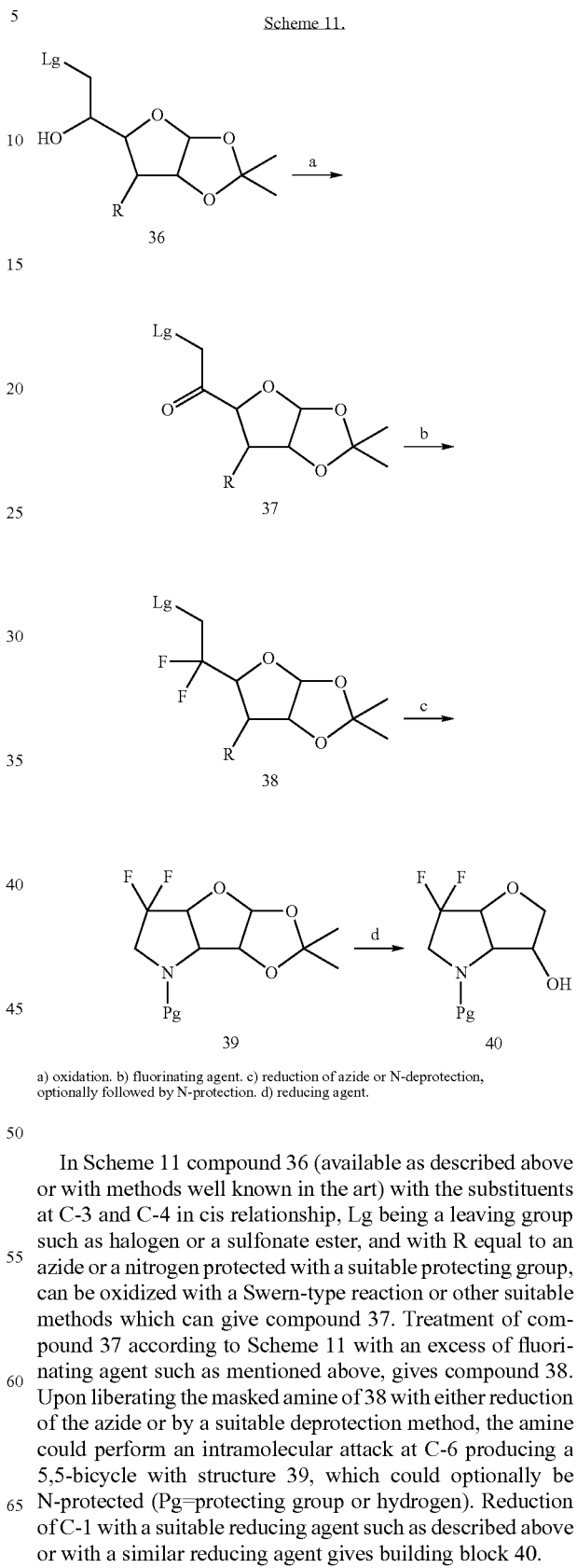

Scheme 11.

a) oxidation. b) fluorinating agent. c) reduction of azide or N-deprotection, optionally followed by N-protection. d) reducing agent.

In Scheme 10 a derivative such as compound 32 (available as described above or with methods well known in the art) with the substituents at C-3 and C-4 in cis relationship, Lg being a leaving group such as halogen or a sulfonate ester, and with R equal to an azide or a nitrogen protected with a suitable N-protecting group, can be treated with a fluorinating agent such as mentioned above, producing compound 33. Upon liberating the masked amine with either reduction of the azide or by a suitable deprotection method, the amine could perform an intramolecular attack at C-6 producing a 5,5-bicycle with structure 34, which could optionally be N-protected (Pg=protecting group or hydrogen). Reduction of C-1 with a suitable reducing agent such as described above or with a similar reducing agent would give building block 35.

In Scheme 11 compound 36 (available as described above or with methods well known in the art) with the substituents at C-3 and C-4 in cis relationship, Lg being a leaving group such as halogen or a sulfonate ester, and with R equal to an azide or a nitrogen protected with a suitable protecting group, can be oxidized with a Swern-type reaction or other suitable methods which can give compound 37. Treatment of compound 37 according to Scheme 11 with an excess of fluorinating agent such as mentioned above, gives compound 38. Upon liberating the masked amine of 38 with either reduction of the azide or by a suitable deprotection method, the amine could perform an intramolecular attack at C-6 producing a 5,5-bicycle with structure 39, which could optionally be N-protected (Pg=protecting group or hydrogen). Reduction of C-1 with a suitable reducing agent such as described above or with a similar reducing agent gives building block 40.

A convenient route to compounds wherein R1 or R2 is a halogen such as chloro is depicted in Scheme 12

Scheme 12

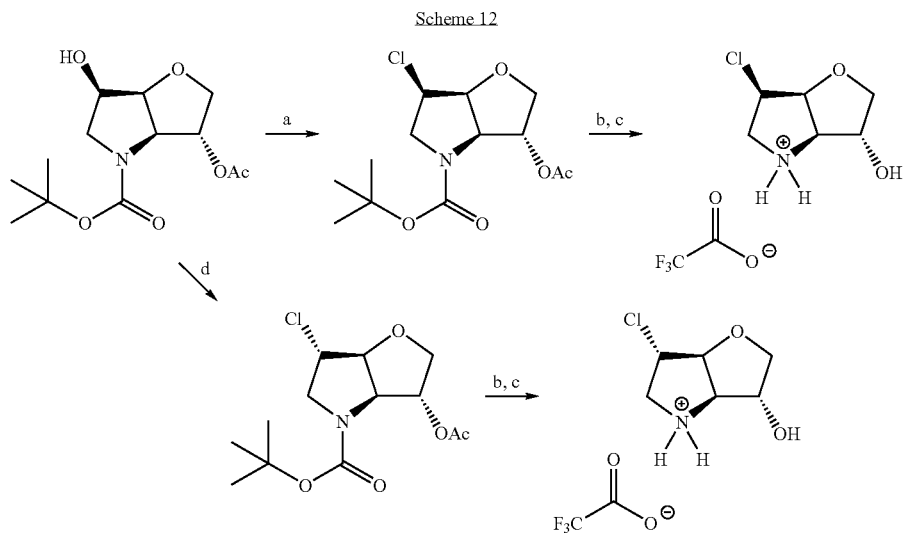

a) Thionyl chloride. b) methanolic sodium methoxide. c) 1:1 dichloromethane-trifluoroacetic acid. d) thionyl chloride, pyridine The P1 building block is then elongated with the natural or non natural P2 amino acid and the P3 group by conventional solution or solid phase chemistries, such as those outlined or exemplified below, or disclosed in WO00/69855 or WO02/057270. P2 and P3 groups are either commercially available as enantiomers or resolvable from the racemate or obtainable using simple chemical transformations known to one skilled in the art. For example, 4-(methyl-piperazine-1-yl)-benzoic acid can be obtained using Buchwald chemistry (S. L. Buchwald & J. P. Wolfe, Journal of Organic Chemistry, 2000, 65, 1144) and subsequently elaborated. Other P3 cores such as 4-(1-piperidin-4-yl)-benzoic acid are prepared from 1-(4-phenyl-piperidine-1-yl)-ethanone using a Friedel-Crafts acylation reaction and subsequently elaborated using standard chemical transformations known to one skilled in the art. Alternatively, other P3 moieties, such as 5-[2-(4-morpholinyl)ethoxy]-2-benzofuran-2-carboxylic acid, are prepared using Mitsunobu reactions on solid phase as detailed by L. S. Richter & T. R. Gadek in Tetrahedron Lett., 1994, 35, 4705.

Scheme 13. Typical elongation of a cyclic ketone

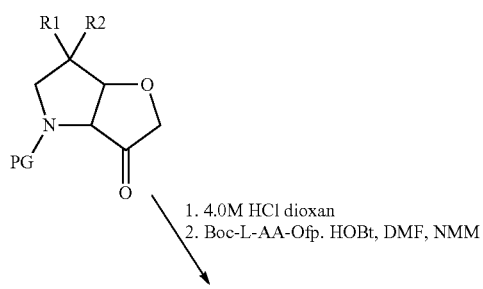

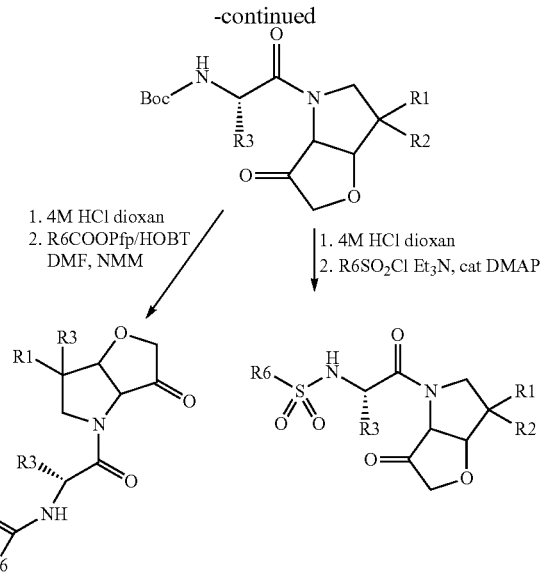

Urethane compounds i.e. E is —OC(=O)— can be formed for example by reaction of an $R_6$ alcohol with the isocyanate of the P2 amino acid. The isocyanate, or equivalent reactive intermediate, can be formed by reaction of the amino group of the P2-amino acid with phosgene, or with dinitrophenylcarbonate in the presence of a suitable base, e.g. triethylamine. Alternatively they can be formed by reaction of the amino group of the P2 amino acid with a suitable chloroformate, e.g. benzylchloroformate.

Sulphonamide derivatives i.e. E=S(=O)$_2$— can be prepared by reaction of the amino group of the P2 amino acid with a suitable sulfonyl chloride in a solvent such as dichloromethane in the presence of a suitable base such as triethylamine or dimethylaminopyridine.

Sulphamide derivatives i.e. E=NRaS(=O)$_2$— can be prepared by reacting a suitable R$_6$ amine in a sulphonyl chloride solvent followed by reaction of the formed sulfamoyl chloride derivative with the amino group of the above mentioned R$_4$ amino acid in a solvent such as dichloromethane in the presence of a suitable base such as triethylamine.

Alternatively the P1 building block as the hydroxyl may be elongated and subsequently oxidised as shown in Scheme 14 and the Examples.

Scheme 14, Typical elongation of an hydroxylated P1 building block

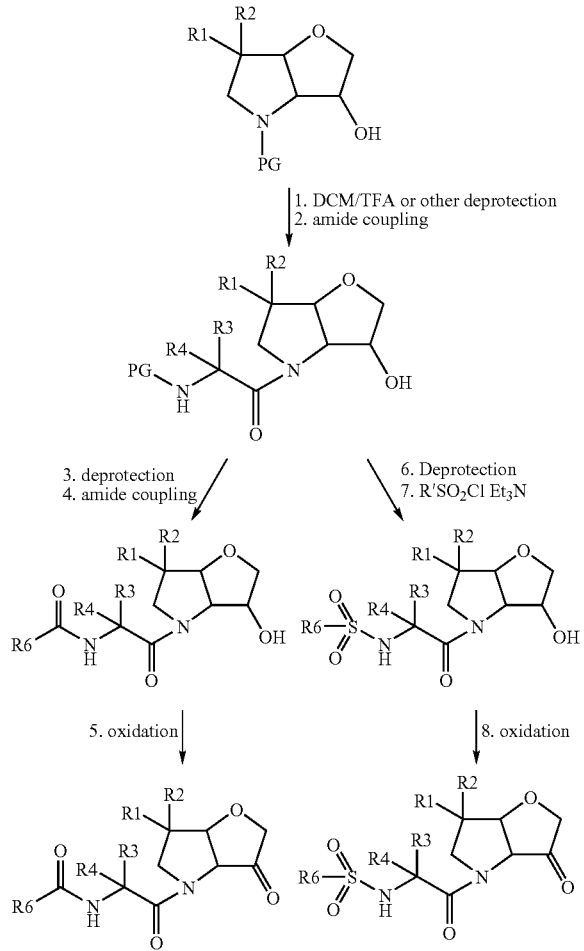

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups in Organic Synthesis" (John Wiley & Sons, New York, 1981), which is hereby incorporated by reference. N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl, and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 4-methoxybenzyloxycarbonyl, 2-nitro4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butoxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-methoxycarbonyl, cyclopentyloxycarbonyl, adamantyloxycarbonyl, cyclohexyloxycarbonyl, phenylthiocarbonyl, and the like; alkyl groups such as benzyl, triphenylmethyl, benzyloxymethyl and the like; and silyl groups such as trimethylsilyl and the like. Favoured N-protecting groups include formyl, acetyl, benzoyl, pivaloyl, t-butylacetyl, phenylsulfonyl, benzyl, t-butoxycarbonyl (BOC) and benzyloxycarbonyl (Cbz).

Hydroxy and/or carboxy protecting groups are also extensively reviewed in Greene ibid and include ethers such as methyl, substituted methyl ethers such as methoxymethyl, methylthiomethyl, benzyloxymethyl, t-butoxymethyl, 2-methoxyethoxymethyl and the like, silyl ethers such as trimethylsilyl (TMS), t-butyldimethylsilyl (TBDMS) tribenzylsilyl, triphenylsilyl, t-butyldiphenylsilyl triisopropyl silyl and the like, substituted ethyl ethers such as 1-ethoxymethyl, 1-methyl-1-methoxyethyl, t-butyl, allyl, benzyl, p-methoxybenzyl, diphenylmethyl, triphenylmethyl and the like, aralkyl groups such as trityl, and pixyl (9-hydroxy-9-phenylxanthene derivatives, especially the chloride). Ester hydroxy protecting groups include esters such as formate, benzylformate, chloroacetate, methoxyacetate, phenoxyacetate, pivaloate, adamantoate, mesitoate, benzoate and the like. Carbonate hydroxy protecting groups include methyl vinyl, allyl, cinnamyl, benzyl and the like.

DETAILED DESCRIPTION OF THE EMBODIMENTS

Various embodiments of the invention will now be described by way of illustration only with reference to the following Examples.

Example 1

Construction of P1 Building Block

Step a)

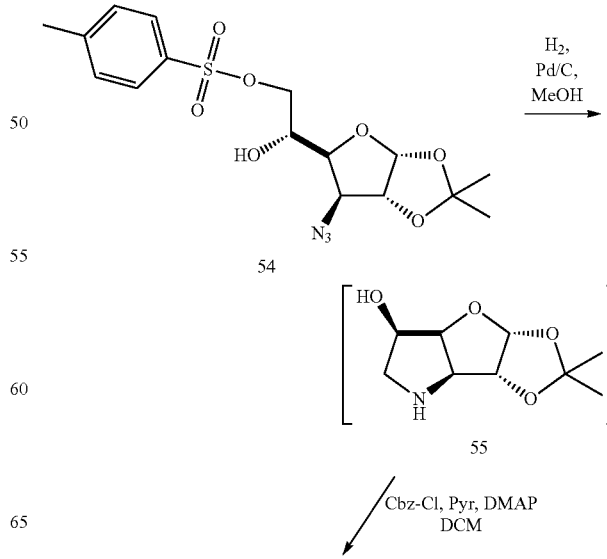

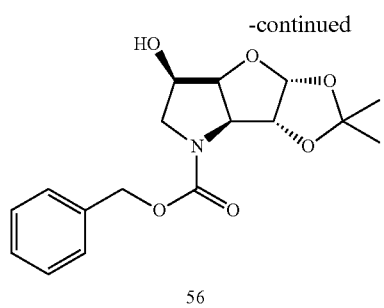

56

A mixture of 54 (5.2 g, 13.0 mmol), palladium-on-carbon (10%, Acros, 0.66 g) in methanol was hydrogenated at slight positive pressure. The hydrogen was changed 3 times over a period of 1 h, after TLC (petroleum ether-ethyl acetate 7:3 and dichloromethane-methanol 9:1, staining with ammonium molybdate-cerium sulfate) indicated complete conversion of the starting material into a major non-UV active spot which colours AMC, and some weaker higher moving spots (dichloromethane-methanol 9:1). The reaction mixture was then filtered through Celite and concentrated which gave crude compound 55.

To a suspension of the residue in dichloromethane (60 ml) and pyridine (3.2 ml, 40 mmol) at 0° C. was added benzylchloroformate (0.93 ml, 6.5 mmol). The reaction mixture was stirred at room temperature for 2 h after which additional pyridine (3 ml) and benzylchloroformate (0.8 ml) was added at 0° C. The reaction mixture was then stirred at room temperature overnight, then diluted with dichloromethane (100 ml), washed successively with 1M aq. sulfuric acid (2×50 ml) and 1M aq. sodium hydrogen carbonate (1×50 ml), then dried (sodium sulfate), filtered and concentrated onto silica. Flash chromatography (diameter: 4 cm, YMC-gel: 50 g, packing eluent: ethyl acetate in petroleum ether 1:4) of the residue using ethyl acetate in petroleum ether 1:4 (350 ml), 2:3 (250 ml), 1:1 (250 ml), 3:2 (250 ml) and 3:1 (150 ml) gave compound 56 as a foamy syrup (2.71 g, 8.1 mmol, 62% over 2 steps) after drying in vacuum overnight.

NMR data (400 MHz, CDCl$_3$): $^1$H, 1.33, 1.52 (2 s, 6H, C(CH$_3$)$_2$), 2.34, (2 d, 1H, —OH), 3.04 (m, 1H, H-6a), 3.97 (m, 1H, H-6b), 4.19 (m, 1H, H-5), 4.33 (m,1H, H-3) 4.68, 4.84 (2 d, 1H, H-2), 4.79 (t, 1H, H-4), 5.08-5.24 (m, 2H, CH$_2$Ph), 5.86 (br s, 1H, H-1), 7.30-7.42 (m, 5H, Ar—H).

Step b)

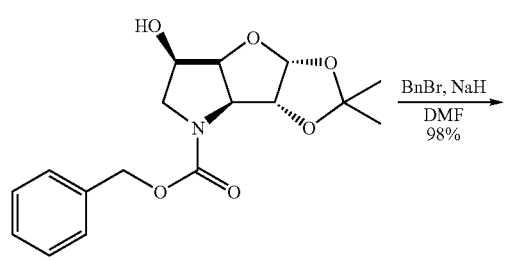

To a stirred suspension of sodium hydride (60% in mineral oil, Aldrich, 0.34 g, 8.4 mmol) and compound 56 (2.17 g, 6.47 mmol) in dimethylformamide (30 ml) was added benzyl bromide (0.81 mmol, 6.8 mmol) during 5 minutes. After stirring 1 h (TLC: ethyl acetate in petroleum ether 2:3), methanol (approx 2 ml) was added to destroy excess reagent, then immediately partitioned between ethyl acetate (180 ml) and water (150 ml). The organic layer was washed with water (3×100 ml), then dried (sodium sulfate), filtered and concentrated onto silica. Flash chromatography (diameter: 4 cm, YMC-gel: 40 g, packing eluent: ethyl acetate in petroleum ether 1:4) of the residue using ethyl acetate in petroleum ether 1:4 (100 ml), 3:7 (250 ml) and 2:3 (250 ml) gave a colourless syrup (2.7 g, 6.35 mmol, 98%) after drying in vacuum overnight.

NMR data (400 MHz, CDCl$_3$): $^1$H, 1.31 (s, 3H, C(CH$_3$)(CH$_3$)), 1.51 (d, 3H, C(CH$_3$)(CH$_3$)), 3.29 (m, 1H, H-6a), 3.78-3.96 (m, 2H, H-5 and H-6b), 4.22 (dd, 1H, H-3),4.64, 4.84 (2M, 4H, H-2, H-4 and CH$_2$Ph), 5.07-5.22 (m, 1H, CH$_2$Ph), 5.94 (m, 1H, H-1), 7.28-7.39 (m, 10H, Ar—H).

Step c)

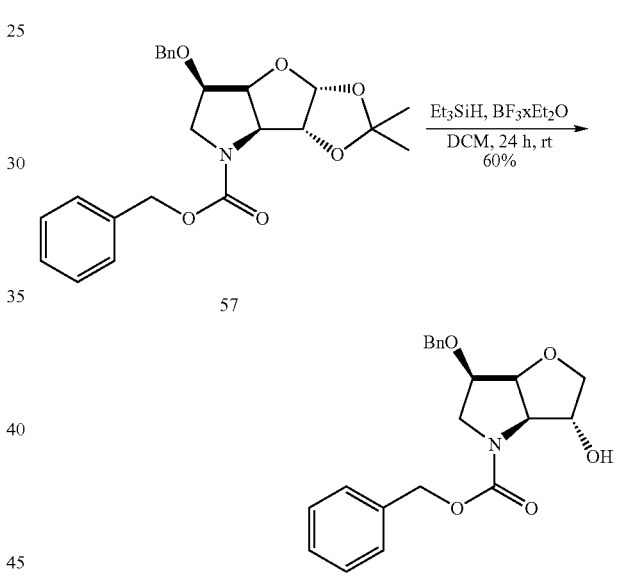

To a stirred solution of compound 7 (2.635 g, 6.19 mmol) in dichloromethane (28 ml) and triethyl silane (9.9 ml, 61.9 mmol) at 0° C. was added borontrifluoride etherate (7.9 ml, 61.9 mmol) in one portion. The reaction mixture was then stirred at rt for 24 h (TLC: petroleum ether-ethyl acetate 4:1 and ethyl acetate-toluene 3:2), then 1M aq. sodium hydrogen carbonate (40 ml) and some solid sodium hydrogen carbonate was carefully added until bubbling stopped. The resulting mixture was partitioned between dichloromethane (100 ml) and water (100 ml). The organic layer was washed with 1M aq. sodium hydrogen carbonate (1×100 ml) and brine (1×100 ml), then dried (sodium sulfate), filtered and concentrated onto silica. Flash chromatography (diameter: 4 cm, YMC-gel: 48 g, packing eluent: ethyl acetate-toluene 3:2) of the residue using ethyl acetate in toluene 3:2 (750 ml) gave a colorless hard syrup (1.38 g, 3.74 mmol, 60%) of about 85-90% purity according to TLC. LR-MS: Calcd for C$_{21}$H$_{24}$NO$_6$: 370.2. Found: 370.0 [M+H].

Step d)

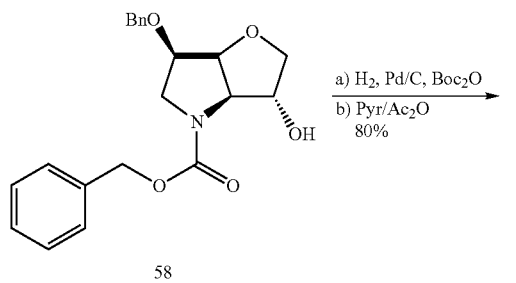

58

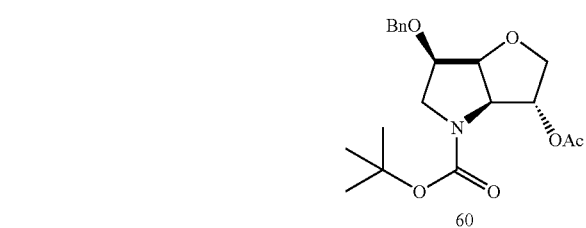

60

A mixture of compound 58 (1.38 g, 3.74 mmol), palladium-on-carbon (Acros, 10%, 0.12 g) and di-tert-butyl-dicarbonate (0.82 g, 3.7 mmol) in ethyl acetate (50 ml) was hydrogenated at slight overpressure. The hydrogen was changed 2 times over a period of 1 h and the reaction was monitored by LC-MS. After 1 h, additional palladium-on-carbon (0.1 g) was added and the reaction mixture was treated with hydrogen for 1 more hour. The reaction mixture was then filtered through Celite and concentrated. The residue was treated with 2:1 pyridine-acetic anhydride (18 ml) overnight, and then concentrated. The residue was redissolved in dichloromethane (60 ml) and was washed successively with 1M aq. sulfuric acid (2×40 ml) and 1M aq. sodium hydrogen carbonate (1×40 ml), and then dried (sodium sulfate) filtered and concentrated. Flash chromatography (diameter 3 cm, YMC-gel: 20 g, packing eluent ethyl acetate in toluene 1:4) of the residue (dissolved in toluene-ethyl acetate 4:1) using ethyl acetate in toluene 1:4 (200 ml) and 1:3 (150 ml) gave a colourless syrup (1.13 g, 3.0 mmol, 80%) after drying in vacuum overnight.

NMR data (400 MHz, CDCl$_3$): $^1$H, 1.45 (s, 9H, C(CH$_3$)$_3$), 2.08 (s, 3H, COCH$_3$), 3.10 (m, 1H, H-6a), 3.74-3.99 (m, 3H, H-1a, H-5 and H-6b), 4.11 (m, 1H, H-1b), 4.16-4.74 (m, 4H H-3, H-4 and CH$_2$Ph), 5.31 (m, 1H, H-2), 7.28-7.40 (m, 5H, Ar—H).

Step e)

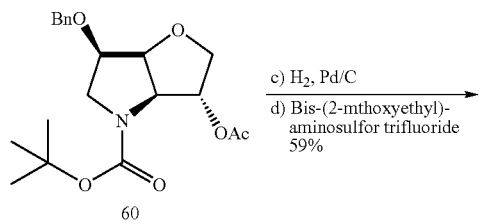

60

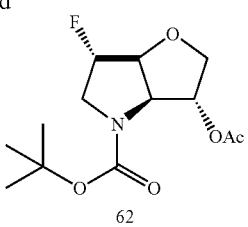

62

A mixture of compound 60 (1.08 g, 2.86 mmol) and palladium-on-carbon (10%, 0.15 g) in ethyl acetate (30 ml) was hydrogenated at slight over pressure for 2 h (TLC: toluene-ethyl acetate 4:1 and 1:1), then filtered through Celite and concentrated. The mixture was concentrated from dichloromethane (3×10 ml), then dissolved in dichloromethane and to the solution was added bis-(2-methoxyethyl)aminosulphur trifluoride (50% in THF, 2.12 ml, 2 eq.) at 0° C. After stirring at rt overnight additional bis(2-methoxyethyl)aminosulphur trifluoride (50% in THF, 2 ml) was added and the reaction mixture was stirred at rt for another night (TLC: toluene-ethyl acetate 1:1, ninhydrine staining), then 1M aq. sodium hydrogen carbonate was added carefully until bubbling stopped. The resulting mixture was diluted with dichloromethane (50 ml), and the organic layer was washed once with 1M aq. sodium hydrogen carbonate (40 ml), then dried (sodium sulfate), filtered and concentrated. Flash chromatography (diameter 3 cm, Silica: 25 g, packing eluent: toluene-ethyl acetate 4:1) of the residue (dissolved in toluene-ethyl acetate 4:1) using toluene-ethyl acetate 4:1 gave compound 62 (0.49 g, 1.7 mmol, 59%) as a colourless syrup after drying in vacuum overnight. Some starting material and sulphur intermediate could be recovered from the reaction mixture.

LR-MS: Calcd for C$_9$H$_{13}$FNO$_5$: 234.1. Found: 234.0 [M+2H-t-Butyl].

Example 2

Elongation with a Typical P2

Step a)

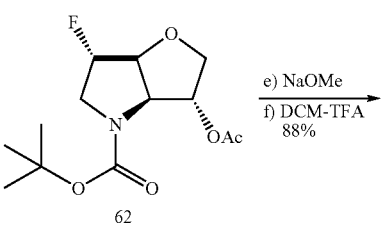

62

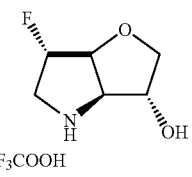

64

To a solution of compound 62 (0.49 g, 1.7 mmol) in methanol (9.5 ml) was added 0.5 M methanolic sodium methoxide (1 ml), then stirred at rt for 30 min (TLC: Toluene-ethyl acetate 3:2, ninhydrine staining). Methanol washed Dowex W X 8 (50-100 mesh, H$^+$-form) was carefully added (pH was monitored by pH-paper) was added until neutral, then the mixture was filtered and concentrated. The residue was dissolved in dichloromethane and trifluoroacetic acid was added at 0° C. The reaction mixture was then stirred at rt for 55 min (TLC: dichloromethane-methanol 9:1, ninhydrine staining), then concentrated. Column chromatography (diameter 2 cm, silica: 15 g, packing eluent dichloromethane-methanol 95:5) of the residue (dissolved in dichloromethane-methanol 95:5) using methanol in dichloromethane 5:95 (150 ml), 7:93 (100 ml) and 1:9 (200 ml) gave a hard syrup which crystallized upon standing (0.39 g, 1.50 mmol, 88%).

NMR data (400 MHz, DMSO-d6): $^1$H, 3.34, 3.44 (2 dd, 1H, H-6a), 3.60-3.70 (m, 2H, H-1a and H-6b), 3.89 (dd, 1H, H-1b), 4.15 (d, 1H, H-3), 4.51 (br s, 1H, H-2), 4.76 (dd, 1H, H-4), 5.26 (dd, $^2J_{H,F}$=48.3 Hz, H-5).

Step b)

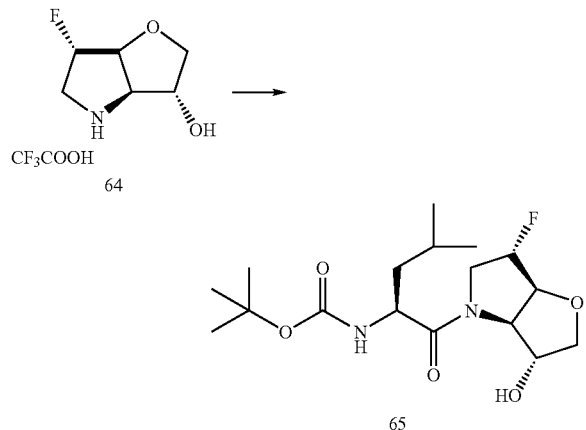

To a stirred solution of compound 64 (0.34 g, 1.30 mmol), N-ethyl-N'-(3-dimethylaminopropyl)carbodiimide hydrochloride (0.28 g, 1.43 mmol), 1-hydroxybenzotriazole hydrate (0.22 g) and N-(tert-Butoxycarbonyl)-L-leucine monohydrate (0.34 g, 1.37 mmol) in DMF (10 ml) was added triethylamine (0.54 ml, 3.9 mmol), then stirred at rt for 24 h. The reaction mixture was the partitioned between 10% aq. citric acid (30 ml) and ethyl acetate (10 ml). The water layer was extracted with ethyl acetate (3×10 ml), then the organic layers were combined, and washed successively with water (1×20 ml) and 1M aq. sodium hydrogen carbonate (3×20 ml), then dried (sodium sulfate), filtered and concentrated onto silica. Flash chromatography with ethyl acetate in petroleum ether (40-60%, stepwise gradient elution) of the residue gave 15 (0.35 g, 0.98 mmol, 75%) as a coloudess amorphous solid.

LR-MS: Calcd for $C_{13}H_{22}FN_2O_5$: 305.1. Found: 305.1 [M+2H-t-Butyl].

Example 3

Elongation with a Typical P3

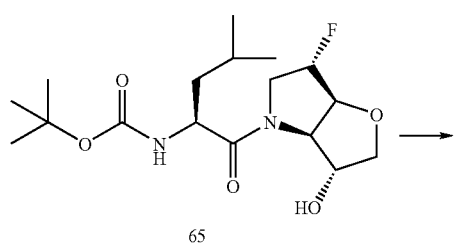

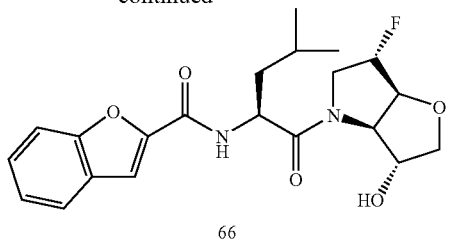

To a solution of compound 65 (0.11 g, 0.31 mmol) in dichloromethane (2 ml) at 0° C. was added trifluoroacetic acid (2 ml), then stirred at rt for 45 min. The reaction mixture was then concentrated and co-concentrated with toluene. To a suspension of the residue, N-ethyl-N'-(3-dimethylaminopropyl)carbodiimide hydrochloride (0.064 g, 0.34 mmol), 1-Hydroxybenzotriazole hydrate (0.051 g) and benzo[b]furan-2-carboxylic acid (0.052 g, 0.32 mmol) in DMF (3 ml) was added triethylamine (0.13 ml, 0.9 mmol), then stirred at rt for 24 h. The reaction mixture was then concentrated. The residue was then partitioned between 10% aq. citric acid (30 ml) and ethyl acetate (10 ml). The water layer was extracted with ethyl acetate (2×10 ml), then the organic layers were combined, and washed successively with water (1×10 ml) and 1M aq. sodium hydrogen carbonate (3×10 ml), then dried (sodium sulfate), filtered and concentrated onto silica. Flash chromatography with ethyl acetate in petroleum ether (50-60%, stepwise gradient elution) of the residue gave 66 (0.11 g, 0.27 mmol, 89%) as a colourless glassy solid.

LR-MS: Calcd for $C_{21}H_{26}FN_2O_5$: 405.2. Found: 405.1 [M+H].

Example 4

Oxidation to P1 Ketone

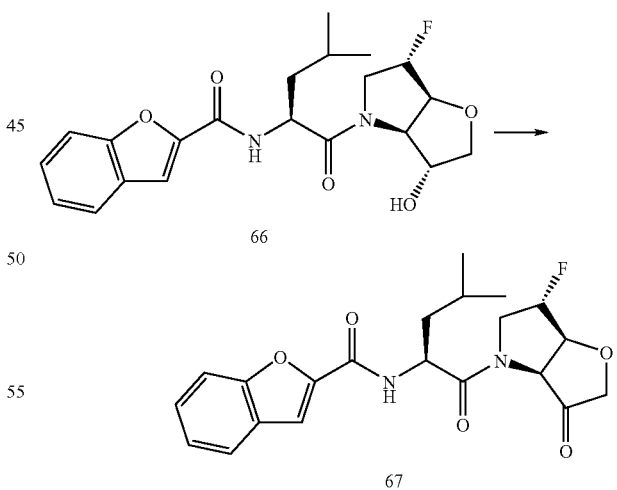

To a stirred solution of compound 66 (0.10 g, 0.25 mmol) in dichloromethane (4 ml) at rt was added Dess-Martin periodinane (0.12 g, 0.28 mmol). After stirring for 90 minutes the reaction mixture was diluted with dichloromethane (10 ml), washed with 1:1 1M aq. sodium hydrogen carbonate-10% aq. sodiumthiosulfate (4×10 ml), then dried (sodium sulfate), filtered and concentrated onto silica. Flash chromatography with ethyl acetate in petroleum ether (50-60%, stepwise gradient elution) of the residue gave 67 (0.072 g, 0.18 mmol, 71%) as a colourless foam. Compound 67 is obtained as a mixture of geometrical isomers (rotamers) and their hydrates.

LR-MS: Calcd for $C_{21}H_{24}FN_2O_5$: 403.2. Found: 403.0 [M+H]. A NMR sample of the ketoforms of 67 was obtained as follows; 5 mg of compound 67 (mixture of geometrical isomers and hydrate forms with the ratio: hydrate/keto 6:4) was dissolved in DMSO-d6, then heated up to 100° C. in the NMR apparatus and then allowed to reach 50° C. upon which NMR indicated only trace amounts of the hydrate forms and the ratio of the rotamers were 2:1.

NMR data (500 MHz, DMSO-d6, 50° C.): $^1$H, 0.90-1.04 (m, 4×CH$_3$, major and minor forms), 1.39-1.82 (m, 2×CH$_2$CH(CH$_3$)$_2$ and 2×CH$_2$CH(CH$_3$)$_2$, major and minor forms), 3.56 (m, H-6a, minor), 3.82 (m, H-6A, major), 3.97-4.25 (m, 4×H-1, major and minor forms and H-6b, minor), 4.37 (dd, H-6b, major), 4.62 (d, H-3, minor), 4.79 (m, H, major), 4.84 (d, H-3, major), 4.94 (m, H-4, major), 5.12 (m, H-4, minor), 5.15-5.34 (m, H-5 major and H-5 minor, H minor, $J_{H,F\ major}$=49.1 Hz, $J_{H,F\ minor}$=49.4 Hz), 7.35 (t, 1H, Ar—H), 7.47 (t, 1H, Ar—H), 7.57-7.70 (m, 2H, Ar—H), 7.78 (d, 1H, Ar—H), 8.18 (d, —NH, minor), 8.70 (d, —NH, major).

Example 5

An Alternative P3

Step a)

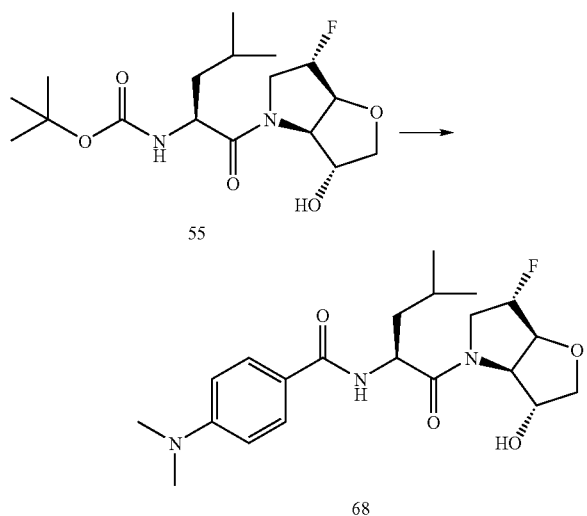

To a solution of compound 55 (0.11 g, 0.32 mmol) in dichloromethane (2 ml) at 0° C. was added trifluoroacetic acid (2 ml). After stirring for 45 min at rt (TLC: petroleum ether-ethyl acetate 1:1 and ethyl acetate-methanol-acetic acid-water 40:3:3:2), the reaction mixture was concentrated and co-concentrated from toluene (3×5 ml). To a suspension of the residue, 4-(dimethylamino)benzoic acid (0.055 g, 0.33 mmol), N-ethyl-N'-(3-dimethylaminopropyl)carbodiimide hydrochloride (0.067 g, 0.35 mmol) and 1-hydroxybenzotriazole hydrate (0.053 g) in DMF (3 ml) was added triethylamine (0.13 ml, 0.95 mmol) then stirred at rt overnight (TLC: petroleum ether-ethyl acetate 2:3 and ethyl acetate-methanol-acetic acid-water 40:3:3:2). The reaction mixture was then concentrated, partitioned between 8% aq. KH$_2$PO$_4$ (30 ml) and ethyl acetate (10 ml). The water layer was extracted with ethyl acetate (3×10 ml), and the combined organic layers were washed with water (1×10 ml) and 1M aq. sodium hydrogen carbonate (3×10 ml), then dried (sodium sulphate), filtered and concentrated. The residue was redissolved in dichloromethane and concentrated onto silica. Flash chromatography (diameter: 2 cm, Silica: 8 g, packing eluent petroleum ether-ethyl acetate 1:1) of the residue (stepwise gradient elution, ethyl acetate in petroleum ether 50-100%) gave a colourless foam (0.10 g, 0.25 mmol, 80%).

LR-MS: Calcd for $C_{21}H_{31}FN_3O_4$: 408.2. Found: 408.1 [M+H].

Step b)

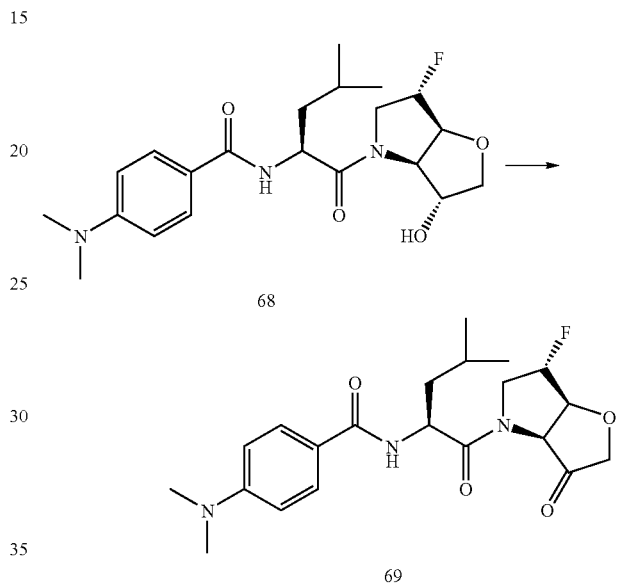

To a stirred solution of the mono-ol 68 (0.096 g, 0.24 mol) in dichloromethane at rt was added Dess-Martin periodinane (0.11 g, 0.26 mmol). The reaction mixture turned red and after stirring for approximately 35 min (TLC: petroleum ether-ethyl acetate 2:3), the reaction mixture was diluted with dichloromethane (10 ml), washed with 1:1 1M aq. sodium hydrogen carbonate-10% aq. sodiumthiosulfate (4×10 ml), then dried (sodium sulfate), filtered and concentrated onto silica. Flash chromatography (diameter 2 cm, Silica: 7 g, Packing eluent petroleum ether-ethyl acetate 1:1) of the residue (stepwise gradient elution, ethyl acetate in petroleum ether 50-100%) gave a coloudess foam (0.039 g, 0.10 mmol, 41%).

LR-MS: Calcd for $C_{21}H_{27}FN_3O_4$: 404.2. Found: 404.1 [M−H].

Example 6

An Alternative P3

Step a)

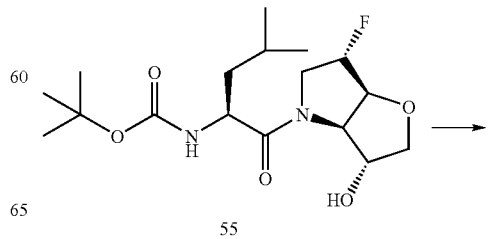

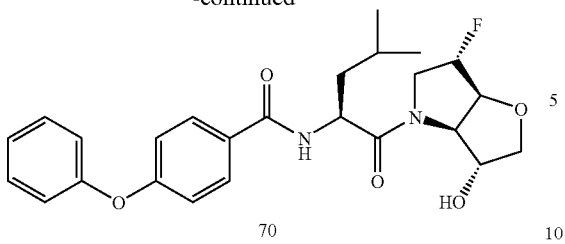

To a solution of compound 55 (0.12 g, 0.32 mmol) in dichloromethane (2 ml) at 0° C. was added trifluoroacetic acid (2 ml), then stirred at rt for 45 min. The reaction mixture was then concentrated and co-concentrated with toluene (3×5 ml). To a suspension of the residue, N-ethyl-N'-(3-dimethylaminopropyl) carbodiimide hydrochloride (0.068 g, 0.36 mmol), 1-hydroxybenzotriazole hydrate (0.055 g) and 4-phenoxybenzoic acid (0.073 g, 0.34 mmol) in DMF (3 ml) was added triethylamine (0.14 ml, 0.97 mmol), then stirred at rt for 24 h. The reaction mixture was then concentrated. The residue was then partitioned between 10% aq. citric acid (30 ml) and ethyl acetate (10 ml). The water layer was extracted with ethyl acetate (2×10 ml), then the organic layers were combined, and washed successively with water (1×10 ml) and 1M aq. sodium hydrogen carbonate (3×10 ml), then dried (sodium sulfate), filtered and concentrated onto silica. Flash chromatography of the residue with 1:1 ethyl acetate in petroleum ether gave colourless hard syrup (0.14 g, 0.30 mmol, 91%).

LR-MS: Calcd for $C_{25}H_{30}FN_2O_5$: 457.2. Found: 4572 [M+H].

Step b)

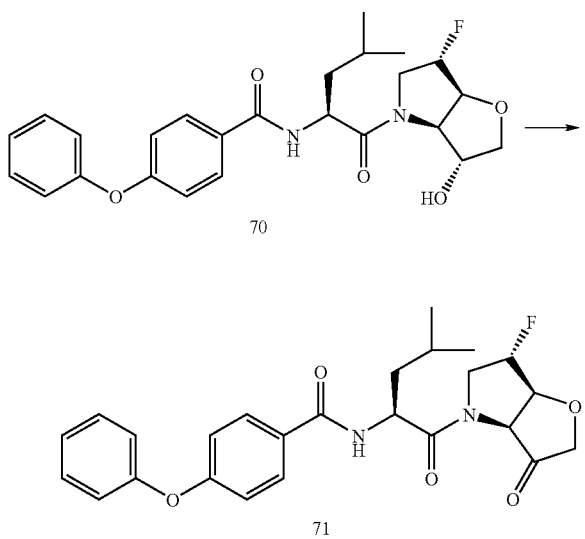

To a stirred solution of the mono-ol (0.128 g, 0.28 mmol) in dichloromethane (4 ml) at rt was added Dess-Martin periodinane (0.12 g, 0.28 mmol). After stirring for 90 minutes the reaction mixture was diluted with dichloromethane (10 ml), washed with 1:1 1M aq. sodium hydrogen carbonate-10% aq. sodiumthiosulfate (4×10 ml), then dried (sodium sulfate), filtered and concentrated onto silica. Flash chromatography with ethyl acetate in petroleum ether (50-60%, stepwise gradient elution) of the residue gave 71 (0.072 g, 0.18 mmol, 71%) as a colourless foam.

LR-MS: Calcd for $C_{21}H_{28}FN_2O_5$: 455.2. Found: 455.1 [M+H].

Example 7

An Alternative P1 Epimer

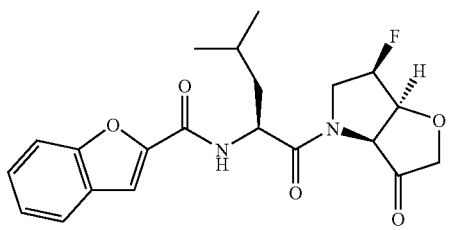

Step a)

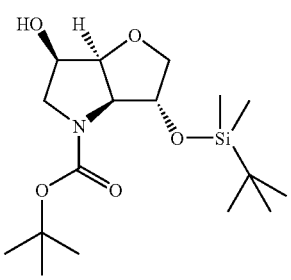

To a stirred solution of compound (60) (1.58 g, 4.19 mmol) in methanol (20 mL) was added a solution of 0.5 M sodium methoxide in methanol (5 mL) at room temperature, then stirred for 40 min. The reaction mixture was then neutralized with Dowex 50 WX 8 (H$^+$-form), filtered, added triethylamine until slight alkaline, then concentrated and concentrated from toluene (2×20 mL). To a stirred solution of the residue and imidazole (0.43 g, 6.28 mmol) in DMF (10 mL) at 0° C. was added tert-Butyldimethylchlorosilane (0.76 g, 5.02 mmol), then stirred at room temperature overnight. The reaction mixture was then diluted with ethyl acetate (100 mL), washed successively with 10% aq. citric acid (3×50 mL) and 1M aq. sodium hydrogen carbonate (3×50 mL), dried (sodium sulphate), filtered and concentrated onto silica. Column chromatography (stepwise gradient elution, ethyl acetate in toluene, 5-20%) of the residue afforded the fully protected intermediate as a syrup (1.86 g). A mixture of palladium on charcoal (Aldrich 10%, 0.28 g) and the intermediate obtained above (1.80 g, 4.00 mmol) in ethyl acetate (40 mL) was hydrogenated at slight overpressure for 1 h, then filtered through celite and concentrated. The material crystallized upon drying in vacuum to afford 72 as needles (1.34 g, 90%).

NMR data (400 MHz, CDCl$_3$): $^1$H, delta 0.14 (m, 6H, Si(CH$_3$)$_2$), 0.90 (m, 9H, SiC(CH$_3$)$_3$), 1.48 (m, 9H, C(CH$_3$)$_3$), 2.53 (m, 1H, OH), 2.78 (dd, 1H, —H-6A), 3.67-4.05 (m, 3H, H-1A, H-1B and H-6B), 4.05-4.21 (m, 2H, H-3 and H-5), 4.35-4.50 (2 brs, 1H, H-2), 4.57 (m, 1H, H-4).

Step b)

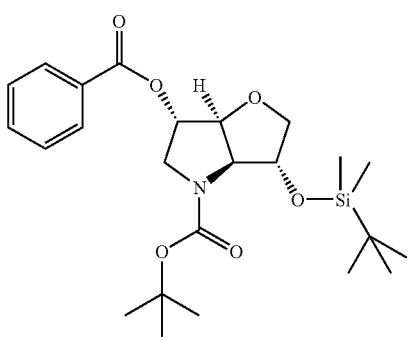

To a stirred solution of (72) (1.068 g, 2.97 mmol), benzoic acid (0.50 g, 4.46 mmol) and triphenylphosphine (1.17 g, 4.46 mmol) in THF (15 mL) at 0° C. was added dropwise a solution of diisopropyl azodicarboxylate (0.88 mL, 4.46 mmol) in THF (5 mL) during 20 minutes. The reaction mixture was then stirred at room temperature overnight, then concentrated onto silica. Flash chromatography of the residue using petroleum ether-ethyl acetate 9:1 as eluent, gave a colorless syrup (1.34 g, 97%).

NMR data (400 MHz, CDCl3): 1H, delta 0.08-0.21 (m, 6H, Si(CH$_3$)$_2$), 0.90 (s, 9H, SiC(CH$_3$)$_3$), 1.42-1.56 (m, 9H, C(CH$_3$)$_3$), 3.48 (m, 1H, H-6A), 3.70-4.01 (m, 3H, H-1A, H-1B, H-6B minor and major), 4.21, 4.30 (2d, 1H, H-3), 4.44, 4.56 (2 brs, 1H, H-2), 4.72 (m, 1H, H-4), 5.34 (d, 1H, H-5), 7.45 (t, 2H, Ar—H), 7.58 (t, 1H, Ar—H), 8.00 (d, 2H, Ar—H).

Step c)

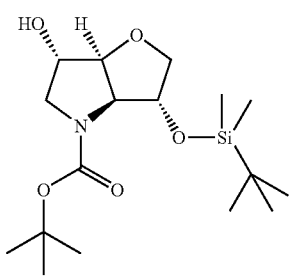

To a stirred solution of (73) (1.34 g, 2.89 mmol) in methanol (6 mL) was added a solution of 0.5 M sodium methoxide in methanol (6 mL) at room temperature, then stirred for 15 min. The reaction mixture was then neutralized with Dowex 50 WX 8 (H$^+$-form) and filtered. The obtained solution was added a solution obtained similarly as above starting from (II) (0.187 g, 0.40 mmol), then concentrated. Flash chromatography of the residue using toluene-ethyl acetate 3:2 as eluent gave 74 as a colorless syrup which crystallized upon drying in vacuum (1.091 g, 92%).

NMR data (400 MHz, CDCl3): 1H, delta 0.06-0.20 (m, 6H, Si(CH$_3$)$_2$), 0.89 (s, 9H, SiC(CH$_3$)$_3$), 1.42-1.54 (m, 9H, C(CH$_3$)$_3$), 2.03 (brs, 1H, OH), 3.28 (dd, 1H, H-6A), 3.53-3.79 (m, 3H, H-1A, H-1B, H-6B), 4.19 and 4.34-4.56 (2 m, 4H, H-2, H-3, H-4 and H-5).

Step d)

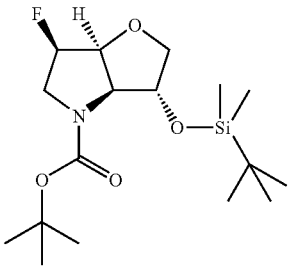

To a stirred solution of (74) (0.428 g, 1.19 mmol) in dichloromethane (10 mL) in a Teflon coated flask was added Deoxofluor (50% in THF, 0.53 mL) at room temperature resulting in a slight temperature increase. The reaction mixture was stirred at room temperature for 72 h, then diluted with dichloromethane (20 mL), washed with 1M aq. sodium hydrogen carbonate (2×20 mL), dried (sodium sulphate), filtered and concentrated onto silica. Flash chromatography of the residue using petroleum ether-ethyl acetate 9:1 as eluent gave (IV) as a colorless oil (0.118 g, 27%).

NMR data (400 MHz, CDCl3): 1H, delta 0.08-0.20 (m, 6H, Si(CH$_3$)$_2$), 0.89 (s, 9H, SiC(CH$_3$)$_3$), 1.42-1.53 (m, 9H, C(CH$_3$)$_3$), 3.26 and 3.36 (2 dd, 1H, H-6A), 3.64 (m, 1H, H-1A), 3.73-4.04 (m, 3H, H-1B, H-6B), 4.20 (dd, 1H, H-3*), 4.40, 4.51 (2 s, 1H, H-2), 4.69 (m, 1H, H-4*) 4.86, 4.98 (2 brs, 1H, H-5). * Could be interchanged.

Step e)

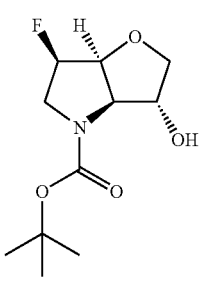

To a stirred solution of (75) (0.229 g, 0.63 mmol) in THF (8 mL) was added 1M tetrabutylammonium fluoride in THF (0.70 mL), then stirred at room temperature for 40 min. The reaction mixture was then concentrated onto silica. Column chromatography of the residue using toluene-ethyl acetate 1:1 as eluent gave 75 as a colorless hard syrup (0.150 g, 96%).

NMR data (400 MHz, CDCl3): 1H, delta 1.46 1.53 (m, 9H, C(CH$_3$)$_3$), 2.70 (d, 0.3H, OH-minor), 3.26-3.46 (m, 1.7H, H-6A and OH-major), 3.75-4.04 (m, 3H, H-1A, H-1B and H-6B), 4.29, 4.34 (2d, 1H, H-3* minor and major), 4.43, 4.50 (2 brs, 1H, H-2 minor and major), 4.74 (m, 1H, H-4*), 4.89, 5.02 (2 brs, 1H, H-5).

Step f)

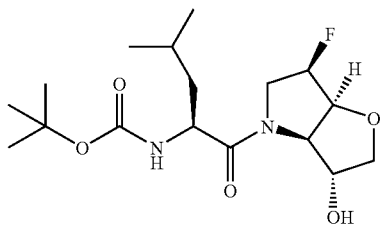
76

To a solution of (75) (0.099 g, 0.40 mmol) in dichloromethane (2 mL) at 0° C., was added trifluoroacetic acid (2 mL), then stirred at room temperature for 35 min, then concentrated and concentrated from toluene (3×5 mL). To a suspension of the residue, 1-hydroxybenzotrazole hydrate (0.067 g, 0.44 mmol), N-ethyl-N'-(3-dimethylaminopropyl)carbodiimide×HCl (0.084 g, 0.44 mmol) and N-(tert-Butoxycarbonyl)-L-leucine monohydrate (0.105 g, 0.42 mmol) in DMF (4 mL) was added triethylamine (0.17 mL, 1.2 mmol), then stirred at room temperature overnight. The reaction was then concentrated into half the volume, diluted with ethyl acetate (25 mL), washed successively with 10% aq. citric acid (3×15mL), and 1M aq. sodium hydrogen carbonate (3×15 mL), dried (sodium sulphate), filtered and concentrated. Column chromatography of the residue using ethyl acetate-toluene 3:2 afforded (76) as a colorless hard syrup (0.137 g, 95%).

NMR data (400 MHz, CDCl3, selected signals): 1H, delta 0.89–1.01 (m, 6H, C(CH)$_2$), 4.98, 5.07 (2 dd, 1H, H-5major and H-5 minor).

LR-MS: Calcd for $C_{17}H_{30}FN_2O_5$: 361.2. Found: 361.1 [M+H].

Step g)

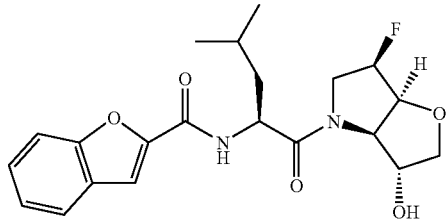
77

To a solution of (76) (0.137 g, 0.38 mmol) in dichloromethane at 0° C. was added TFA, then stirred at room temperature for 30 min, then concentrated and concentrated from toluene (3×5 mL). To a suspension of the residue, 1-hydroxybenzotrazole hydrate (0.064 g, 0.42 mmol), N-ethyl-N'-(3-dimethylaminopropyl)carbodiimide×HCl (0.080 g, 0.42 mmol) and benzo[b]furan-2-carboxylic acid (0.065 g, 0.40 mmol) in DMF (3 mL) was added triethylamine (0.16 mL, 1.2 mmol), then stirred at room temperature overnight. The The reaction was then concentrated into half the volume, diluted with ethyl acetate (25 mL), washed successively with 10% aq. citric acid (3×15mL), and 1M aq. sodium hydrogen carbonate (3×15 mL), dried (sodium sulphate), filtered and concentrated. Column chromatography of the residue using ethyl acetate-toluene 3:2 afforded (77) as a colorless hard syrup (0.148 g, 96%).

LR-MS: Calcd for $C_{21}H_{26}FN_2O_5$: 405.2. Found: 405.1 [M+H].

Step h)

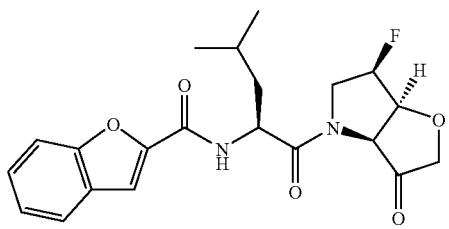
78

To a stirred solution of (77) (0.148 g, 0.37 mmol) in dichloromethane at room temperature was added Dess-Martin periodinane (0.171 g, 0.40 mmol). After stirring for 2 h, the reaction mixture was diluted with dichloromethane (20 mL), then washed with 1:1 1M aq. sodium hydrogen carbonate/ 10% aq. sodium thiosulphate (3×12 mL), dried (sodium sulphate), filtered and concentrated. Column chromatography of the residue (stepwise gradient elution, ethyl acetate in toluene, 40-50%) afforded (VIII) as a colorless foam (0.105 g, 71%).

NMR data (100 MHz, CDCl$_3$, selected signals): $^{13}$C, delta 206.7 and 206.5 (C=O major and minor).

LR-MS: Calcd for $C_{21}H_{24}FN_2O_5$,: 403.2. Found: 403.1 [M+H].

Example 8

Additional Cathepsin K Inhibitors

Compounds 8.1-8.13 & 8.15-820 depicted in the table below were synthesised by successively coupling the N-protected P2 and P3 acids itemised in the table, to the P1 building block of Example 1 using the solid phase methodology outlined below. Compound 8.14 was synthesised in solution phase as outlined below. The construction of P2 and P3 building blocks not readily accessible from commercial sources appears below.

TABLE 1

| No. | Structure | P2 | P3 building block | MS data |
|---|---|---|---|---|
| 8.1 | 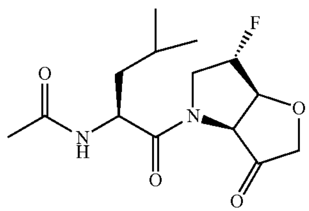 | A | Ac₂O | 301 [M + H]⁺ |
| 8.2 | 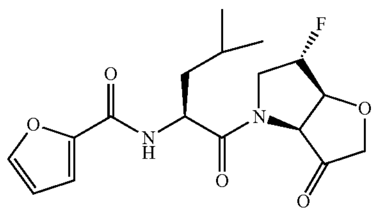 | A | furan-2-carboxylic acid | 353 [M + H]⁺ |
| 8.3 | 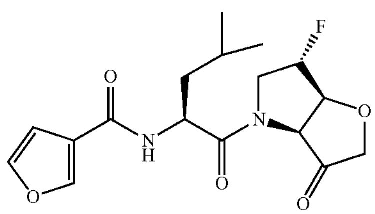 | A | furan-3-carboxylic acid | 353 [M + H]⁺ |
| 8.4 | 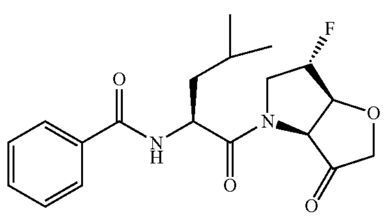 | A | benzoic acid | 363 [M + H]⁺ |

TABLE 1-continued

| No. | Structure | P2 | P3 building block | MS data |
|---|---|---|---|---|
| 8.5 | 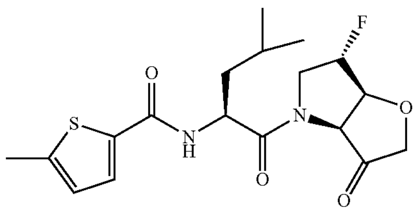 | A | | 383 [M + H]$^+$ |
| 8.6 | 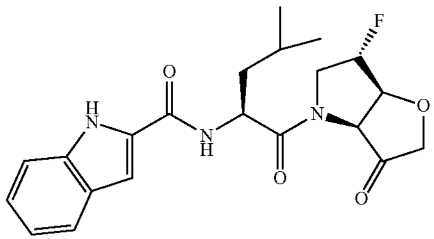 | A | | 402 [M + H]$^+$ |
| 8.7 | 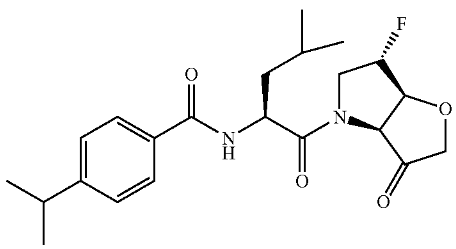 | A | | 405 [M + H]$^+$ |
| 8.8 | 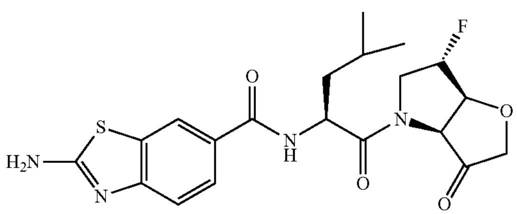 | A | | 416 [M + H]$^+$ |

TABLE 1-continued

| No. | Structure | P2 | P3 building block | MS data |
|---|---|---|---|---|
| 8.9 | 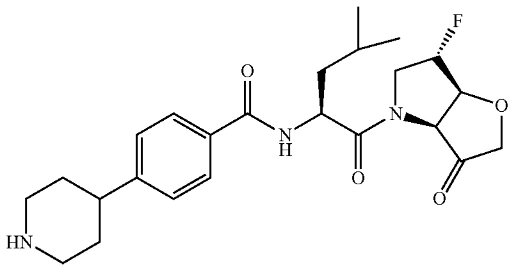 | A | | 419 [M + H]+ |
| 8.10 | 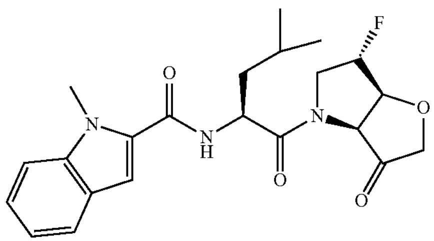 | A | | 420 [M + H]+ |
| 8.11 | 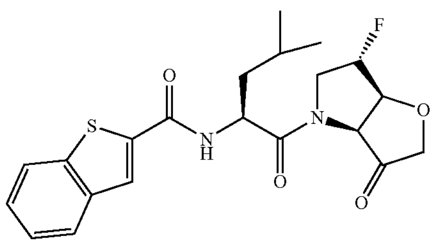 | A | | 433 [M + H]+ |
| 8.12 | 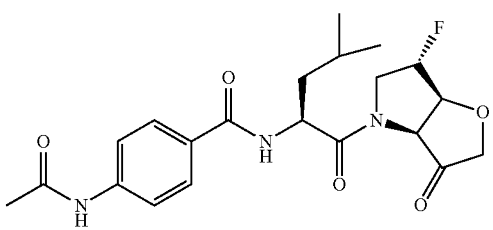 | A | | 435 [M + H]+ 453 [M + 18]+ |

TABLE 1-continued

| No. | Structure | P2 | P3 building block | MS data |
|---|---|---|---|---|
| 8.13 | 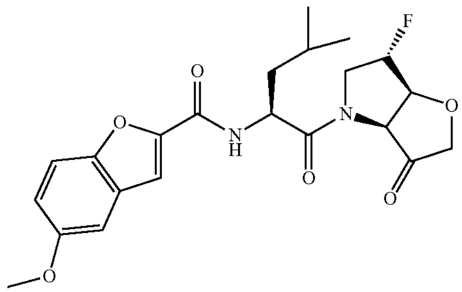 | A | 5-methoxybenzofuran-2-carboxylic acid | 464 [M + H]+ |
| 8.14 | 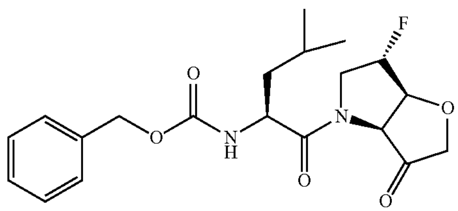 | B | — | 393 [M + H]+ |
| 8.15 | 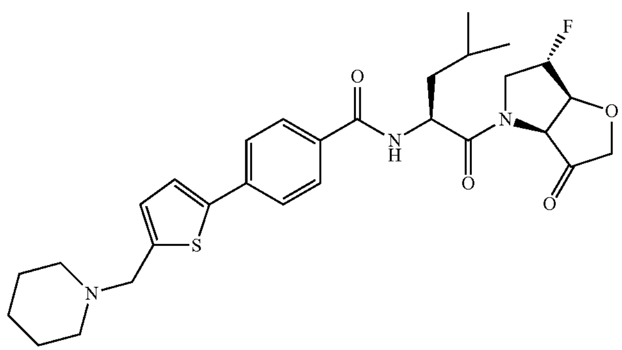 | A | 4-(5-(piperidin-1-ylmethyl)thiophen-2-yl)benzoic acid | 542 [M + H]+ 560 [M + 18]+ |

TABLE 1-continued

| No. | Structure | P2 | P3 building block | MS data |
|---|---|---|---|---|
| 8.16 | 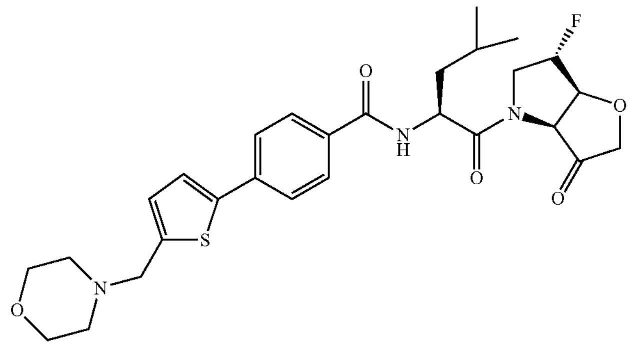 | A | | 544 [M + H]+ 562 [M + 18]+ |
| 8.17 | 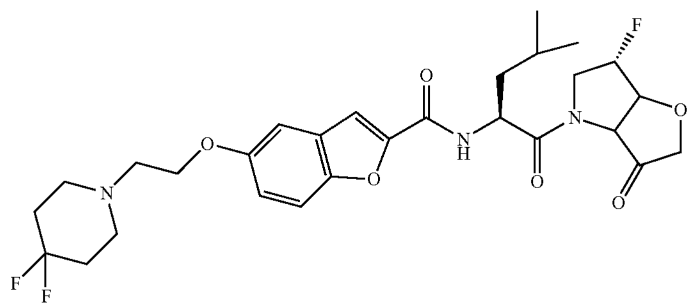 | A | | 566 [M + H]+ 584 [M + 18]+ |
| 8.18 | 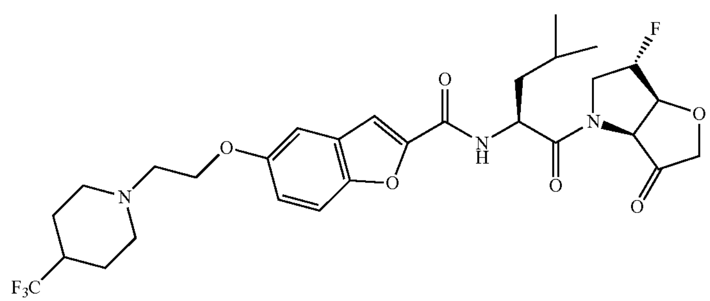 | A | | 598 [M + H]+ 616 [M + 18]+ |

TABLE 1-continued

| No. | Structure | P2 | P3 building block | MS data |
|---|---|---|---|---|
| 8.19 | 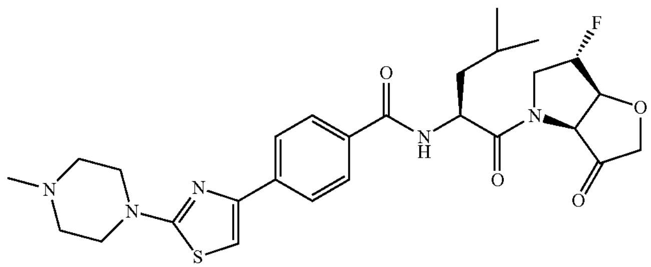 | A | | 545 [M + H]+ 563 [M + 18]+ |
| 8.20 | 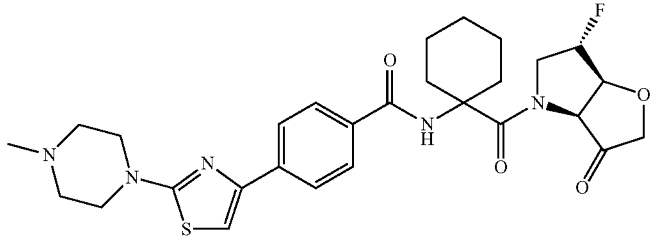 | C | | 556 [M + H]+ 574 [M + 18]+ |
| 8.21 | 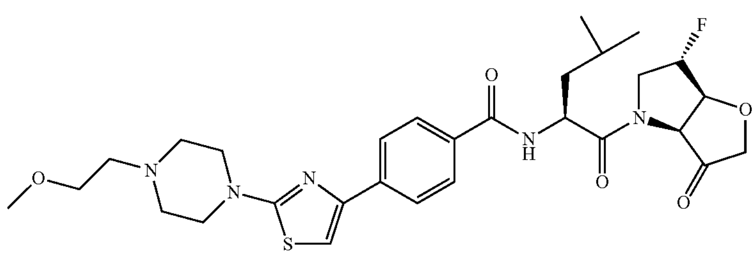 | A | | 588 [M + H]+ 606 [M + 18]+ |

TABLE 1-continued

| No. | Structure | P2 | P3 building block | MS data |
|---|---|---|---|---|
| 8.22 | 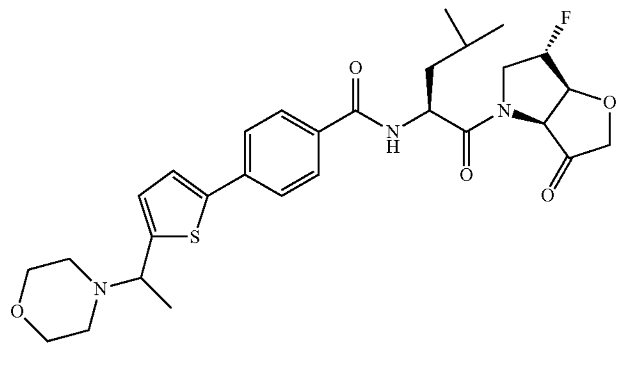 | A | | 489 [M + 18 − morpholine]+ 471 [M + H − morpholine]+ |
| 8.23 | 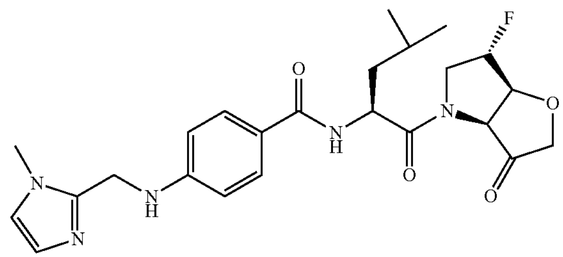 | A | | 472 [M + H]+ 490 [M + 18]+ |
| 8.24 | 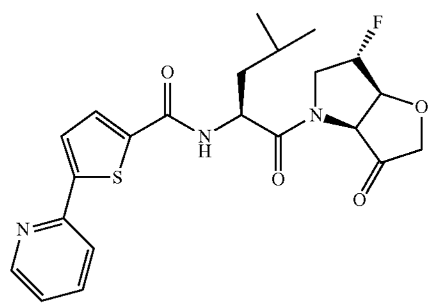 | A | | 446 [M + H]+ 464 [M + 18]+ |

TABLE 1-continued

| No. | Structure | P2 | P3 building block | MS data |
|---|---|---|---|---|
| 8.25 | 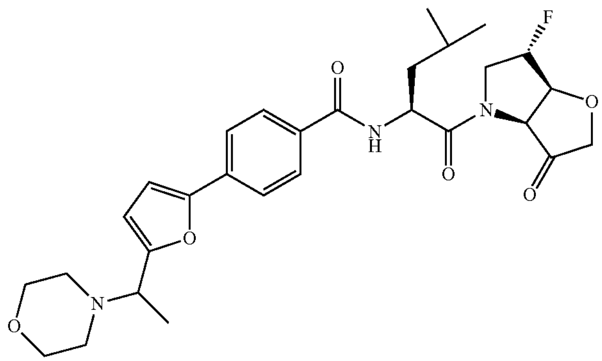 | A | | 560 [M + 18]+ 473 [M + H – morpholine]+ |
| 8.26 | 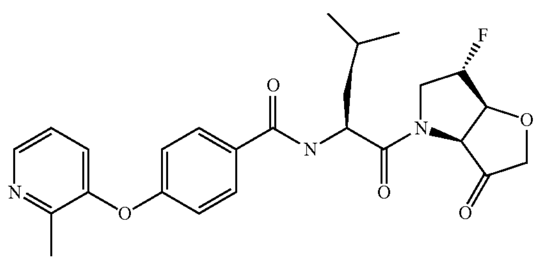 | A | | [M + H]+ 470 [M + 18]+ 488 |
| 8.27 | 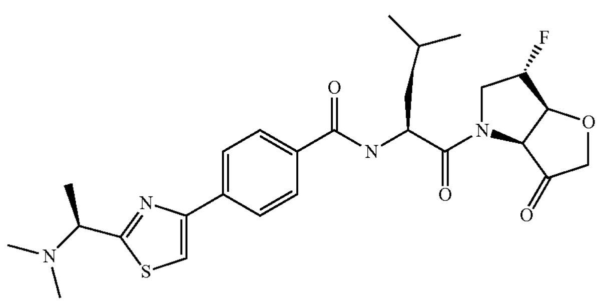 | A | | [M + H]+ 517 [M + 18]+ 488 |

TABLE 1-continued

| No. | Structure | P2 | P3 building block | MS data |
|---|---|---|---|---|
| 8.28 | 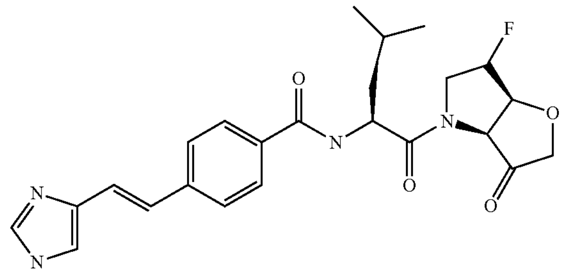 | A | | [M + H]+ 455 [M + 18]+ 473 |
| 8.29 | 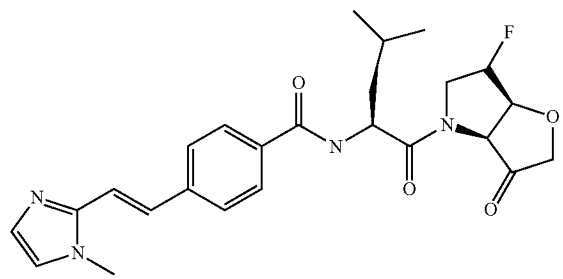 | A | | [M + H]+ 469 [M + 18]+ 487 |
| 8.30 | 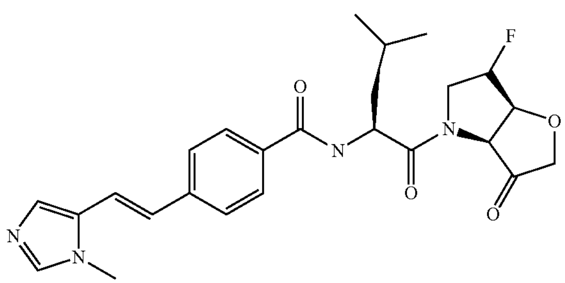 | A | | [M + H]+ 469 [M + 18]+ 487 |

TABLE 1-continued

| No. | Structure | P2 | P3 building block | MS data |
|---|---|---|---|---|
| 8.31 | 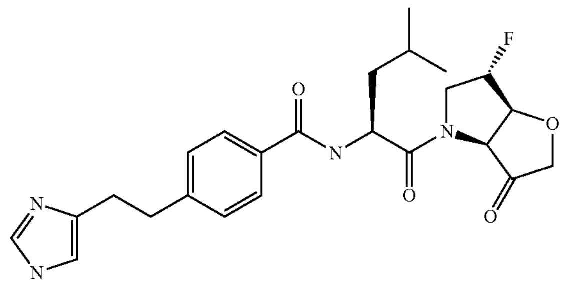 | A | | [M + H]+ 457<br>[M + 18]+ 475 |
| 8.32 | 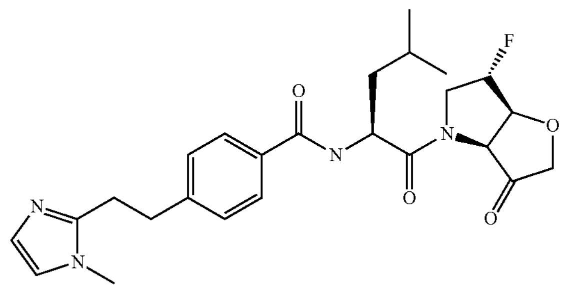 | A | | [M + H]+ 471<br>[M + 18]+ 489 |
| 8.33 | 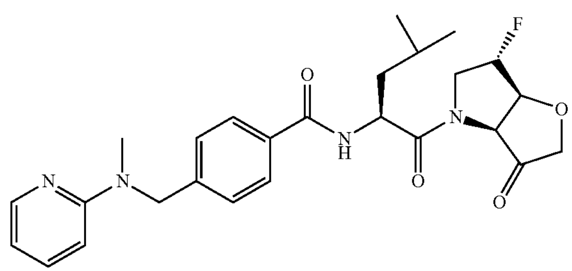 | A | | [M + H]+ 483<br>[M + 18]+ 501 |

TABLE 1-continued

| No. | Structure | P2 | P3 building block | MS data |
|---|---|---|---|---|
| 8.34 | 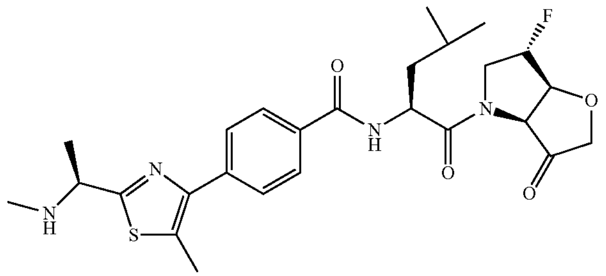 | A | | [M + H]+ 517 [M + 18]+ 535 |
| 8.35 | 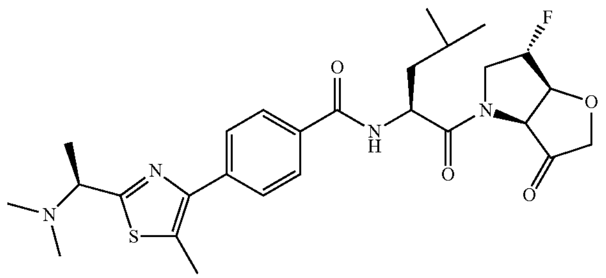 | A | | [M − H]− 529 [M + 18]+ 549 |
| 8.36 | 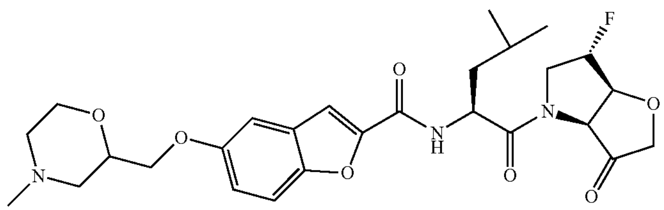 | A | | [M + H]+ 532 [M + 18]+ 550 |
| 8.37 | 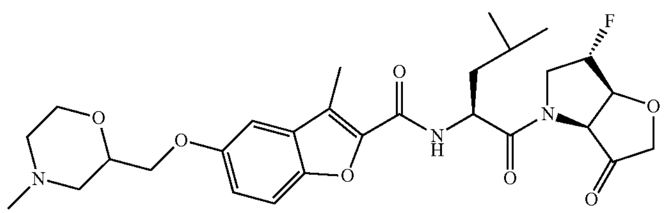 | A | | [M + H]+ 546 [M + 18]+ 564 |

TABLE 1-continued

| No. | Structure | P2 | P3 building block | MS data |
|---|---|---|---|---|
| 8.38 | 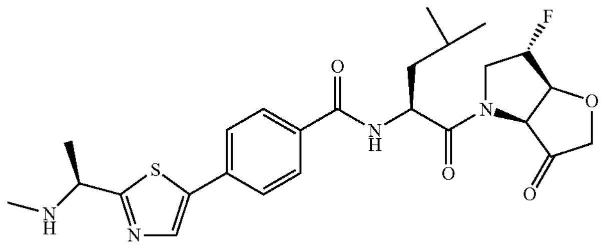 | A | | [M+H]+ 504 [M+18]+ 521 |
| 8.39 | 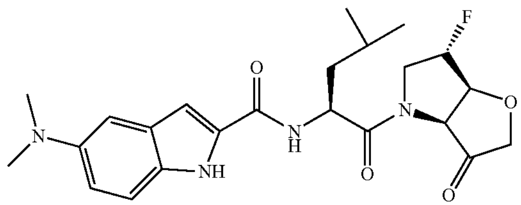 | A | | [M+H]+ 445 [M+18]+ 463 |
| 8.40 | 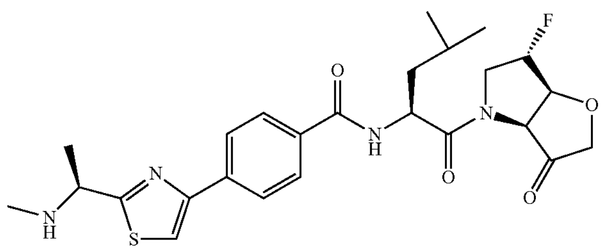 | A | | [M+H]+ 503 [M+18]+ 521 |
| 8.41 | 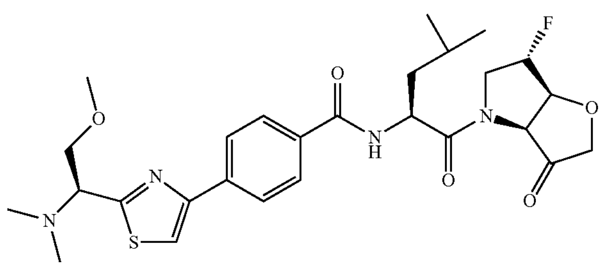 | A | | [M+H]+ 533 [M+18]+ 551 |

TABLE 1-continued

| No. | Structure | P2 | P3 building block | MS data |
|---|---|---|---|---|
| 8.42 | 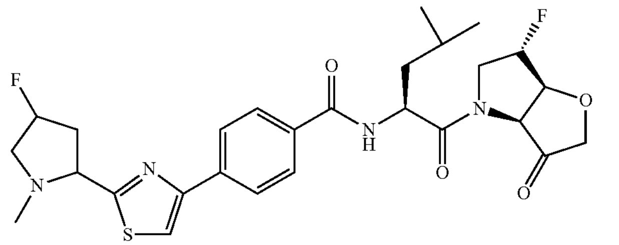 | A | | [M + H]⁺ 547<br>[M + 18]⁺ 565 |
| 8.43 | 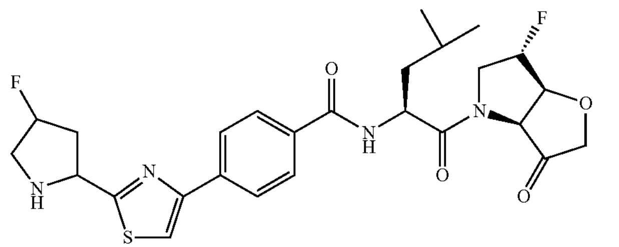 | A | | [M + H]⁺ 532<br>[M + 18]⁺ 550 |
| 8.44 | 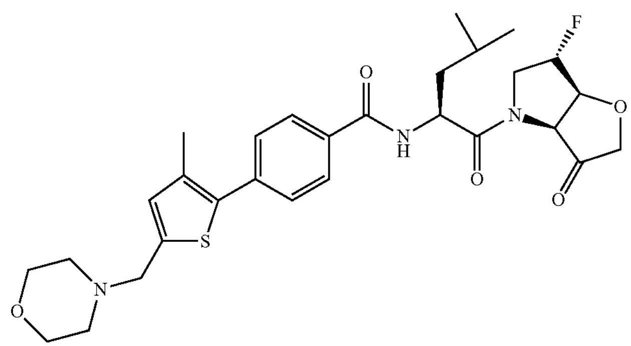 | A | | 489<br>[M + 18 − morpholine]⁺ 471<br>[M + H − morpholine]⁺ |

TABLE 1-continued

| No. | Structure | P2 | P3 building block | MS data |
|---|---|---|---|---|
| 8.45 | 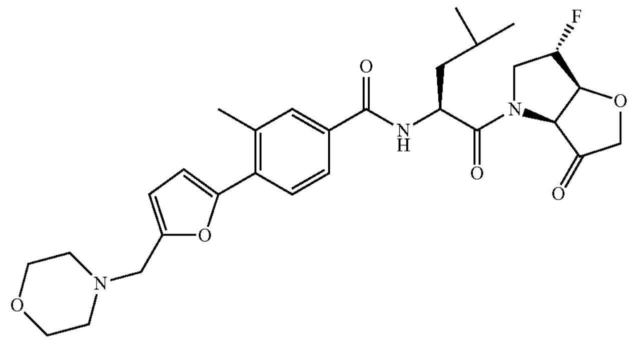 | A | | 560<br>[M + 18]+<br>473<br>[M + H – morpholine]+ |
| 8.46 | 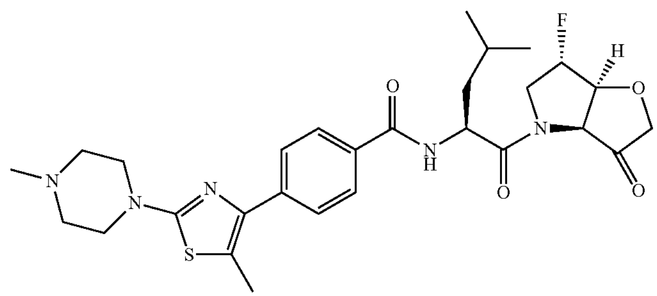 | A | | [M + H]+ 533<br>[M + 18]+ 551 |
| 8.47 | 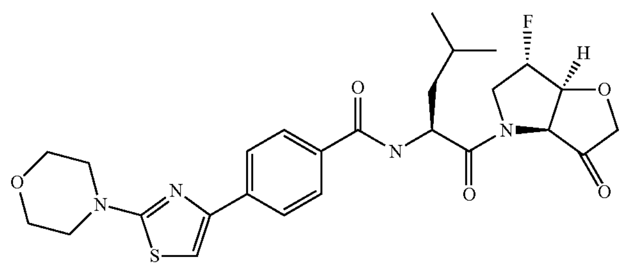 | A | | [M + H]+ 531<br>[M + 18]+ 549 |

TABLE 1-continued

| No. | Structure | P2 | P3 building block | MS data |
|---|---|---|---|---|
| 8.48 | 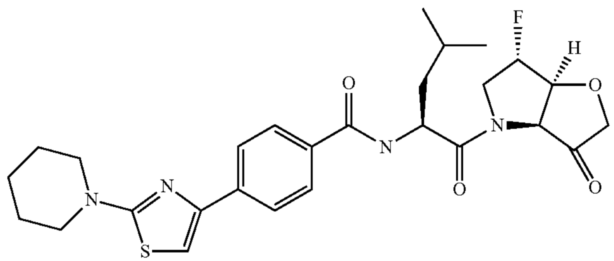 | A | | [M + H]⁺ 529<br>[M + 18]⁺ 547 |
| 8.49 | 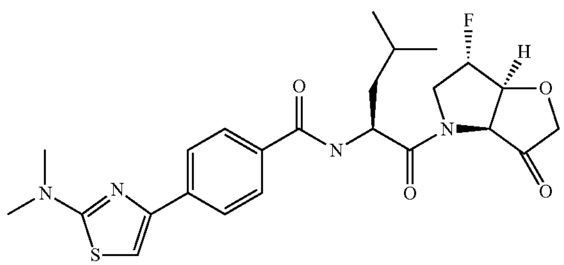 | A | | [M + H]⁺ 489<br>[M + 18]⁺ 507 |
| 8.50 | 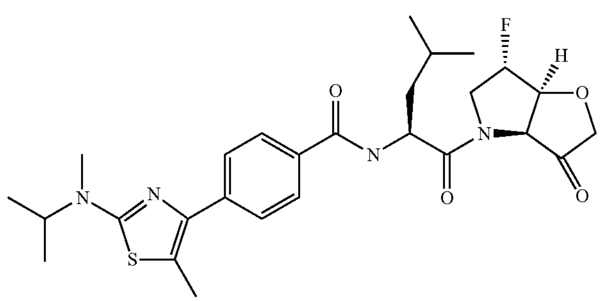 | A | | [M + H]⁺ 531<br>[M + 18]⁺ 549 |

TABLE 1-continued

| No. | Structure | P2 | P3 building block | MS data |
|---|---|---|---|---|
| 8.51 | 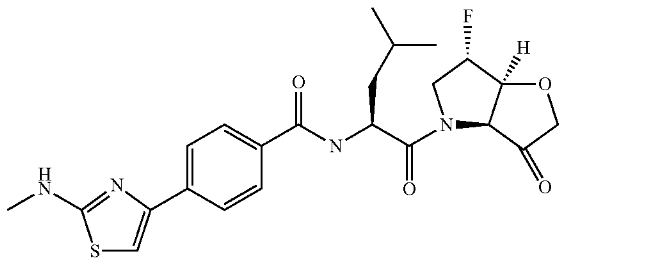 | A | | [M + H]+ 475 [M + 18]+ 493 |
| 8.52 | 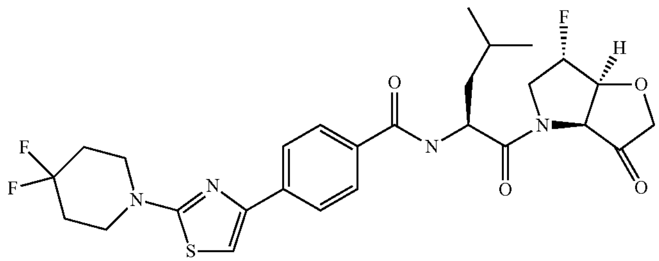 | A | | [M + H]+ 565 [M + 18]+ 583 |
| 8.53 | 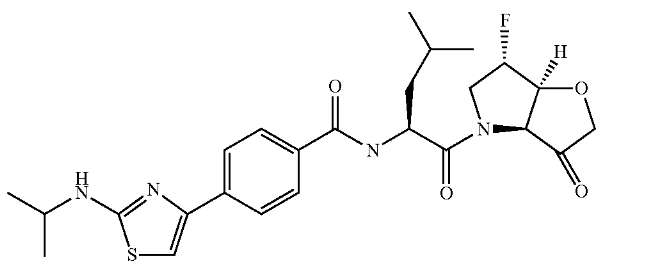 | A | | [M + H]+ 503 [M + 18]+ 521 |
| 8.54 | 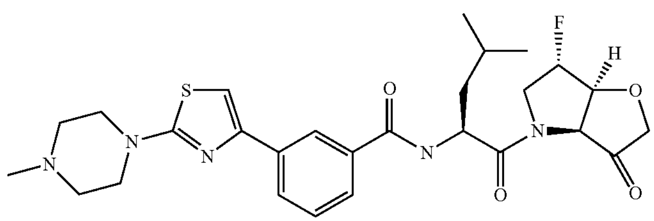 | A | | [M + H]+ 544 [M + 18]+ 562 |

TABLE 1-continued

| No. | Structure | P2 | P3 building block | MS data |
|---|---|---|---|---|
| 8.55 | 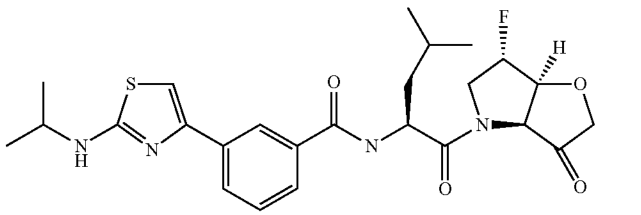 | A | | [M+H]+ 503<br>[M+18]+ 521 |
| 8.57 | 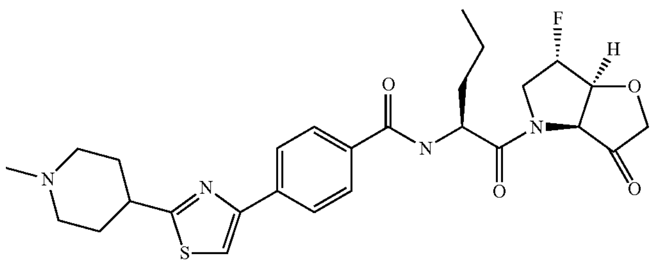 | A | | [M+H]+ 543<br>[M+18]+ 561 |
| 8.59 | 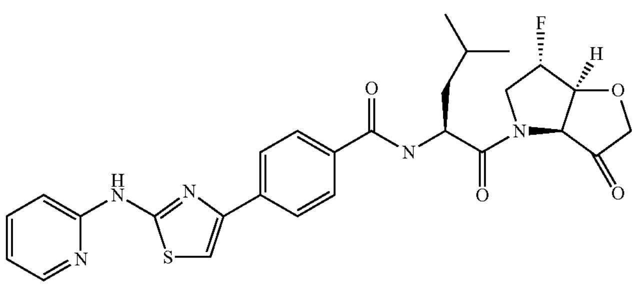 | A | | [M+H]+ 538<br>[M+18]+ 556 |

TABLE 1-continued

| No. | Structure | P2 | P3 building block | MS data |
|---|---|---|---|---|
| 8.60 | 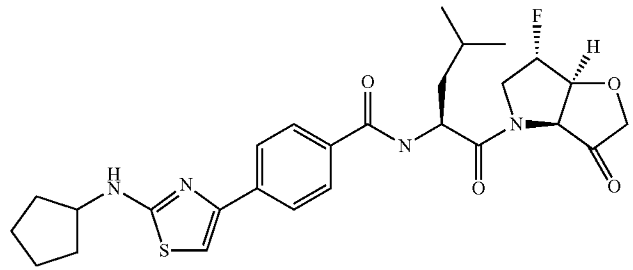 | A | | [M + H]+ 529 [M + 18]+ 547 |
| 8.61 | 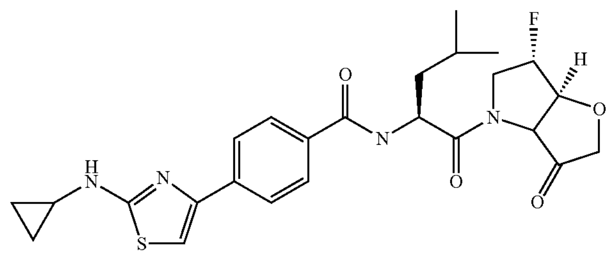 | A | | [M + H]+ 501 [M + 18]+ 519 |
| 8.62 | 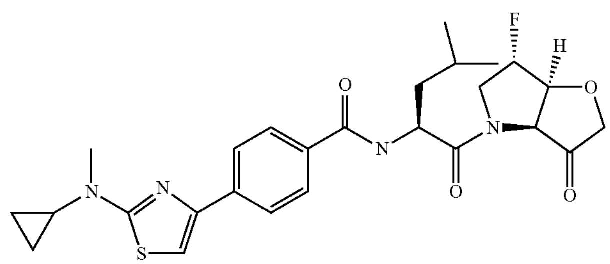 | A | | [M + H]+ 515 [M + 18]+ 533 |

TABLE 1-continued

| No. | Structure | P2 | P3 building block | MS data |
|---|---|---|---|---|
| 8.64 | 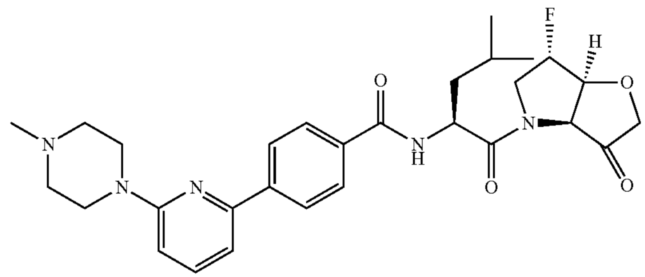 | A | | [M + H]⁺ 538<br>[M + 18]⁺ 556 |
| 8.65 | 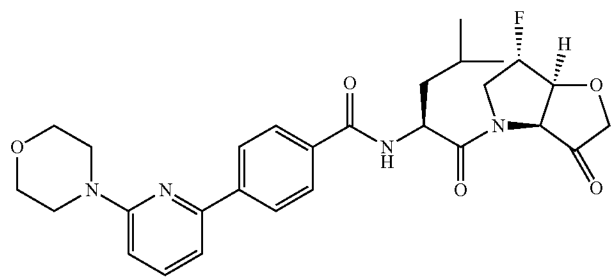 | A | | [M + H]⁺ 525<br>[M + 18]⁺ 543 |

P2 building blocks

A                B                C

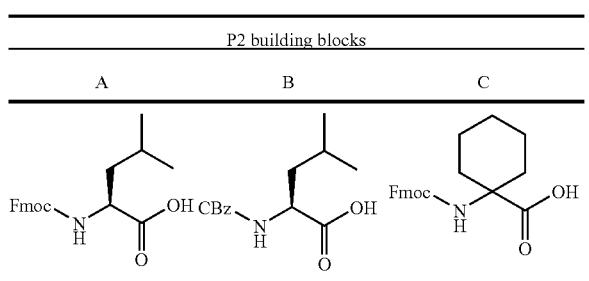

Solid phase synthesis of 8.1-8.13, 8.15-8.55, 8.57, 8.59-8.62, 8.64 & 8.65 was generally carried out using Murphy's linker methodology using known chemistries as described in WO02/88106. The ketone function of the FmocNH bicycle was derivatised as an acid labile semicarbazone which provided a carboxylic acid for attachment to the aminomethyl functionalised polymer support resin using HBTU, HOBt and NMM. After Fmoc removal the corresponding P2 Fmoc acid was coupled on where the symmetric anhydride was preformed. Coupling was first carried out for 8 h, and then repeated with fresh reagents overnight. After Fmoc removal the P3 acids were introduced using standard coupling conditions. Washing, drying and cleavage from the resin provided the crude desired material which was purified either by column chromatography or preparative hplc. Compounds which required modified procedures are described below.

1H-Indole-2-carboxylic acid [1-(6-fluoro-3-oxo-hexahydrofuro[3,2-b]pyrrole-4-carbonyl)-3-methyl-butyl]-amide (Example 8.6)

To the resin bound $H_2N$-L-Leu-P1 (150 mg, 0.03 mmol) was added a solution of indole-2-carboxylic acid (24.2 mg, 0.15 mmol) in DMF (1.0 mL). A solution of 1,3-diisopropylcarbodiimide (19 mg, 0.15 mmol) and 1-hydroxybenzotriazole hydrate (23 mg, 0.15 mmol) in DMF (1 mL) was then added. The reaction was agitated overnight and then washed with DMF (7×10 mL), MeOH (5×10 mL) and TBME (5×10 mL). After drying under vacuum for 17 h, the product was cleaved from the resin by suspension in 10 mL of 95:5 TFA:water for 45 mins. The filtrate was then concentrated under $N_2$ stream, purified by semi preparative HPLC and then freeze dried to give the title compound as a white solid. Compounds were characterised by HPLC, $^1H$ NMR and MS which showed both the ketone and hydrate forms to be present.

4-Piperidin-4-yl benzoic acid

4-Phenylpiperidine (10.0 g, 62 mmol) and pyridine (5.74 mL, 71 mmol) were dissolved in DCM (80 mL) and cooled to 0° C. A solution of acetyl chloride (4.00 mL, 71 mmol) in DCM (20 mL) was added drop wise to the above solution. The mixture was then stirred for 2 h at RT and when deemed to be complete by hplc, extracted with water, dried and concentrated in vacuo to afford a light yellow oil (10.6 g, 84%) which solidified on standing and was used without further purification. The yellow oil (10.6 g, 52.2 mmol) was dissolved in DCM and cooled to −78° C. and treated with oxalyl chloride (18.3 mL, 209 mmol) drop wise followed by the addition of aluminium chloride (20.9 g, 157 mmol) in portions. When the addition was complete, the flask was placed in an ice-salt bath, and the mixture stirred at −20 C for 3 h and then at RT overnight. The mixture was then poured onto ice-water and extracted with DCM (100 mL×3), dried and concentrated in vacuo. The residue was dissolved in aq. NaOH (2N) and HCl (6N) was added at 0° C. to acidify the solution to pH 5. The precipitate (7.9 g) was filtered off and washed with water (200 mL). The residue was then suspended in 6N HCl and heated at reflux for 18 h. The solvent was evaporated and the residue was recrystallised from ethanol. Crystals were filtered off and provided the title compound (5.05 g, 63%).

4-(5-Piperidin-1-ylmethyl-thiophen-2-yl)benzoic acid

5-Bromo-2-thiophenecarboxaldehyde (10 mmol) and piperidine (10 mmol) were mixed in THF (10 mL) and dibutyltin dichloride (0.2 mmol) was added. After stirring at RT for 5 minutes, phenylsilane (11 mmol) was added and the reaction allowed to stir at room temperature for a further 17 h. The reaction was then concentrated in vacuo and the residue purified by flash chromatography (silica gel, DCM) to give 1-(5-bromo-thiophen-2-ylmethyl)-piperidine: m/z=260, 262 in MS ES+ as a golden oil which was used directly in the subsequent step. A reaction tube containing a magnetic stirrer bar was charged with 4-carboxyphenylboronic acid (0.05 mmol), the thiophene bromide (0.05 mmol), Pd(PPh$_3$)$_4$ (0.025 mmol), acetonitrile (2 mL) and 1M Na$_2$CO$_3$ (aq) (2 mL). The reaction tube was then sealed and heated by microwave irradiation (100 W, 4 mins) to 150° C. and held at that temperature for 10 mins. After being allowed to cool to room temperature the reaction were acidified to pH 1 with 1M HCl and the resulting precipitate filtered off. This crude product was then passed through a silica plug to remove any inorganic species and concentrated to give a the title compound as a brown powder m/z=304 in MS ES+, which was characterised by hplc and MS and used in the next step without any further purification.

4-(5-Morpholin-4-ylmethyl-thiophen-2-yl)benzoic acid

To synthesise 4-(5-morpholin-4-ylmethyl-thiophen-2-yl) benzoic acid, the piperidine was substituted by morpholine in the previous experimental.

5-[2-(4,4-Difluoro-piperidin-1-yl)-ethoxy]-benzofuran-2-carboxylic acid

To a solution of 4,4-difluoropiperidine hydrochloride (1 g, 6.3 mmol) in THF (20 mL) was added methylbromoacetate (0.63 mL, 6.6 mmol) and triethylamine (2.65 mL, 19.0 mmol). The reaction was heated at reflux for 4 h. The reaction was diluted with water (50 mL) and the product extracted with ethyl acetate (3×20 mL). The combined organic fractions were washed with brine, dried over magnesium sulphate and concentrated in vacuo to yield (4,4-difluoropiperidin-1-yl)acetic acid methyl ester as a brown oil (1.17 g, 96%). MS 194 (M+H)$^+$. To a solution of (4,4-dfluompiperidin-1-yl)acetic acid methyl ester (1.17 g, 6.1 mmol) in THF (15 mL) at 0° C. was added potion wise lithium aluminium hydride (0.46 g, 12.2 mmol). Once the effervescence had ceased the reaction was heated at 60° C. for 1.5 h. The reaction was quenched with water (10 mL) followed by sodium hydroxide solution (2N, 10 mL) then water (10 mL). The reaction was filtered and the filtrate extracted with ethyl acetate (3×20 mL). The combined organic fractions were washed with brine, dried over magnesium sulphate and concentrated in vacuo to yield 2-(4,4-difluoropiperidin-1-yl)-ethanol as a brown oil (0.99 g, 99%). MS 166 (M+H)$^+$. To a solution of diisopropylazodicarboxylate (0.36 mL, 1.82 mmol) in DCM (20 mL) was added polymer supported triphenylphosphine (728 mg, 2.18 mmol). The reaction was stirred at RT for 10 min. 5-Hydroxy-benzofuran-2-carboxylic acid ethyl ester (025 g, 1.21 mmol) and 2-(4,4-difluoropiperidin-1-yl)-ethanol (210 mg, 1.27 mmol) were added and the reaction stirred at RT for 16 h. The reaction was filtered and the filtrate concentrated in vacuo. The product was purified on silica eluting with 50% tert-butyl methyl ether in n-heptane to yield 5-[2-(4,4-difluoropiperidin-1-yl)ethoxy]benzofuran-2-carboxylic acid ethyl ester as a yellow solid (375 mg, 88%). MS 354 (M+H)$^+$. To a solution of 5-[2-(4,4-difluoropiperidin-1-yl)ethoxy]benzofuran-2-carboxylic acid ethyl ester (375 mg, 1.06 mmol) in THF (5 mL) and water (1 mL) was added lithium hydroxide (34 mg, 2.12 mmol). The reaction was stirred at RT for 16 h. The THF was removed in vacuo and the remaining aqueous solution dried overnight in a freeze dryer to yield the crude title compound as a brown solid. MS 326 (M+H. 5.3 min) and used for coupling onto H$_2$N-Leu-P1 without any further purification.

5-[2-(4-Trifluoromethyl-piperidin-1-yl)-ethoxy]-benzofuran-2-carboxylic acid

To a solution of 4-trifluoromethylpiperidine hydrochloride (1 g, 5.3 mmol) in THF (20 mL) was added methylbromoacetate (0.52 mL, 5.5 mmol) and triethylamine (2.2 mL, 15.8 mmol). The reaction was heated at reflux for 4 h and then diluted with water (50 mL) and the product extracted with ethyl acetate (3×20 mL). The combined organic fractions were washed with brine, dried over magnesium sulphate and concentrated in vacuo to yield (4-trifluoromethylpiperidin-1-yl)acetic acid methyl ester as a brown oil (1.19 g, 98%). MS 226 (M+H)$^+$. To a solution of (4-trifluoromethylpiperidin-1-yl)acetic acid methyl ester (1.19 g, 5.3 mmol) in THF (15 mL) at 0° C. was added portion wise lithium aluminium hydride (0.4 g, 10.6 mmol). Once the effervescence had ceased the reaction was heated at 60° C. for 1.5 h. The reaction was quenched with water (10 mL) followed by sodium hydroxide solution (2N, 10 mL) then water (10 mL). The reaction was filtered and the filtrate extracted with ethyl acetate (3×20 mL). The combined organic fractions were washed with brine, dried over magnesium sulphate and concentrated in vacuo to yield 2-(4-trifluoromethylpiperidin-1-yl)-ethanol as a brown oil (1.0 g, 99%). MS 198 (M+H)$^+$. To a solution of diisopropylazodicarboxylate (0.58 mL, 2.28 mmol) in DCM (20 mL) was added polymer supported triphenylphosphine (1.14 g, 3.4 mmol). The reaction was stirred at RT for 10 mins. 5-Hydroxybenzofuran-2-carboxylic acid ethyl ester (0.47 g, 2.3 mmol) and 2-(4-trifluoromethylpiperidin-1-yl)-ethanol (0.45 g, 2.28 mmol) were added and the reaction stirred at RT for 16 h. The reaction was filtered and the filtrate concentrated in vacuo. The product was purified on silica eluting with 50% tert-butyl methyl ether in n-heptane to yield 5-[2-(4-trifluoromethylpiperidin-1-yl)ethoxy]benzofuran-2-carboxylic acid ethyl ester as a yellow solid (548 mg, 62%). MS 386 (M+H)$^+$. To a solution of 5-[2-(4-trifluoromethylpiperidin-1-yl)ethoxy]benzofuran-2-carboxylic acid ethyl ester (548 mg, 1.42 mmol) in THF (5 mL) and water (1 mL) was added lithium hydroxide (45 mg, 2.84 mmol). The reaction was stirred at RT for 16 h. The THF was removed in vacuo and the remaining aqueous solution dried overnight in a freeze dryer to yield the crude title compound as a brown solid. MS 358 (M+H)$^+$ which was used directly for coupling with H$_2$N-Leu-P1.

4-[2-(4-Methyl-piperazin-1-yl)-thiazol-4-yl]-benzoic acid

To thiocarbonyldiimidazole (2 g, 11.5 mmol) in THF (30 mL) at RT was added N-methylpiperazine (1.00 g, 10 mmol) drop wise. The reaction was stirred at RT for 2 h and then at 55° C. for 1 h. The reaction was cooled to RT and 20 mL of THF was removed in vacuo. 2M NH$_3$ (10 mL) in MeOH was added and the reaction stirred for 15 h. A further 2M NH$_3$ (10 mL) in MeOH was added and the reaction maintained at 55° C. for 8 h. A pale yellow precipitate (1.00 g) was observed and filtered off, dried and used directly in the next step. The thiourea (0.84 g, 5.2 mmol) was dissolved in EtOH (30 mL) and 4-(2-bromo-acetyl)-benzoic acid (1.28 g, 5.2 mmol) was added. The reaction was heated at reflux for 3 h. The reaction was cooled to RT and the solid filtered off. The solid was washed with Et$_2$O and dried thoroughly. This procedure provided the title compound as a pale yellow solid (1.23 g, 77%).

[1-(6-Fluoro-3-oxo-hexahydro-furo[3,2-b]pyrrole-4-carbonyl)-cyclohexyl]-carbamic acid 9H-fluoren-9-ylmethyl ester (Example 8.20)

Fmoc-1-amino-1-cyclohexane carboxylic acid (0.300 mg, 0.82 mmol) was dissolved in DCM (8 mL) and DAST (1 mL, 8.2 mmol) was added. After 1.5 h the starting material was consumed and H$_2$O (5 mL) was added drop wise with care. The organic layer was removed, dried (Na$_2$SO$_4$) and concentrated in vacuo to afford a pale brown solid (0.287 g, 96%). This material was used crude in the next step. (1-Fluorocarbonyl-cyclohexyl)-carbamic acid 9H-fluoren-9-ylmethyl ester (0.050 g, 0.135 mmol) was dissolved in DMF (1 mL) and added to H$_2$N-P1 in DMF (1 mL). NMM (0.027 g, 0.27 mmol) was added and the reaction left overnight. The resin was filtered off to remove spent reagents and fresh reagents were added and the reaction repeated for a further 24 h. After washing with DMF (10 mL×10) and DCM (10 mL×10) the title compound (loading equivalent to 50% yield) was obtained bound to resin.

[1-(6-Fluoro-3-oxo-hexahydro-furo[3,2-b]pyrrole-4-carbonyl)-3-methyl-butyl]-carbamic acid benzyl ester (Example 8.14)

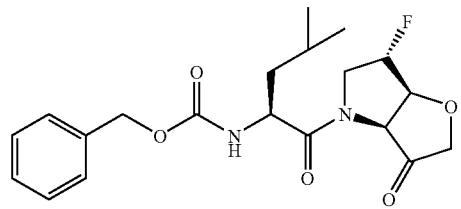

Example 8.14 was prepared in solution rather than on solid phase.

6-Fluoro-3-hydroxy-hexahydro-furo[3,2-b]pyrrole-4-carboxylic acid tert-butyl ester (0.200 g, 0.81 mmol) was dissolved in DCM (4 mL) at 0° C. and TFA (4 mL) added. After stirring at 0-4° C. for 1 h, the solvent was evaporated in vacuo and the residue left under high vacuum for 4 h to afford a brown oil. The residue was dissolved in DMF (5 mL) and WSC.HCl (171 mg, 0.89 mmol), HOBt (137 mg, 1.01 mmol), Cbz-Leu-OH (226 mg, 0.85 mmol) and Et$_3$N (337 µl, 2.43 mmol) added. After stirring at room temperature overnight, the reaction mixture was concentrated in vacuo, dissolved in EtOAc (10 mL), washed with H$_2$O (5 mL) and saturated NaHCO$_3$ solution (5 mL), dried (Na$_2$SO$_4$) and evaporated in vacuo to afford a colourless oil (242 mg; [M+H]$^+$ 395). (1-(6-Fluoro-3-hydroxy-hexahydro-furo[3,2-b]pyrrole-4-carbonyl)-3-methyl-butyl]-carbamic acid benzyl ester (242 mg, 0.62 mmol) was dissolved in dry DCM (8 mL) and Dess-Martin periodinane (261 mg, 0.62 mmol) added. The reaction immediately turned light brown. After stirring at room temperature for 2.5 h, the yellow solution was diluted with DCM (8 mL) and washed with saturated NaHCO$_3$ solution (5 mL), dried (Na$_2$SO$_4$) and evaporated in vacuo to afford a yellow residue. Purification by column chromatography (EtOAc: heptane; 1:2) yielded the title compound as a colourless oil, 147 mg; [M+H]$^+$ 393.

4-Thiocarbamoyl-piperazine-1-carboxylic acid tert-butyl ester

To a solution of piperazine-1-carboxylic acid tert-butyl ester (32.2 mmol) in tetrahydrofuran (60 ml) was added thiocarbonyldiimidazole (37.0 mmol). The reaction was stirred at RT for 2 h then heated at 55° C. for 1 h. The reaction was concentrated in vacuo to approximately half the volume and methanolic ammonia added (7N, 107.4 mmol). The reaction was heated at 55° C. for 16 h. The reaction was concentrated in vacuo to approximately half the volume and cooled to 0° C. at which point the product precipitated from solution. The product was collected by filtration to yield the title compound as a white solid (3.3 g). 1H NMR (400 MHz, d$_6$-DMSO) 1.40 (9H, s), 3.32 (4H, s), 3.71 (4H, s), 7.42 (1H,s).

4-[4-(4-Carboxy-phenyl)-thiazol-2-yl]-piperazine-1-carboxylic acid tert-butyl ester To a suspension of 4-thiocarbamoyl-piperazine-1-carboxylic acid tert-butyl ester (13.3 mmol) in ethanol (60 ml) was added 4-(2-bromoacetyl)-benzoic acid (13.3 mmol) and 4-methylmorpholine (13.9 mmol). The reaction was heated at reflux for 2.5 h. The reaction was concentrated in vacuo and the solid washed with water (200 ml) to yield the title compound as a white solid (3.9 g). 1H NMR (400 MHz, CDCl$_3$) 1.45 (9H, s), 3.58 (8H, m), 4.86 (1H, s), 6.95 (1H,s), 7.97 (2H, d, J 8 Hz), 8.1 (2H, d, J 8 Hz).

4-{2-[4-(2-Methoxy-ethyl)-piperazin-1-yl]-thiazol-4-yl}-benzoic acid

4-[4-(4-Carboxy-phenyl)-thiazol-2-yl]-piperazine-1-carboxylic acid tert-butyl ester (5.0 mmol) was dissolved in hydrochloric acid in dioxane (4N, 25 ml) and the reaction stirred at RT for 2 h. The reaction was concentrated in vacuo to yield 4-(2-piperazin-1-yl-thiazol-4-yl)-benzoic acid. Tri-methoxyethane (6.5 mmol) was dissolved in aqueous hydrochloric acid (1N, 10 ml) and the reaction heated at 50° C. for 1.5 h. The reaction was allowed to cool to RT and was then added to a suspension of 4-(2-piperazin-1-yl-thiazol-4-yl)-benzoic acid (5.0 mmol) in acetonitrile (25 ml) and sodium acetate buffer (1N, pH 5.5, 10 ml). The reaction was stirred at RT for 1.5 h. Sodium cyanoborohydride (6.5 mol) was added and the reaction stirred at RT for 16 h. The reaction was concentrated in vacuo and the product purified by flash chromatography (silica gel, 10% methanol in dichloromethane) to give the title product as a colourless oil (0.9 g). m/z=348 (100% M+H) in MS ES+.

4-[1-(5-Bromo-thiophen-2-yl)-ethyl]-morpholine

To a solution of morpholine (1.20 mmol) in titanium (IV) isopropoxide (1.95 mmol) was added 2-acetyl-5-bromothiophene (1.20 mmol). The reaction was heated in a microwave at 150° C. for 5 minutes. Sodium borohydride (1.95 mmol) was added and the reaction stirred at RT for 16 h. The reaction was diluted with sodium hydroxide solution (2N, 10 ml) and the solids formed removed by filtration. The filtrate was extracted with ethylacetate (3×20 ml), the combined organics were washed with brine and dried over magnesium sulphate. The product was purified by flash chromatography (silica gel, 10-20% ethylacetate in iso-hexane) to, give the title product as a brown oil: m/z=276 (100%, M+H), 278 (100%, M+H) in MS ES+.

4-[5-(1-Morpholinl-4-yl-ethyl)-thiophen-2-yl]-benzoic acid

4-[1-(5-Bromo-thiophen-2-yl)-ethyl]-morpholine (0.36 mmol), 4-methoxycarbonylphenylboronic acid (0.43 mmol) and sodium carbonate (1.09 mmol) were suspended in dioxane:water (2 ml, 2:1). Nitrogen gas was bubbled through the reaction for 5 minutes then tetrakis(triphenylphosphine)palladium(0) (0.04 mmol) added. The reaction was heated in a microwave at 150° C. for 10 min. The reaction was concentrated in vacuo and the product was purified by flash chromatography (silica gel, 10% methanol in dichloromethane) to give the titie product as a brown oil: m/z=318 (50% M+H), 231 (100%, M+H-morpholine) in MS ES+.

4-{[(1-Methylimidazol-2-yl)methyl]amino}benzoic acid

1-Methyl-2-imidazolecarboxaldehyde (5.0 mmol) and methyl-4-aminobenzoate (5.0 mmol) were mixed in MeOH (7 mL). Acetic acid (0.3 mL) was added and the mixture stirred for 30 minutes at room temperature. The reaction mixture was cooled, sodium cyanoborohydride (5.0 mmol) was added and the reaction allowed to stir at room temperature for a further 17 h. The reaction mixture was then concentrated under vacuum and partitioned between H$_2$O and EtOAc. The aqueous layer was extracted with EtOAc, and the combined organic layers were washed with H$_2$O, brine, dried over MgSO$_4$ and the solvent removed under vacuum. The residue was purified by flash chromatography (silica gel, 5% MeOH in DCM) to give methyl 4-{[(1-methylimidazol-2-yl) methyl]amino}benzoate: m/z=246 in MS ES+ as a pale yellow solid which was used directly in the subsequent step.

To a solution of methyl ester (2.5 mmol) in 1,4-dioxane (5 mL) was added 1M aqueous KOH solution (5.5 mmol) and the reaction mixture stirred for 18 h. The reaction mixture was neutralised to pH 7 with 1M HCl and concentrated by N$_2$ stream. The product was resuspended in water and lyophilised to give 4-{[(1-methylimidazol-2-yl)methyl] amino}benzoic acid: m/z232 in MS ES+ as a white solid which was used directly in the subsequent step.

4-[5-(1-Morpholin-4-yl-ethyl)-furan-2-yl]-benzoic acid

2-Acetylfuran (20 mmol) and morpholine (20 mmol) were added to neat titanium isopropoxide (32 mmol) and the reaction stirred under N$_2$ at room temperature for 3 h. Methanol (90 ml) was then added followed by the careful portionwise addition of NaBH$_4$ (32 mmol). After stirring at room temperature for 10 mins, the reaction was quenched by addition of 0.1M NaOH and the resultant mixture filtered through a celite pad. The filtrate was extracted twice with DCM, dried over Na$_2$SO$_4$ and concentrated in-vacuo. Flash chromatography of the residue (silica, 5 to 20% EtOAc in Heptane) yielded pure 4-(1-furan-2-yl-ethyl)-morpholine as a golden oil: m/z in MS ES+=182 [M+H]$^+$, 2.76 mmol, 14% yield.

4-(1-furan-2-yl-ethyl)-morpholine (1.1 mmol) was taken up in DCM (5 ml) and stirred at 0° C. Nitrogen was passed through the reaction vessel and bubbled out through a Dreschel bottle containing a saturated aqueous solution of sodium thiosulphate, whilst bromine (1.54 mmol in 2 ml DCM) was added dropwise. After addition the reaction was stirred at room temperature for 2 h, then diluted with more DCM, washed twice with 2M $Na_2CO_3$ solution, dried over $Na_2SO_4$ and concentrated in-vacuo. After purification by flash chromatography (silica, 5 to 10% EtOAc in hexane), 4-[1-(5-bromo-furan-2-yl)-ethyl]-morpholine was obtained as a golden oil: m/z in MS ES+=260, 262 [M+H]+, 0.46 mmol, 42% yield.

4-[1-(5-bromo-furan-2-yl)-ethyl]-morpholine (0.54 mmol) was taken up in 7 ml toluene and 4-carboxymethylphenylboronic acid (0.54 mmol) was added as a solution in 0.7 ml of EtOH. 12 mi of 2M aqueous $Na_2CO_3$ solution was added, followed by $Pd(PPh_3)_4$ (0.054 mmol). Reaction was stirred at 70° C. for 17 h under a nitrogen atmosphere and then cooled to room temperature and extracted with DCM (×2). Combined organic layers were washed with brine, concentrated in vacuo and the residue purified by flash chromatography (silica, 20-50% EtOAc in hexane). This furnished the pure 4-[5-(1-Morpholin-4-yl-ethyl)-furan-2-yl]-benzoic acid methyl ester as a powdery grey solid: m/z in MS ES+=316 [M+H]+, 0.08 mmol, 15% yield.

This ester (0.08 mmol) was heated to 70° C. in 18% HCl for 2 h at which point HPLC showed all the starting material to have been hydrolysed. The reaction was cooled and the product that precipitated out of solution was collected by filtration as a white solid and used directly in the next step.

4-(2-Methyl-pyridin-3-yloxy)-benzoic acid

A reaction tube containing a magnetic stirrer bar was charged with ethyl-4-fluorobenzoate (1 mmol), 2-methyl-3-pyridol (1.0 mmol), potassium carbonate (1.08 mmol) and DMF (2 ml). The reaction tube was then sealed and heated by microwave irradiation (100 W, 4 mins) to 150° C. and held at that temperature for 80 mins. The solution was filtered to remove the insoluble potassium carbonate and then concentrated in vacuo. The residue was purified by preparative HPLC and freeze dried to give 4-(2-Methyl-pyridin-3-yloxy)-benzoic acid ethyl ester as a white solid which was hydrolysed by 6N aqueous HCl solution heated by microwave irradiation (200 W) for 3 mins at 150° C. The solution was freeze dried to give to 63 mg of hydrochloride salt of the title compound as a white powder m/z=229 in MS ES+, which was characterised by HPLC and MS.

4-[2-(1-Dimethylamino-ethyl)-thiazol-4-yl]-benzoic acid

4-{2-[1-(tert-Butoxycarbonyl-methyl-amino)-ethyl]-thiazol-4-yl}-benzoic acid methyl ester Boc-L-NMe-Alanine-OH (1.0 g, 4.92 mmols) was dissolved in dioxan (10 mls) and to this was added pyridine (0.25 mls), di-tert-butyl dicarbonate (1.4 g, 6.4 mmols) and ammonium hydrogen carbonate (0.49 g, 6.2 mmols). After stirring for 18 hours the crude reaction mixture was concentrated in vacuo and resuspended in ethyl acetate. This was washed with 1M $KHSO_4$ and the organic layer dried over magnesium sulphate. After concentration, a clear oil was obtained (0.79 g). This was dissolved in ethylene glycol dimethyl ether (10 mls) and to this was added Lawesson's reagent (4.31 mmols, 1.74 g). After stirring at room temperature for 3 hours the reaction mixture was concentrated in vacuo and the residue resuspended in ethyl acetate. This was washed with 1M $Na_2CO_3$ and the organic layer dried over magnesium sulphate. After concentration a yellow oil was obtained. This was purified by flash chromatography (heptane/ethyl acetate) to give a white solid (0.73 g). This was dissolved in ethanol (10 mls) and 4-(2-Bromo-acetyl)-benzoic acid methyl ester (3.34 mmols, 0.86 g) was added. The reaction was heated to 50° C. for one hour. The crude product was purified by flash chromatography (heptan/ethyl acetate) to give a white solid (0.39 g). ESMS (M+H=377.23).

4-[2-(1-Dimethylamino-ethyl)-thiazol-4-yl]-benzoic acid

4-{2-[1-(tert-Butoxycarbonyl-methyl-amino)-ethyl]-thiazol-4-yl}-benzoic acid methyl ester was deprotected with a solution of 4N HCl in dioxan for 1 h. The solvent was removed in vacuo and the residue freeze dried to get a white solid which was methylated as followed. 4-[2-(1-Methylamino-ethyl)-thiazol-4-yl]-benzoic acid methyl ester (0.44 mmol) was stirred for one hour with formaldehyde (1.1 equivalent) in methanol (2 ml) and sodium acetate buffer (1N, pH 5.5, 1 ml). Sodium cyanoborohydride (0.49 mmol) was added and the reaction stirred at RT for 2 h. The reaction was concentrated in vacuo and the residue was extracted in EtOAc and washed with a 1 M aqueous solution of sodium carbonate. The organic layer was concentrated in vacuo and the residue was hydrolysed by 6N aqueous HCl solution heated by microwave irradiation (200 W) for 3 mins at 150° C. The solution was freeze dried to give to 134 mg of hydrochloride salt of the title compound as a white powder m/z=277 in MS ES+, which was characterised by HPLC and MS.

E-4-[2-(1H-Imidazol-4-yl)-vinyl]-benzoic acid

{4-(methoxycarbonyl)benzyl(triphenyl)}phosphonium bromide on polymer support. Methyl-4-bromomethyl benzoate (26 mmol) were added to a suspension of 4.4 g of PS-Triphelphosphine resin (Fluka, 3 $mmolg^{-1}$) in 40 ml of DMF. The solution was gently stirred at 65° C. for 48 hours. The phosphonium resin was washed with DMF (4×40 ml), DCM (4×40 ml) and TBME (2×40 ml) and dried in vacuo for 18 h.

E-4-[2-(1H-Imidazol-4-yl)-vinyl]-benzoic acid

A reaction tube containing a magnetic stirrer bar was charged with 1-Methyl-1H-imidazole-2-carbaldehyde(1.5 mmol), potassium carbonate (2.1 mmol), {4-(methoxycarbonyl)benzyl(triphenyl)}phosphonium bromide on polymer support (1.5 mmol) and methanol (4 ml). The reaction tube was then sealed and heated by microwave irradiation (100 W, 3 mins) to 150° C. and held at that temperature for 5 mins. The solution was filtered to remove the insoluble potassium carbonate and then concentrated in vacuo. The residue was purified by preparative HPLC and freeze dried to give E-4-[2-(1-Methyl-1H-imidazol-2-yl)-vinyl]-benzoic acid methyl ester as a white solid which was hydrolysed by 6N aqueous HCl solution heated by microwave irradiation (200 W) for 3 mins at 150° C. The solution was freeze dried to give to 90 mg of hydrochloride salt of the title compound as a white powder m/z=215 in MS ES+, which was characterised by HPLC and MS.

E-4-[2-(1-Methyl-1H-imidazol-2-yl)-vinyl]-benzoic acid

Same as example 8.28. 1-Methyl-1H-imidazole-2-carbaldehyde was used as the aldehyde. The title compound was E-4-[2-(3-Methyl-3H-imidazol-4-yl)-vinyl]-benzoic acid Same as example 828. 3-Methyl-3H-imidazole-4-carbaldehyde was used as the aldehyde. The title compound was obtained as a white powder m/z=229 in MS ES+, which was characterised by HPLC and MS 4-[2-(1H-Imidazol-4-yl)-ethyl]-benzoic acid E-4-[2-(1-Methyl-1H-imidazol-2-yl)-vinyl]-benzoic acid methyl ester was hydrogenated using Pd/C (10% of substrate weight), ammonium formate (5 equivalents) in isopropanol heated by microwave irradiation (200 W) for 5 mins at 150° C. The solution was filtered through celite to remove the insoluble catalyst, diluted with water and freeze-dried to remove the excess of ammonium formate. The obtained solid was hydrolysed by 6N aqueous HCl solution heated by microwave irradiation (200 W) for 3 mins at 150° C. The solution was freeze dried to give to the hydrochloride salt of the title compound as a white powder m/z=217 in MS ES+, which was characterised by HPLC and MS.

4-[2-(1-Methyl-1H-imidazol-2-yl)-ethyl]-benzoic acid

Same as example 8.31. 4-[2-(1-Methyl-1H-imidazol-2-yl)-vinyl]-benzoic acid methyl ester (Example 8.29) was used as the methyl ester. The title compound was obtained as a white powder m/z=231 in MS ES+, which was characterised by HPLC and MS.

Potassium 4-methyl(pyridin-2-yl)aminomethylbenzoate

2-Methylaminopyridine (1.0 mmol) and methyl-4-formyl-benzoate (1.0 mmol) were mixed in THF (2 mL) and dibutyltin dichloride (0.1 mmol) was added. After stirring at RT for 10 minutes, phenylsilane (1.1 mmol) was added and the reaction mixture allowed to stir at room temperature for a further 17 h. The reaction mixture was then concentrated by $N_2$ stream and the residue purified by flash chromatography (silica gel, heptane:EtOAc) to give methyl 4-[methyl(pyridin-2-yl)amino]methylbenzoate: m/z=257 in MS ES+ as a yellow oil which was used directly in the subsequent step.

To a solution of methyl ester (0.27 mmol) in 1,4-dioxane (0.6 mL) was added 1M aqueous KOH solution (0.59 mmol) and the reaction mixture stirred for 18 h. The reaction mixture was concentrated by $N_2$ stream, resuspended in water and the product lyophilised to give potassium 4-methyl(pyridin-2-yl)aminomethyl benzoate: m/z 243 in MS ES+ as an off-white solid which was used directly in the subsequent step.

Sodium 4-(2-{1(S)-[(tert-butoxycarbonyl)(methyl)amino]ethyl}-5-methyl-1,3-thiazol-4-yl)benzoate Ethyl 4-propionylbenzoate (2.0 mmol), pyrrolidinone hydrotribromide (2.1 mmol) and 2-pyrrolidinone (2.2 mmol) were heated in THF (20 mL) at 50 C for 2.5 h. The mixture was cooled, filtered, concentrated under vacuum and the residual oil partitioned between $H_2O$ and MTBE. The aqueous layer was extracted with MTBE, and the combined organic layers were washed with saturated aqueous sodium metabisulfite solution, $H_2O$, brine, dried over $MgSO_4$ and the solvent removed under vacuum. The residue was purified by flash column chromatography (9:1 $^i$Hexane: MTBE) to afford ethyl-4(2'-bromopropionyl)benzoate as a clear oil.

Ethyl 4(2'-bromopropionyl)benzoate (0.5 mmol), BOC (Me)Ala thioamide (0.5 mmol) and NMM (0.5 mmol) were heated in EtOH (2 mL) at 80 C for 3 h. The mixture was cooled, concentrated by $N_2$ stream and the crude product partitioned between $H_2O$ and MTBE. The aqueous layer was extracted with MTBE, and the combined organic layers were washed twice with 1M $KHSO_4$, brine, dried over $MgSO_4$ and the solvent removed under vacuum to give a yellow oil. The residue was purified by flash column chromatography (9:1 $^i$Hexane: EtOAc) to afford an intense yellow fraction. On standing for several hours, this fraction decolorises and ethyl 4-(2-{1(S)-[(tert-butoxycarbonyl)(methyl)amino]ethyl}-5-methyl-1,3-thiazol-4-yl)benzoate was isolated by flash column chromatography (9:1 $^i$Hexane:EtOAc) as a clear oil: m/z=405 (MH+) and 349 (M-BOC+) in MS ES+.

To a solution of ethyl ester (0.24 mmol) in 1,4-dioxane (5 mL) and water (1 mL) was added 1M NaOH (0.53 mL) and the reaction mixture stirred for 18 h. The reaction mixture was concentrated under vacuum, the product resuspended in water and lyophilised to give sodium 4-(2-{1(S)-[(tert-butoxycarbonyl)(methyl)amino]ethyl}-5-methyl-1,3-thiazol-4-yl)benzoate: m/z 377 (MH+) and 321 (M-BOC+) in MS ES+ as a white solid which was used directly in the subsequent step.

Lithium 4-{2-[1(S)-(dimethylamino)ethyl]-5-methyl-1,3-thiazol-4-yl}benzoate

Ethyl 4-(2-{1(S)-[(tert-butoxycarbonyl)(methyl)amino]ethyl}-5-methyl-1,3-thiazol-4-yl)benzoate was prepared as described previously.

To a solution of BOC-protected amine (0.25 mmol) in 1,4-dioxane (3 mL) was added 4M HCl in dioxane (4 mL) and the reaction mixture stirred for 2 h. The reaction mixture was concentrated under vacuum to afford a viscous pale yellow oil. The oil was dissolved in 1:1 $H_2O$:MeCN and lyophilised to afford ethyl 4-{2-[1(S)-(methylamino)ethyl]-5-methyl-1,3-thiazol-4-yl}benzoate hydrochloride salt A pH 5.5 buffer was prepared by adding AcOH to 1M NaOAc until pH 5.5 was reached. The amine hydrochloride (0.28 mmol) was dissolved in 1:1 buffer:MeOH (4 mL) and formaldehyde (37 weight % in water; 0.31 mmol) was added. The mixture was stirred for 1 h and then sodium cyanoborohydride (0.31 mmol) was added portionwise. After 1 h, the reaction mixture was concentrated by $N_2$ stream. The residue was partitioned between saturated aqueous $NaHCO_3$ and EtOAc. The aqueous layer was extracted with EtOAc and the combined organic layers were washed with $H_2O$, brine, dried over $Na_2SO_4$ and the solvent removed under vacuum. The residue was purified by preparative HPLC (0.1% TFA in $H_2O$: MeCN). The combined HPLC fractions were partitioned between saturated aqueous $NaHCO_3$ and EtOAc. The aqueous layer was extracted with EtOAc and the combined organic layers were washed with brine, dried over $Na_2SO_4$ and the solvent removed under vacuum. The absence of EtOAc was confirmed by 1H-NMR.

The ethyl ester (0.19 mmol) was dissolved in 1:1 $H_2O$:1, 4-dioxane (8 mL) and 1M LiOH (0.42 mL) was added and the reaction mixture stirred for 17 h. The reaction mixture was adjusted to pH 8 by addition of 1M HCl. The mixture was concentrated under vacuum, resuspended in 1:1 $H_2O$:MeCN and lyophilised to give lithium 4-(2-{1(S)-[(dimethyl)amino]

ethyl}-5-methyl-1,3-thiazol-4-yl)benzoate: m/z 291 (MH+) in MS ES+ as a white solid and was used directly in the subsequent step.

5-(4-Methyl-morpholin-2-ylmethoxy)-benzofuran-2-carboxylic acid

Ethyl 5-methoxybenzofuran carboxylate (22.7 mmol) was dissolved in dichlormethane (20 ml) and a 1.0 M solution of boron tribromide methyl sulphide complex in dichloromethane (68.1 mmol) was added. The mixture was heated at reflux over night The solvent was evaporated under vacuo and the residue purified by flash chromatography to obtain ethyl 5-hydroxybenzofuran carboxylate as a white solid.

Triphenyl phosphine polymer bound (8.96 mmol) was suspended in anhydrous dichloromethane (20 ml) then diisopropyl azodicarboxylate (7.76 mmol) was added and the mixture was stirred for 15 minutes at room temperature. Then ethyl 5-hydroxybenzofuran carboxylate (5.97 mmol) was added over 5 minutes followed by the addition of 4-N-boc-3-morpholinecarboxylic acid (5.97 mmol) over 5 minutes too. The mixture was stirred at room temperature over night. The solvent was evaporated under vacuo and the residue purified by flash chromatography to obtain ethyl 5-(4-Boc-morpholin-2-ylmethoxy)-benzofuran-2-carboxylate: m/z=406 in MS ES+, as clear oil.

Ethyl 5-(4-Boc-morpholin-2-ylmethoxy)-benzofuran-2-carboxylate (2.47 mmol) was dissolved in 30 ml of a 4.0 M solution of hydrochloric acid in dioxan and stirred at room temperature for 1 hour. After removing the solvent under vacuo the resulting amine was dissolved in anhydrous dichloromethane and N-methylmorpholine (5.67 mmol) was added and stirred at room temperature for 5 minutes. Then allylchloroformate (2.71 mmol) was added and the mixture was stirred at room temperature over night under an inert atmosphere. The mixture was washed with a 1.0 M solution of hydrochloric acid, water, dried over $Na_2SO_4$ and the solvent was evaporated in vacuo. The residue was purified by flash chromatography to yield ethyl 5-(4-alloc-morpholin-2-ylmethoxy)-benzofuran-2-carboxylate: m/z=390 in MS ES+, as a white solid.

Ethyl 5-(4-alloc-morpholin-2-ylmethoxy)-benzofuran-2-carboxylate (2.09 mmol) was dissolved in 3 ml of tetrahydrofuran. Then 3 ml of a 1.0 M solution of lithium hydroxide were added and the mixture stirred at room temperature over night. After removing the tetrahydrofuran under vacuo the mixture was acidified with a 1 M solution of hydrochloric acid to Congo red, extracted with dichloromethane, washed with water, dried over $Na_2SO_4$ and the solvent was removed under vacuo to yield 5-(4-alloc-morpholin-2-ylmethoxy)-benzofuran-2-carboxylic acid as a white solid.

5-(4-Alloc-morpholin-2-ylmethoxy)-benzofuran-2-carboxylic acid (3 equiv) was then incorporated on the peptide as described previously (600 mg; 0.32 mmol/g) with HBTU (3 equiv), HOBt (3 equiv) and NMM (6 equiv) in DMF over night at room temperature.

The Alloc group was removed with (1) DCM (4×1 min); (2) borane dimethylamine complex (40 equiv), tetrakis (triphenylphosphine) palladium (0) (0.1 equiv) in anhydrous DCM (2×15 min); (3) DCM (3×1 min); (4) DMF (3×1 min); (5) dioxan-water (9:1) (3×1 min); (6) DMF (3×1 min); (7) MeOH (3×1 min); (8) DCM (3×1 min) and the peptide resin was treated with dibutyltin dichloride (5 equiv), phenylsilane (5 equiv) and a 37% solution of formaldehyde in water (5 equiv) in THF for 2 hours at room temperature. The reminder of the procedure was carried out as described in the general protocol.

3-Methyl-5-(4-methyl-morpholin-2-ylmethoxy)-benzofuran-2-carboxylic acid

4-Methoxyphenol (0.119 mol) was dissolved in dry toluene and treated with sodium hydride (0.120 mol) at room temperature for 60 h. The sodium phenolate solution was heated to +100° C. and α-chloroacetoacetate (0.09 mol) was added. After stirring at +110° C. for a further 4 hours, the mixture was cool to room temperature, washed with water and brine, dried over $Na_2SO_4$ and the solvent was evaporated in vacuo to yield a crude α-(4-methoxyphenoxy)acetoacetate as a dark brown oil. Phosphoric acid (0.22 mol) was mixed with $P_2O_5$ (0.35 mol) at room temperature and stirred at +130° C. for 4 hours. The mixture was allowed to cool to +100° C., the acetoacetate was slowly added, and held at that temperature for 2 hours. After cooling to room temperature, ice was carefully added to the stirred solution, extracted with toluene, concentrated in vacuo and purified by flash chromatography on silica to yield ethyl 3-methyl-5-methoxybenzofuran carboxylate: m/z=235 in MS ES+, as a white solid.

Ethyl 3-methyl-5-methoxybenzofuran carboxylate (8.53 mmol) was dissolved in dichloromethane (10 ml) and a 1.0 M solution of boron tribromide methyl sulphide complex in dichloromethane (25.59 mmol) was added. The mixture was heated at reflux over night. The solvent was evaporated under vacuo and the residue purified by flash chromatography to obtain ethyl 3-methyl-5-hydroxybenzofuran carboxylate as a white solid.

Triphenyl phosphine polymer bound (1.37 mmol) was suspended in anhydrous dichloromethane (10 ml) then diisopropyl azodicarboxylate (1.18 mmol) was added and the mixture was stirred for 15 minutes at room temperature. Then ethyl 3-methyl-5-hydroxybenzofuran carboxylate (0.91 mmol) was added over 5 minutes followed by the addition of 4-N-boc-3-morpholinecarboxylic acid (0.91 mmol) over 5 minutes too. The mixture was stirred at room temperature over night. The solvent was evaporated under vacuo and the residue purified by flash chromatography to obtain ethyl 3-methyl-5-(4-Boc-morpholin-2-ylmethoxy)-benzofuran-2-carboxylate: m/z=419 in MS ES+, as clear oil.

Ethyl 3-methyl-5-(4-Boc-morpholin-2-ylmethoxy)-benzofuran-2-carboxylate (1.05 mmol) was dissolved in 30 ml of a 4.0 M solution of hydrochloric acid in dioxan and stirred at room temperature for 1 hour. After removing the solvent under vacuo the resulting amine was dissolved in 20 ml of a mixture 2 to 1 of methanol and a buffered solution of acetic acid and sodium acetate at pH=5.3. A 37% solution of formaldehyde in water (1.16 mmol) was added and the mixture was stirred at room temperature for 1 hour. Then sodium cyanoborohydride (1.16 mmol) was added and the mixture was stirred over night at room temperature. The methanol was removed under vacuo and the water was eliminated by liophylisation. The solid obtained was purified by flash chromatography to yield ethyl 3-methyl-5-(4-methyl-morpholin-2-ylmethoxy)-benzofuran-2-carboxylate: m/z=334 in MS ES+, as a white solid.

Ethyl 3-methyl-5-(4-methyl-morpholin-2-ylmethoxy)-benzofuran-2-carboxylate (0.12 mmol) was dissolved in 300 μl of tetrahydrofuran. Then 300 μl of a 1.0 M solution of lithium hydroxide were added and the mixture stirred at room temperature for 3 hours. The tetrahydrofuran was removed under vacuo and the water eliminated by lyophilisation to yield the tilted compound as a white solid: m/z=304 in MS ES−.

4-[2-(1-Dimethylamino-ethyl)-thiazol-5-yl]-benzoic acid lithium salt

4-(2-Azido-acetyl)-benzoic acid methyl ester 4-(2-Bromo-acetyl)-benzoic acid methyl ester (15.5 mmol) was dissolved in ethanol (120 ml) and acetic acid (4.8 ml). Sodium azide (31 mmol) was added and the reaction stirred at 4° C. overnight. The ethanol was removed and the mixture diluted with ethyl acetate (100 ml). The organic layer was washed with saturated sodium hydrogen carbonate (2'50 ml) and dried (MgSO$_4$). The solvent was removed in vacuo to give a yellow solid, which was re-crystallized from ethanol to give the title compound as a pale yellow solid (2.6 g). IR 2117 cm$^{-1}$

4-(2-Amino-acetyl)-benzoic acid methyl ester hydrochloride

4(2-Azido-acetyl)-benzoic acid methyl ester (6.53 mmol) was suspended in methanol (30 ml) and aqueous hydrochloric acid (6.53 mmol, 1M) was added. A catalytic amount of palladium on carbon (10% wt) was added and the reaction stirred over an atmosphere of hydrogen for 3 h. The reaction was filtered and the solvent removed in vacuo to give the title compound (1.3 g) as a yellow solid m/z=194 in MS ES+, which was used in the next step without purification.

4-{2-[2-(S)-(tert-Butoxycarbonyl-methyl-amino)-propionylamino]-acetyl}-benzoic acid methyl ester 4-(2-Amino-acetyl)-benzoic acid methyl ester hydrochloride (2.22 mmol), WSC.HCl (2.44 mmol), Boc-N-methyl-(L)-alanine (2.44 mmol) and HOBt (2.77 mmol) were suspended in dichloromethane (10 ml). NMM (2.44 mmol) was added and the reaction stirred for 2 h. The reaction was diluted with ethyl acetate (50 ml) and washed with 10% citric acid (2×25 ml) and saturated sodium hydrogen carbonate (2×25 ml). The organic layer was dried (MgSO$_4$) and the solvent removed in vacuo to give a brown oil residue. Purification by silica chromatography eluting with 10-50% ethyl acetate/iso-hexane gave the title compound (620 mg) as a pale yellow oil m/z=379 in MS ES+.

4-{2-(S)-[1-(tert-Butoxycarbonyl-methyl-amino)-ethyl]thiazol-5-yl}-benzoic acid methyl ester 4-{2-[2-(S)-(tert-Butoxycarbonyl-methyl-amino)-propionylamino]-acetyl}-benzoic acid methyl ester (1.65 mmol) was dissolved in dry THF and Lawesson's reagent (2.5 mmol) was added. The reaction was heated at reflux for 5 h and cooled to room temperature. The solvent was removed in vacuo and the residue was dissolved in ethyl acetate (100 ml). The organic layer was washed with 10% citric acid (2×50 ml) and saturated sodium hydrogen carbonate (2×50 ml) and dried (MgSO$_4$). The solvent was removed in vacuo to give a yellow oil residue, which was purified by silica chromatography to give the title compound (570 mg) as a pale yellow solid. 1H NMR (CDCl$_3$, 400 MHz) 1.5(s, 9H), 1.6(d, 7 Hz), 2.8 (brs, 3H), 3.9(s, 3H), 5.6(brm, 1H), 7.6(m, 2H), 7.9(s, 1H), 8.0(m, 2H).

4-{2-(S)-[1-(tert-Butoxycarbonyl-methyl-amino)-ethyl]-thiazol-5-yl}-benzoic acid 4-{2-(S)-[1-(tert-Butoxycarbonyl-methyl-amino)-ethyl]-thiazol-5-yl}-benzoic acid methyl ester (0.75 mmol) was dissolved in methanol (10 ml) and lithium hydroxide (10 ml, 1M) was added. The reaction was stirred at room temperature overnight and the methanol removed in vacuo. The aqueous solution was taken to pH=3 with 1M hydrochloric acid and extracted with ethyl acetate (2×50 ml). The organic layer was dried (MgSO$_4$) and the solvent removed in vacuo to give an off-white powder, which was purified by silica chromatography eluting with 50-80% ethyl acetate/iso-hexane. The title compound was obtained as a white powder (252 mg) m/z=363 in MS ES+.

4-[2-(S)-1-Dimethylamino-ethyl)-thiazol-5-yl]-benzoic acid methyl ester

4-{2-(S)-[1-(tert-Butoxycarbonyl-methyl-amino)-ethyl]-thiazol-yl}-benzoic acid (0.75 mmol) was dissolved in 50% TFA/DCM (2 ml) and stirred for 1 h. The solvent was removed in vacuo and the residue placed under high vacuum for 3 h to give a light brown oil residue. The residue was dissolved in methanol (2 ml) and buffer (1 ml, 1M sodium acetate/acetic acid, pH=5.5) was added. Formaldehyde (0.83 mmol, 37 wt % in water) was added and the reaction stirred for 30 minutes. Sodium cyanoborohydride (0.83 mmol) was added and the reaction stirred overnight at room temperature. The methanol was removed in vacuo and the aqueous diluted with saturated sodium hydrogen carbonate (25 ml). The aqueous layer was extracted with ethyl acetate (2×25 ml) and the organic layer dried (MgSO$_4$). The solvent was removed in vacuo and the residue purified by silica chromatography to give the title compound (158 mg) as an off-white solid 1H NMR (CD$_3$OD, 400 MHz) 1.5(d, J 7 Hz), 2.3(s, 6H), 3.9(s, 3H), 3.95(q, J 7 Hz), 7.7(m, 2H), 8.0(m, 3H).

4-[2-(1-Dimethylamino-ethyl)-thiazol-5-yl]-benzoic acid lithium salt

4-{2-(S)-[1-(tert-Butoxycarbonyl-methyl-amino)-ethyl]-thiazol-5-yl}-benzoic acid (0.54 mmol) was dissolved in methanol (2 ml) and lithium hydroxide (0.54 mmol, 1M) was added. The reaction was stirred overnight and the methanol removed in vacuo. The residue was diluted with water (5 ml) and the aqueous layer extracted with ethyl acetate. The aqueous layer was freeze-dried to give the title compound as an off-white solid (143 mg) which was used in the next step without further purification m/z=277 in MS ES+.

5-N,N-Dimethylamino-1H-indole-2-carboxylic acid

5-Amino-1H-indole-2-carboxylic acid ethyl ester

5-Nitro-1H-indole-2-carboxylic acid ethyl ester (14.9 mmol) was suspended in acetone (50 ml) and added to a mixture of titanium(III) chloride (91 ml, >10% in 2M hydrochloric acid) and ammonium acetate (265 ml, 4M). The reaction was stirred for 2 h and neutralized with saturated sodium hydrogen carbonate. The mixture was extracted with ethyl acetate (100 ml) and the organic layer dried (MgSO$_4$). The solvent was removed in vacuo to give a light brown solid which was purified by silica chromatography to give the title compound as an off-white solid (1.57 g) m/z=205 in MS ES+.

5-N,N-Dimethylamino-1H-indole-2-carboxylic acid ethyl ester

5-Amino-1H-indole-2-carboxylic acid ethyl ester (7.7 mmol) was dissolved in acetonitrile (30 ml) and formaldehyde (19.2 mmol, 37% wt in water) was added. Sodium cyanoborohydride (7.7 mmol) was added and the reaction stirred at room temperature overnight. The acetonitrile was removed in vacuo and the residue was purified by silica chromatography to give the title compound was a pale yellow solid (244 mg). m/z=233 in MS ES+.

5-N,N-Dimethylamino-1H-indole-2-carboxylic acid

5-N,N-Dimethylamino-1H-indole-2-carboxylic acid ethyl ester (1.05 mmol) was suspended in ethanol (1 ml) and lithium hydroxide (1.2 ml, 1M in water) was added. The reaction was stirred at room temperature overnight. The solution was taken to pH=7 with 1M hydrochloric acid and the ethanol removed in vacuo. The aqueous layer was extracted with ethyl acetate and the organic layer dried (MgSO4). The ethyl acetate was removed in vacuo to give the title compound as a yellow powder (75 mg), which was used in the next step without purification. m/z=205 in MS ES+.

4-{2-[1-(tert-Butoxycarbonyl-methyl-amino)-ethyl]-thiazol-4-yl}-benzoic acid Boc-L-NMe-Alanine-OH (1.0 g, 4.92 mmols) was dissolved in dioxan (10 mls) and to this was added pyridine (0.25 mls), di-tert-butyl dicarbonate (1.4 g, 6.4 mmols) and ammonium hydrogen carbonate (0.49 g, 6.2 mmols). After stirring for 18 hours the crude reaction mixture was concentrated in vacuo and re-suspended in ethyl acetate. This was washed with 1M KHSO$_4$ and the organic layer dried over magnesium sulphate. After concentration a clear oil was obtained (0.79 g). This was dissolved in ethylene glycol dimethyl ether (10 mls) and to this was added Lawesson's reagent (4.31 mmols, 1.74 g). After stirring at room temperature for 3 hours the reaction mixture was concentrated in vacuo and the residue re-suspended in ethyl acetate. This was washed with 1M Na$_2$CO$_3$ and the organic layer dried over magnesium sulphate. After concentration a yellow oil was obtained. This was purified by flash chromatography (heptane/ethyl acetate) to give a white solid (0.73 g). This was dissolved in ethanol (10 mls) and 4-(2-Bromo-acetyl)-benzoic acid methyl ester (3.34 mmols, 0.86 g) was added. The reaction was heated to 50° C. for one hour. The crude product was purified by flash chromatography (heptane/ethyl acetate) to give a white solid (0.39 g). ESMS (M+H=377.23) which was subsequently hydrolysed to the corresponding acid.

4-[2-(1-Dimethylamino-2-methoxy-ethyl)-thiazol-4-yl]-benzoic acid

Boc-L-Serine(OMe)-OH (2.4 g, 6.0 mmols) was dissolved in dioxan (20 mls) and to this was added pyridine (0.31 mls), di-tert-butyl dicarbonate (1.7 g, 7.8 mmols) and ammonium hydrogen carbonate (0.62 g, 7.2 mmols). After stirring for 18 hours the crude reaction mixture was concentrated in vacuo and re-suspended in ethyl acetate. This was washed with 1M KHSO$_4$ and the organic layer dried over magnesium sulphate. After concentration the crude product was purified by flash chromatography to yield 0.55 g of a clear oil. This was dissolved in ethylene glycol dimethyl ether (20 mls) and to this was added Lawesson's reagent (2.78 mmols). After stirring at room temperature for 3 hours the reaction mixture was concentrated in vacuo and the residue purified by flash chromatography (silica gel, DCM) to give a yellow oil (2-Methoxy-1-thiocarbamoyl-ethyl)-carbamic acid tert-butyl ester (0.49 g).

The ester (0.25 g, 1.07 mmols) was dissolved in ethanol (10 mls) and 4-(2-Bromo-acetyl)-benzoic acid methyl ester (1.18 mmols, 0.30 g) was added. The reaction was heated to 50° C. for one hour. The crude product was purified by preparative HPLC (MeCN/H$_2$O) to yield 0.138 g of a yellow solid. The Boc group was removed via treatment with 4M HCl/dioxan for one hour after which time the reaction mixture was concentrated in vacuo. The free amine (0.093 g, 0.265 mmols) was then dimethylated. The crude HCl salt was dissolved in 5 mls of methanol and buffered with 2.5 mls pH 5.5 Sodium acetate/acetic acid. Formaldehyde was added (0.58 mmols) and the reaction stirred for one hour. Sodium cyanoborohydride was then added (0.58 mmols, 0.036 g) and the reaction stirred for a further thirty minutes. The reaction mixture was concentrated in vacuo and purified by preparative HPLC to yield 60 mg of a yellow solid. Finally, the methyl ester was hydrolysed with 1M LiOH (5 mls) and dioxan (5 mls) at room temperature for two hours. The reaction mixture was concentrated in vacuo and lyophilised from water to yield 62 mg of the desired acid as the lithium salt. ESMS (M+H=307.04)

4-[2-(4-Fluoro-1-methyl-pyrrolidin-2-yl)-thiazol-4-yl]-benzoic acid

4-Fluoro-2-[4-(4-methoxycarbonyl-phenyl)-thiazol-2-yl]-pyrrolidine-1-carboxylic acid tert-butyl ester (0.1 g) was treated with 4M HCl/dioxan (10 mls) for 2 hours. The reaction mixture was then concentrated in vacuo and lyophilised from water to yield a yellow solid (0.8 g). The crude HCl salt was dissolved in 5 mls of methanol and buffered with 2.5 mls pH 5.5 Sodium acetate/acetic acid. Formaldehyde was added (0.38 mmols, 0.0032 mls) and the reaction stirred for one hour. Sodium cyanoborohydride was then added (0.38 mmols, 0.024 g) and the reaction stirred for a further thirty minutes. The reaction mixture was concentrated in vacuo and the residue re-suspended in ethyl acetate. This was washed with 1M Na$_2$CO$_3$ and the organic layer dried over magnesium sulphate. After concentration a yellow solid was obtained (0.075 g). Finally, the methyl ester was hydrolysed with 1M LiOH (5 mls) and dioxan (5 mls) at room temperature for two hours. The reaction mixture was concentrated in vacuo and lyophilised from water to yield 62 mg of the desired acid as the lithium salt ESMS (M+H=306.88)

2-[4-(4-Carboxy-phenyl)-thiazol-2-yl]-4-fluoro-pyrrolidine-1-carboxylic acid 2-[4-(4-Carboxy-phenyl)-thiazol-2-yl]-4-fluoro-pyrrolidine-1-carboxylic acid tert-butyl ester The amide (0.32 g, 1.37 mmols) was dissolved in ethylene glycol dimethyl ether (10 mls) and to this was added Lawesson's reagent (0.61 g, 1.5 mmols). After stirring at room temperature for 3 hours the reaction mixture was concentrated in vacuo and the residue re-suspended in ethyl acetate. This was washed with 1M Na$_2$CO$_3$ and the organic layer dried over magnesium sulphate. After concentration a yellow oil was obtained. This was purified by flash chromatography (heptane/ethyl acetate) to give a white solid (0.36 g). This was dissolved in ethanol (10 mls) and 4-(2-Bromo-acetyl)-benzoic acid methyl ester (0.419 g, 1.59 mmols) was added. The reaction was heated to 50° C. for one hour. The crude product was purified by flash chromatography (heptane/ethyl acetate) to give a white solid (0.34 g). The methyl ester was then treated with 1M LiOH (10 mls) and dioxan (10 mls) for 3 hours. After quantitative hydrolysis, the crude product was concentrated in vacuo and the residue re-suspended in ethyl acetate. This was washed with 1M $KHSO_4$ and the organic layer dried over magnesium sulphate. After concentration in vacuo the product was lyophilised from acetonitrile/water to yield the title compound as a white solid (0.32 g). ESMS (M+H=393.03).

Lithium 5-(4-N-methylmorpholino-2S-methyloxy)benzofuran carboxylate as single enantiomers)

Ethyl 5-(4-boc-morpholino-2R-methyloxy)benzofuran carboxylate

4-Boc-2R-hydroxymethylmorpholine was prepared according to method described in Heterocycles, 1993 35, 105-109. To a mixture of polymer supported triphenylphosphine (2.4 mmol) and the hydroxymethylmorpholine (1.2 mmol) in dry dichloromethane (5 ml) ethyl-hydroxybenzofuran-2-carboxylate (1.2 mmol) and DIAD (1.2 mmol) was added at room temperature. The mixture was stirred further 16 hours, filtrated, diluted in dry dichloromethane (5 ml) and stirred at room temperature another 16 hours. Filtrated, concentrated in vacuo and purified by y flash chromatography on silica (ethylacetate, hexane) to yield ethyl-5-(4-boc-morpholino-2R-methyloxy)benzofuran carboxylate (0.3 mmol), m/z=406 in MS ES+, as an oil.

Lithium 5-(4-N-methylmorpholino-2R-methyloxy)benzofuran carboxylate

Ethyl-5-(4-boc-morpholino-2R-methyloxy)benzofuran carboxylate (0.3 mmol) was dissolved in HCl in dioxane (4M, 15 ml), stirred at room temperature for 4 hours, concentrated in vacuo to a pale yellow oil. The crude benzofuran hydrochloride (0.3 mmol) and formaldehyde (0.35 mmol) were mixed in THF (5 mL) and dibutyltin dichloride (0.05 mmol) was added. After stirring at RT for 5 minutes, phenylsilane (0.6 mmol) was added and the reaction allowed to stir at room temperature for a further 17 h. The reaction was then concentrated in vacuo and the residue purified by flash chromatography (silica gel, ethyl acetate, isopropanol, triethylamine) to give ethyl-5-(4-N-methylmorpholino-2R-methyloxy)benzofuran carboxylate: m/z=320 in MS ES+ as a clear oil.

To ethyl-5-(4-N-methyl morpholino-2R-methyloxy)benzofuran carboxylate (0.6 mmol) in 5 ml dioxane was added LiOH (0.6 mmol) in 1 ml of water. The mixture was refluxed for 16 hours, concentrated in vacuo to give lithium 5-(4-N-methylmorpholino-2R-methyloxy)benzofuran carboxylate: m/z 292 in MS ES+ as a white solid.

Lithium 5-(4-N-methylmorpholino-2S-methyloxy)benzofuran carboxylate

S-isomer m/z 292 in MS ES+ was prepared as a white solid white solid according to method used to prepare R-isomer but substituting 4-Boc-2R-hydroxymethylmorpholine by 4-Boc-2S-hydroxymethylmorpholine.

4-(3-Methyl-5-morpholino-4-ylmethyl-thiophen-2-yl)-benzoic acid

5-Bromo-4-methyl-thiophene-2-carboxylic acid methyl ester (8.51 mmol) was dissolved in EtOH (100 ml) and NaOH (42.5 mmol) added, as a 1M solution in water. Reaction was heated to 80° C. for 2 h, after which time all starting material had been consumed. Reaction was then concentrated in vacuo and the residue taken up in DCM and shaken with 1M HCl. The resulting biphasic mixture was then filtered and the filtrant washed with hexane and dried under vacuum. This gave 5-Bromo-4-methyl-thiophene-2-carboxylic acid as off white solid: m/z in MS AP–=219, 221 [M–H]⁻, 6.79 mmol, 80%. 5-Bromo-4-methyl-thiophene-2-carboxylic acid (6.79 mmol) was taken up in 30 ml DMF and morpholine (7.47 mmol), WSC.HCl (7.47 mmol) and HOBt (7.47 mmol) were added. Reaction was stirred at room temperature for 17 h and then diluted with EtOAc, washed with 1M HCl and brine, dried over $Na_2SO_4$ and concentrated in vacuo. Flash chromatography of the residue (silica, 33-50% EtOAc in hexane) gave (5-Bromo-4-methyl-thiophen-2-yl)-morpholin-4-yl-methanone as a pale golden oil: m/z in MS ES+=290, 292 [M+H]⁺, 4.67 mmol, 69%.

(5-Bromo-4-methyl-thiophen-2-yl)-morpholin-4-yl-methanone (1.78 mmol) was added to a flask containing 1M $THF.BH_3$ complex in THF (4.45 mmol). Reaction was stirred at reflux for 2.5 h under $N_2$. Methanol was then added until gas evolution ceased, followed by 10 ml of 1M NaOH and the reaction stirred at reflux for a further 7 h. The mixture was cooled to room temperature and extracted with EtOAc. This extract was concentrated in vacuo and the residue taken up in 1M HCl and washed with EtOAc. The acid layer was then basified with 1M NaOH and extracted back into EtOAc. Removal of solvent gave 4-(5-Bromo-4-methyl-thiophen-2-ylmethyl)-morpholine as a colourless oil: m/z in MS ES+=276, 278 [M+H]⁺, 0.98 mmol, 55%.

4-(5-Bromo-4-methyl-thiophen-2-ylmethyl)-morpholine (0.98 mmol) was taken up in 10 ml toluene and 4-carboxymethylphenylboronic acid (0.98 mmol) was added as a solution in 1 ml of EtOH. 6 ml of 2M aqueous $Na_2CO_3$ solution was added, followed by $Pd(PPh_3)_4$ (0.098 mmol). Reaction was stirred at 70° C. for 17 h under a nitrogen atmosphere and then cooled to room temperature and extracted with DCM (×2). Combined organic layers were washed with brine, concentrated in vacuo and the residue purified by flash chromatography (silica, 33-99% EtOAc in hexane). This furnished the pure 4-(3-Methyl-5-morpholi-4-ylmethyl-thiophen-2-yl)-benzoic acid methyl ester as a waxy white solid: m/z in MS ES+=332 [M+H]⁺, 0.090 mmol, 9%.

This ester (0.09 mmol) was heated to 70° C. in 18% HCl for 2 h at which point HPLC showed all the starting material to have been hydrolysed. The reaction was cooled and the product that precipitated out of solution was collected by filtration as a white solid. With no further purification this was coupled using the standard procedure.

3-Methyl-4-(5-morpholin-4-ylmethyl-furan-2-yl)-benzoic acid

A three necked flask was charged with methyl 4-bromo-3-methylbenzoate (2.18 mmol), bis(pinacolato)diboron (2.29 mmol), palladium acetate (0.065 mmol), potassium acetate (6.54 mmol) and DMF (10 ml). The solution was degassed by bubbling through $N_2$ gas for 30 mins and was then heated to 80° C. under $N_2$ for 3 h. Reaction was then cooled to room temperature and 4-(5-Bromo-furan-2-ylmethyl)-morpholine (2.18 mmol), cesium carbonate (3.27 mmol) and Pd(PPh3)4 (0.065 mmol) added. The reaction was heated to 80° C. and stirred for a further 17 h. Mixture was then diluted with EtOAc and water and filtered through a celite pad to remove black particulates. The organic layer was separated, washed with brine and dried over $Na_2SO_4$ and concentrated in vacuo.

Flash chromatography of the residue (silica, 10-99% EtOAc in hexane) gave 3-Methyl-4-(5-morpholin-4-ylmethyl-furan-2-yl)-benzoic acid methyl ester as a grey powdery solid: m/z in MS ES+=316 [M+H]$^+$, 0.51 mmol, 23%.

This ester (0.51 mmol) was heated to 70° C. in 18% HCl for 2 h at which point HPLC showed all the starting material to have been hydrolysed. The reaction was cooled and the product that precipitated out of solution was collected by filtration as a white solid. With no further purification this was coupled using the standard procedure.

4-[5-Methyl-2-(4-methyl-piperazin-1-yl)-thiazol-4-yl]-benzoic acid 4-propionylbenzoic acid (890 mg, 5 mmol), NaHCO$_3$ (1.26 g, 15 mmol), and iodomethane (935 μL, 15 mmol) in DMF (10 mL) were stirred at RT overnight. The mixture was diluted with saturated aqueous NaCl (50 mL) and extracted with ether (3×50 mL). The organic phase was washed with water (50 mL), dried, and evaporated. Flash chromatography (90 g silica, 2/1 petroleum ether—EtOAc) gave white solids of 4-Propionyl-benzoic acid methyl ester (744 mg, 77%).

1H NMR (CDCl$_3$, 400 MHz) δ 1.24 (t, 3H, J=7 Hz), 3.03 (q, 2H, J=7 Hz), 3.95 (s, 3H), 8.0 and 8.12 (ABq, 4H).

4-Propionyl-benzoic acid methyl ester (744 mg, 3.87 mmol), pyrrolidone hydrotribromide (1.98 g), and 2-pyrrolidinone (380 mg, 4.5 mmol) in THF (38 mL) were heated at 50° C. under nitrogen for 3 h. The mixture was cooled, filtered, concentrated, and then redissolved in ether (50 mL). The ether solution was washed successively with water (20 mL), saturated aqueous sodium thiosulphate (20 mL), saturated aqueous NaCl (20 mL), and water (20 mL), dried and evaporated to give crude 4-(2-Bromo-propionyl)-benzoic acid methyl ester as a yellow oil (1.025 g) that was used directly in the Hantzsch coupling. This material contained 91% of the desired bromoketone, 5% starting material, and 4% 4-bromo-1-butanol, as determined by 1H NMR.

1H NMR (CDCl$_3$, 400 MHz) δ 1.92 (d, 3H, J=7 Hz), 3.96 (s, 3H), 5.28 (q, 1H, J=7 Hz), 8.07 and 8.14 (ABq, 4H)

All of the 4-(2-Bromo-propionyl)-benzoic acid methyl ester above and piperazine-1-carboxylic acid tert-butyl ester (*J. Med. Chem.*, 1998, 5037-5054, 917 mg, 3.73 mmol) were refluxed in 36 mL THF at 70° C. for 2 h, under N$_2$. The precipitate was filtered and the filtrate evaporated to give yellow solids. Flash column chromatography (silica, 5/1 petroleum ether—EtOAc) gave 624 mg of 4-[4-(4-Methoxycarbonyl-phenyl)-5-methyl-thiazol-2-yl]-piperazine-1-carboxylic acid tert-butyl ester as a light yellow solid. Chromatography of the precipitate (silica, 2/1 petroleum ether—EtOAc) gave 32 mg more of compound. Total yield is 44%.

1H NMR (CDCl$_3$, 400 MHz) δ 1.46 (s, 9H), 2.43 (s, 3H), 3.42, (m, 4H), 3.54 (m, 4H), 3.90 (s, 3H), 7.68 and 8.04 (ABq, 4H).

The above methyl ester (564 mg, 1.35 mmol) was heated with 1.35 mL 2N NaOH, 5 mL THF, and 3.65 mL water at 60° C. for 4 h. The reaction mixture was evaporated, poured into 20 mL saturated aqueous NaCl and 20 mL CH$_2$Cl$_2$, and then acidified to pH 3 with 5% citric acid, in an ice bath. The layers were separated and the organic phase was extracted further with 2×10 mL CH$_2$C$_2$. The organic phases were combined, washed with water (10 mL), dried, and evaporated to give 4-[4-(4-Carboxy-phenyl)-5-methyl-thiazol-2-yl]-piperazine-1-carboxylic acid tert-butyl aster as a light yellow solid (537 mg, 98%).

1H NMR (CDCl$_3$, 400 MHz) δ 1.48 (s, 9H), 2.47 (s, 3H), 3.47 (m, 4H), 3.57 (m, 4H), 7.74 and 8.12 (ABq, 4H).

13C NMR (CDCl$_3$, 100 MHz) δ ppm: 12.6, 28.3, 42.8, 48.1, 80.3, 119.1, 127.8, 128.2, 130.1, 140.5, 145.6, 154.6, 167.2, 171.4.

LCMS: (M+H)$^+$ 404, (M−H)$^−$ 402.

4-[4-(4-Carboxy-phenyl)-5-methyl-thiazol-2-yl]-piperazine-1-carboxylic acid tert-butyl ester (0.421 mmol) was dissolved in 4M HCl in 1,4-dioxane, and stirred at room temperature for 1 h. The solvent was then removed under vacuum, and the residue 4-(5-Methyl-2-piperazin-1-yl-thiazol-4-yl)-benzoic acid was suspended in methanol (10 ml) and treated with AcOH/AcONa buffer (pH ~5.5, 5 ml), and formaldehyde (0.547 mmol). The reaction mixture was stirred at room temperature for 1 h, then treated with NaCNBH$_3$ (0.547 mmol) and stirred at room temperature overnight. The solvent was then removed under vacuum, and the residue was purified by column chromatography to afford the title compound (0.403 mmol, 95%). MS(ES) m/z 318 (100%, [M+H]$^+$).

4-(2-Morpholin-4-yl-thiazol-4-yl)-benzoic acid 4-(2-bromoacetyl)benzoic acid (1.23 mmol) and 1-morpholinethiocarboxamide (1.23 mmol, J. Med. Chem 1998, 41, 5037-5054) were mixed in THF (10 mL), then refluxed for 3.5 h. The reaction mixture was then allowed to reach room temperature and the obtained precipitate was collected by filtration and washed with 4 portions of diethyl ether. The crude product was crystallized from hot 1:1 EtOH-EtOAc to give a first harvest of colorless needles (0.16 g, 0.55 mmol). 1H NMR (DMSO-d$_6$, 400 MHz) δ 7.94 (4H, m), 7.49 (1H, s), 3.72 (4H, m), 3.44 (4H, m).

4-(2-Piperidin-1-yl-thiazol-4-yl)-benzoic acid 4-(2-bromoacetyl)benzoic acid (1.23 mmol) and 1-piperidinethiocarboxamide (1.23 mmol) were mixed in THF (10 mL), then refluxed for 3 h. The reaction mixture was then allowed to reach room temperature and the obtained precipitate was collected by filtration and washed with 3 portions of diethyl ether. The crude product was crystallized from hot 1:1 EtOH-EtOAc to give a first harvest of colorless needles (0.28 g, 0.95 mmol). 1H NMR (DMSO-d$_6$, 400 MHz,) δ 7.93 (4H, m), 7.40 (1H, s), 3.48 (4H, m), 1.60 (6H, m).

4-(2-Dimethylamino-thiazol-4-yl)-benzoic acid

To a stirred mixture of thiocarbonyldiimidazole (44.9 mmol) in THF (40 mL) at room temperature was added portionwise 2 M Dimethylamine in THF (44 mmol) and a temperature increase was observed. 40 min after final addition the reaction mixture was heated to 55° C. for 1 h, then allowed to reach room temperature again. The reaction was then concentrated in vacuo and the residue purified by flash chromatography (silica gel, Petroleum ether-EtOAc) to give the intermediate imidazole-1-carbothioic acid dimethylamide. This material was treated with freshly prepared sat. ammonia in methanol (40 ml) for 60 h, then concentrated in vacuo and the precipitated residue was suspended in diethyl ether and collected by filtration. The precipitate was washed with diethyl ether and air-dried to give a slight yellow solid (1.71 g, 16.4 mmol) which was used in the subsequent step. 4-(2-bromoacetyl)benzoic acid (1.23 mmol) and 1-piperidinethiocarboxamide (1.23 mmol) were mixed in THF (10 mL), then refluxed for 3 h. The reaction mixture was then allowed to reach room temperature and the obtained precipitate was collected by filtration and washed with 3 portions of diethyl ether. The crude product was crystallized from hot 1:1 EtOH-EtOAc to give a first harvest of colorless needles (0.1 g, 0.40 mmol). 1H NMR (DMSO-d$_6$, 400 MHz) δ 7.94 (4H, m), 7.37 (1H, s), 3.11 (6H, m).

4-[2-(Isopropyl-methyl-amino)-5-methyl-thiazol-4-yl]-benzoic acid

To a solution of 4-propionylbenzoic acid (11.2 mmol), benzyl alcohol (1.1 mL, 10.7 mmol) and dimethylaminopyridine (0.14 g, 1.1 mmol) in dichloromethane (90 ml) at 0° C. was added N-Ethyl-N'-(3-dimethylaminopropyl)carbodiimide×HCl (2.4 g, 12.3 mmol), then stirred at room temperature overnight. The obtained solution was then diluted with DCM, washed successively with aq. 10% citric acid and sq. sat sodium hydrogen carbonate, then dried ($Na_2SO_4$), filtered and concentrated in vacuo. Flash chromatography of the residue (silica gel, Petroleum ether-EtOAc) gave a colorless oil which crystallized upon standing (2.67 g). A portion of the benzyl ester from above (1 g, 3.73 mmol) was refluxed with 2-pyrrolidinone (0.37 g, 4.33 mmol) and pyrrolidone hydrotribromide (1.85 g, 3.73 mmol) in THF for 1.5 h. The resulting reaction mixture was allowed to reach room temperature, then diluted with EtOAc, washed successively with water, sq. 10% sodium thiosulphate, sq. sat. sodium hydrogen carbonate and brine, then dried ($Na_2SO_4$), filtered and concentrated in vacuo. The obtained bromide from above was directly mixed with isopropylthiocarboxamide (0.44 g, 3.73 mmol) in THF (20 mL) and refluxed overnight, then concentrated onto silica. Flash chromatography of the residue (silica gel, Petroleum ether-EtOAc-$Et_3N$) gave a light red oil (1.28 g, 3.49 mmol). To a stirred solution of the thiazole derivative (0.250 g, 0.68 mmol), obtained above, in acetonitrile (7 mL), acetic acid (1.3 mL) and sq. 37% formaldehyde (2 mL) at 0° C. was added sodium cyanoborohydride (0.09 g), then stirred at room temperature overnight. Additional sodium cyanoborohydride (0.08 g) was added, and after stirring for additional 2 h, the reaction mixture was diluted with water, neutralized using sq. 0.5 M sodium carbonate, then extracted with dichloromethane. The dichloromethane layers were collected, dried ($Na_2SO_4$), filtered and concentrated. Flash chromatography (silica gel, Petroleum ether-EtOAc) of the residue gave a slight yellow crystalline solid (0.115 g). 1H NMR ($CDCl_3$, 400 MHz,) δ 8.09 (2H, d), 7.72 (2H, d), 7.27-7.32 (5H, m), 5.38 (2H, s), 4.27 (1H, m), 2.92 (3H, s), 2.42 (3H, s), 1.22 (6H, d). The benzyl ester from above (0.25 g, 0.66 mmol) was hydrolysed by treating with sq. 1M LiOH (1.3 mL) in THF (2 mL) at 60° C. overnight. The obtained solution was then made slight acidic with sq. 10% citric acid and then extracted using dichloromethane. The organic layer was then dried ($Na_2SO_4$), filtered and concentrated. Column chromatography of the residue (Silica gel, dichloromethane-methanol) gave the title compound as a crystalline solid (0.19 g) m/z=304 in MS ES+, which was characterised by hplc and MS.

4-(2-Methylamino-thiazol-4-yl)-benzoic acid

To 25 ml of ethanol were added 4-(2-bromoacetyl)benzoic acid (486 mg, 2 mmole) and N-methyl thiourea (180 mg, 2 mmole). The reaction mixture was refluxed for 3 hr and the TLC showed the disappearing of the starting materials and the formation of a fluorescent product. The reaction was cooled on ice. The product was collected on filtration and washed with ethanol pre-cooled to 0° C. twice (2×3 ml), followed by diethyl ether. After drying, 486 mg product was obtained. 1H NMR (DMSO-$d_6$, 400 MHz) δ 7.97 (2H, d), 7.89 (2H, d), 7.32 (1H, s), 2.96 (3H, s).

4-[2-(4,4-Difluoro-piperidin-1-yl)-thiazol-4-yl]-benzoic acid 4,4-difluoropiperidine (hydrochloride salt, 1.57 g, 10 mmole) and diisopropylethylamine (1.74 ml, 10 mmole) in acetone (10 ml) was slowly dropped into a mixture of ethoxycarbonylisothiocyanate (1.02 ml, 10 mmole) in aceton (10 ml) at 0° C. When the addition was completed, the reaction was kept under stirring at room temperature for one hour. 3N hydrochloric acid (15 ml) was added and the reaction mixture was extracted with ethyl acetate. The organic phase was concentrated in vacuo.

To the residue was added concentrated hydrochloric acid (20 ml) and the reaction was kept at 80° C. for 5 hours. Water (30 ml) was added to the reaction. After the neutralization with ammonium carbonate, the reaction mixture was extracted with ethyl acetate. The organic phase was washed with water and dried in vacuo to obtain the crude intermediate 4,4-Difluoro-piperidine-1-carbothioic acid amide (1.21 g). To the residue from above (360 mg, 2 mmole) and 4-(2-bromoacetyl)benzoic acid (486 mg, 2 mmole) in THF (20 ml) were refluxed for 5 hours. TLC showed the disappearing of the starting materials and the formation of a fluorescent product. The reaction was cooled on ice. The solid was collected by filtration. The product was recrystallized from ethanol (380 mg). 1H NMR (DMSO-$d_6$, 400 MHz) δ 7.96 (4H, m), 7.51 (1 H, s), 3.66 (4H, m) 2.12 (4H, m).

Yields of the following title compounds in examples 8.53-8.55, 8.57 and 8.59-8.61 were in general between 30 and 90%.

4-(2-Isopropylamino-thiazol-4-yl)-benzoic acid

Isopropyl-thiourea (2.47 mmol) and 4-(2-Bromo-acetyl)-benzoic acid (2.47 mmol) were mixed in THF (12 mL). After stirring at room temperature for 5 minutes the mixture was heated to 80° C. for 2 hours. The volume was reduced to 5 mL and the mixture was then cooled to −20° C. and filtered. The solid was washed with a small amount of diethylether and dried. m/z=263.1 in MS ES+, which was characterized by hplc and MS and used in the next step without any further purification.

3-[2-(4-Methyl-piperazin-1-yl)-thiazol-4-yl]-benzoic acid

4-Methyl-piperazine-1-carbothioic acid amide (2.47 mmol) and 3-(2-Bromo-acetyl)-benzoic acid (2.47 mmol) were mixed in THF (12 mL). After stirring at room temperature for 5 minutes the mixture was heated to 80° C. for 2 hours. The mixture was then cooled to room temperature and filtered. The solid was washed with a small amount of diethylether and dried. m/z=304.1 in MS ES+, which was characterized by hplc and MS and used in the next step without any further purification.

3-(2-Isopropylamino-thiazol-4-yl)-benzoic acid

Isopropyl-thiourea (2.47 mmol) and 3-(2-Bromo-acetyl)-benzoic acid (2.47 mmol) were mixed in THF (12 mL). After stirring at room temperature for 5 minutes the mixture was heated to 80° C. for 2 hours. The volume was reduced to 5 mL and the mixture was then cooled to −20° C. and filtered. The solid was washed with a small amount of diethylether and dried. m/z=263.1 in MS ES+, which was characterized by hplc and MS and used in the next step without any further purification.

4-(2-Piperidin-4-yl-thiazol-4-yl)-benzoic acid

4-Thiocarbamoyl-piperidine-1-carboxylic acid tert-butyl ester (2.47 mmol) and 4-(2-Bromo-acetyl)-benzoic acid (2.47 mmol) were mixed in THF (12 mL). After stirring at room temperature for 5 minutes the mixture was heated to 80° C. for 2 hours. The volume was reduced to 5 mL and diethylether (5 mL) was added. The mixture was then cooled to −20° C. and filtered. The solid was washed with a small amount of diethylether and dried. m/z=289.1 in MS ES+, which was characterized by hplc and MS and used in the next step without any further purification.

4-[2-(1-Methyl-piperidin-4-yl)-thiazol-4-yl]-benzoic acid

To a solution of 4-(2-Piperidin-4-yl-thiazol-4-yl)-benzoic acid (1 mmol) in acetic acid (0.5 mL), methanol (3 mL) and tetrahydrofurane (4.5 mL) was added formaldehyde (aq. 37%, 300 mL) and polystyrene bound cyanoborohydride (2.36 mmol/g, 900 mg). The slurry was then agitated for 16 hours at room temperature. The slurry was then filtered and the resin washed with methanol (2 mL). The solution was concentrated to dryness in vacuo. m/z=303.1 in MS ES+, which was characterized by hplc and MS and used in the next step without any further purification.

4-[2-(Pyridin-3-ylamino)-thiazol-4-yl]-benzoic acid

Pyridin-3-yl-thiourea (2.06 mmol) and 4-(2-Bromo-acetyl)-benzoic acid (2.06 mmol) were mixed in THF (12 mL). After stirring at room temperature for 5 minutes the mixture was heated to 80° C. for 2 hours. The mixture was then cooled to room temperature and filtered. The solid was washed with a small amount of diethylether and dried. m/z=298.0 in MS ES+, which was characterized by hplc and MS and used in the next step without any further purification.

4-[2-(Pyridin-2-ylamino)-thiazol-4-yl]-benzoic acid

Pyridin-2-yl-thiourea (2.06 mmol) and 4-(2-Bromo-acetyl)-benzoic acid (2.06 mmol) were mixed in THF (12 mL). After stirring at room temperature for 5 minutes the mixture was heated to 80° C. for 2 hours. The mixture was then cooled to room temperature and filtered. The solid was washed with a small amount of diethylether and dried. m/z=298.0 in MS ES+, which was characterized by hplc and MS and used in the next step without any further purification.

4-(2-Cyclopentylamino-thiazol-4-yl)-benzoic acid

Isothiocyanato-cyclopentane (4 g) in ammonia (37% in water, 8 mL) and methanol (32 mL) was stirred for 16 hours, filtered of and dried. The Cyclopentyl-thiourea (2.06 mmol) and 4-(2-Bromo-acetyl)-benzoic acid (2.06 mmol) were mixed in THF (12 mL). After stirring at room temperature for 5 minutes the mixture was heated to 80° C. for 2 hours. The mixture was then cooled to room temperature and filtered. The solid was washed with a small amount of diethylether and dried. m/z=289.05 in MS ES+, which was characterized by hplc and MS and used in the next step without any further purification.

4-(2-Cyclopropylamino-thiazol-4-yl)-benzoic acid

Isothiocyanato-cyclopropane (4 g) was mixed with ammonia (37% in water, 8 mL) and methanol (32 mL) at 0° C. and then stirred for 16 hours at room temperature. The mixture was then cooled to 0° C., filtered, washed with a little water and dried. The Cyclopropyl-thiourea (2.06 mmol) and 4-(2-Bromo-acetyl)-benzoic acid (2.06 mmol) were mixed in THF (12 mL). After stirring at room temperature for 5 minutes the mixture was heated to 80° C. for 2 hours. The mixture was then cooled to room temperature and filtered. The solid was washed with a small amount of diethylether and dried. m/z=261.0 in MS ES+, which was characterized by hplc and MS and used in the next step without any further purification.

4-[2-(Cyclopropyl-methyl-amino)-thiazol-4-yl]-benzoic acid 4-(2-Cyclopropylamino-thiazol-4-yl)benzoic acid (1.98 mmol), methyliodide (4.36 mmol) and potassium carbonate were mixed in DMF (20 mL) and stirred for 72 hours at room temperature. The mixture was concentrated to dryness and partitioned between dichloromethane and water. The organic layer was dried (MgSO4) and concentrated to dryness. This solid was mixed with THF (4 mL), methanol (2 mL) and 1N LiOH (3 mmol) and heated to 50° C. for 1 hour. The mixture was then cooled to room temperature and 1N HCl was added until pH 4. The mixture was concentrated in vacuo, then the obtained residue was redissolved in dichloromethane-methanol and concentrated onto silica. Flash chromatography of the residue (silica gel, dichloromethane-methanol) gave the title compound as an off-white solid (0.1 g), m/z=275.0 in MS ES+, which was characterised by hplc and MS.

4-[2-(1-Methyl-pyrrolidin-3-yl)-thiazol-5-yl]-benzoic acid

3-Thiocarbamoyl-pyrrolidine-1-carboxylic acid tert-butyl ester (2.47 mmol) 4-(2-Bromo-acetyl)-benzoic acid (2.47 mmol) were mixed in THF (12 mL). After stirring at room temperature for 5 minutes the mixture was heated to 80° C. for 1 hour. The mixture was then cooled to room temperature and filtered. The solid was washed with a small amount of diethylether and dried. m/z=304.1 in MS ES+. This solid was then mixed in dichloromethane-trifluoroacetic acid (2:1) and kept at room temperature for 20 minutes. The mixture was concentrated to near dryness and the concentrated once from dichloromethane and once from 1 N HCl in diethylether. The remaining solid was mixed with acetic acid (0.5 mL), methanol (3 mL) and tetrahydrofurane (4.5 mL) and formaldehyde (aq. 37%, 300 mL) and polystyrene bound cyanoborohydride (2.36 mmol/g, 900 mg) was added. The slurry was then agitated for 16 hours at room temperature. The slurry was then filtered and the resin washed with methanol (2 mL). The solution was concentrated to dryness in vacuo. m/z=289.0 in MS ES+, which was characterized by hplc and MS and used in the next step without any further purification.

2-(1-methylpiperazine-4-yl)-6-(4-carboxyphen-1-yl)-pyridine hydrochloride 2,6-dibromopyridine (11.8 g, 50 mmol) was dissolved in dimethylformamide (50 ml) and 1-methylpiperazine (5.0 g, 50 mmol) and sodium iodide (0.6 g) was added. The solution was heated to 80° C. for 30 minutes, then allowed to reach room temperature and diluted with ethyl acetate and water. The water layer was carefully extracted and the organic layers were collected, dried ($Na_2SO_4$) and concentrated. Flash chromatography of the residue on silica-gel (packed with ethyl acetate) using ethyl acetate-methanol-triethylamine 20:2:1 as the eluant. Pure fractions were collected and concentrated. 1.54 g of the residue was dissolved in dimethoxymethane (48 ml) and tetrakistriphenylphosphine palladium(0) (5.0 g) was added. The solution was degassed and stirred for 15 minutes under N2. 4-ethoxycarbonylphenylboronic acid (1.16 g) was added followed by 36 ml aq. 1M sodium hydrogen carbonate solution. The solution was degassed one more time and heated to reflux and stirred for 12 hours. The solution was filtered and the filtercake was carefully extracted with ethyl acetate and dimethoxymethane. The extracts were evaporated and purified by flashchromathography on silica-gel (packed with ethyl acetate) using ethyl acetate-methanol-triethylamine 20:2:1 as the eluant. Pure fractions were collected and concentrated. The residue was dissolved in 30 ml concentrated hydrochloric acid and was refluxed for 12 hours. The solution was evaporated to yield the title compound as a solid. 1H-NMR (400 MHz, DMSO-$d_6$) δ 2.7 (3H, m) 3.3 (4H, m) 4.5 (4H, m) 7.0 (1H, m) 7.4 (1H, m) 7.8 (1H, m) 8.0 (1H, m) 8.15 (1H, m) 11.5 (1H, bs).

4-(6-Morpholin-4-yl-pyridin-2-yl)-benzoic acid hydrochloride 2,6-dibromopyridine (2.0 g) was dissolved in dimethoxymethane and morpholine (4.0 ml) and sodium iodide (0.3 g) was added. The solution was heated to reflux for 1 hour, then allowed to reach room temperature. The obtained solution was diluted with ethyl acetate, washed with water, then dried ($Na_2SO_4$), filtered and concentrated. Flash chromatography of the residue using stepwise gradient elution (ethyl acetate in hexane 20-33%). Pure fractions were concentrated and then subjected to Suzuki coupling as described in example 8.64, then purified by flash chromatography as described above. Pure fractions where collected and concentrated, then the residue was dissolved in 30 ml concentrated hydrochloric acid and was refluxed for 1 hour. The obtained solution was evaporated to yield the title compound as a solid. 1H-NMR (400 MHz, DMSO-$d_6$) δ 3.6 (4H, m) 3.7 (4H, m) 6.9 (1H, m) 7.3 (1H, m) 7.7 (1H,M) 7.9 (2H, m) 8.1 (2H, m).

Example 9

Fluid phase synthesis of N-[(1S)-1-((3aS,6S,6aS)-6-Fluoro-3-oxo-hexahydro-furo[3,2-b]pyrrole-4-carbonyl)-3-methyl-butyl]-4-[5-methyl-2-(4-methyl-piperazin-1-yl)-thiazol-4-yl]-benzamide

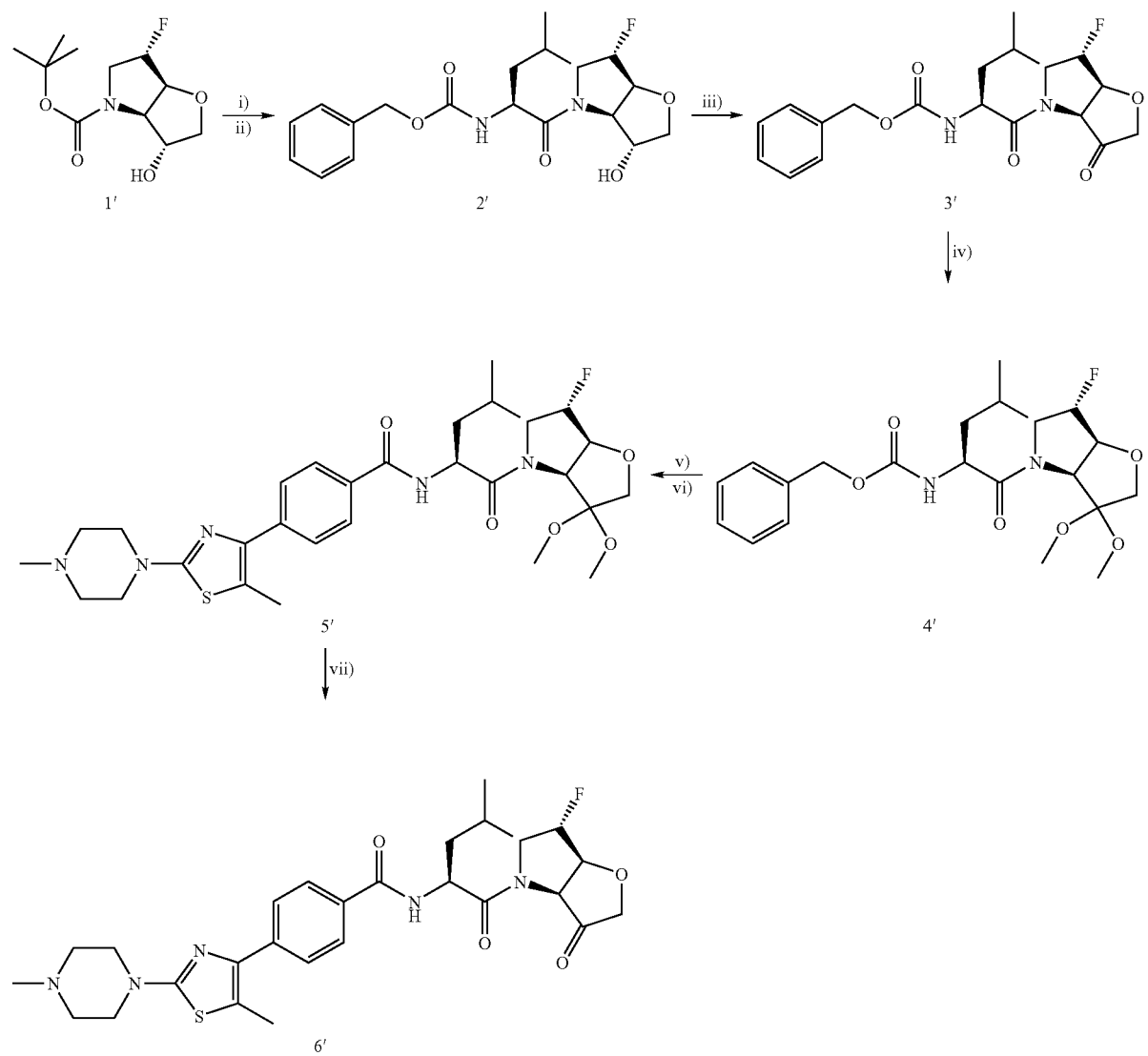

i) 4M HCl in dioxane ii) Cbz-Leu-OH, WSC, HOBt, DCM iii) Dess-Martin reagent, DCM
iv) 1,1,2-trimethoxyethane, p-TsOH, MeOH, 60 oC v) H2/Pd(C) vi) RCOOH, WSC, HOBt, DCM vii) TFA a) [(1S)-1-((3R,3aR,6S,6aS)-6-Fluoro-3-hydroxy-hexahydro-furo[3,2-b]pyrrole-4-carbonyl)-3-methyl-butyl]-carbamic acid benzyl ester (2')

(3R,3aR,6S,6aS)-6-Fluoro-3-hydroxy-hexahydro-furo[3,2-b]pyrrole-4-carboxylic acid tert-butyl ester (1') (20.24 mmol) was dissolved in 4M HCl in 1,4-dioxane, and stirred at room temperature for 1 h. The solvent was then removed under vacuum, and the residue was suspended in dichloromethane (50 ml), and treated with Cbz-Leu-OH (20.24 mmol), WSC HCl (22.26 mmol), HOBt (22.26 mmol) and NMM (40.48 mmol). The reaction mixture was stirred at room temperature overnight, then washed with saturated aqueous $NaHCO_3$, dried and concentrated. The residue was purified by column chromatography (ethyl acetate-hexanes 1:1, Rf 0.23) to afford compound 2 (15.62 mmol, 77%). MS(ES) m/z 395 (100%, [M+H]$^+$).

b) [(1S)-1-((3aS,6S,6aS)-6-Fluoro-3-oxo-hexahydro-furo[3,2-b]pyrrole-4-carbonyl)-3methyl-butyl]-carbamic acid benzyl ester (3')

A solution of compound 2' (15.61 mmol) in dichloromethane (70 ml) was treated with Dess-Martin periodinone (15.61 mmol), and the reaction mixture was stirred at room temperature overnight. The solution was then washed with saturated aqueous $NaHCO_3$, dried and concentrated, and the residue was purified by column chromatography (ethyl acetate-hexanes 1:1, Rf 0.37) to afford compound 3 (9.38 mmol, 60%). MS(ES) m/z 393 (15%, [M+H]$^+$), 411 (100%, [MH+H$_2$O]$^+$).

c) [(1S)-1-((3aS,6S,6aS)-6-Fluoro-3,3-dimethoxy-hexahydro-furo[3,2-b]pyrrole-4-carbonyl)-3-methyl-butyl]-carbamic acid benzyl ester (4')

A solution of compound 3' (8.49 mmol) in anhydrous methanol (50 ml) was treated with 1,1,2-trimethylorthoformate (24 ml) and p-TsOH (catalytic amount), and stirred at 60° C. for 3 h. The reaction mixture was then cooled down to room temperature, the solvent was removed under vacuum and the residue was purified by column chromatography to afford compound 4' (7.42 mmol, 87%). MS(ES) m/z 439 (100%, [M+H]$^+$).

d) N-[(1S)-1-((3aS,6S,6aS)-6-Fluoro-3,3-dimethoxy-hexahydro-furo[3,2-b]pyrrole-4-carbonyl)-3-methyl-butyl]-4-[5-methyl-2-(4-methyl-piperazin-1-yl)-thiazol-4-yl]-benzamide (5')

Compound 4' (0.625 mmol) was dissolved in ethanol (15 ml), and treated with a catalytic amount of Pd (10% wt Pd in carbon). The reaction was stirred under hydrogen atmosphere for 3-4 h. The reaction mixture was then filtered through a celite cake, and the cake was washed with ethanol, the organic extracts were combined and concentrated under vacuum. The residue was then dissolved in dichloromethane (15 ml) and treated with 4-[5-Methyl-2-(4-methyl-piperazin-1-yl)-thiazol-4-yl]-benzoic acid (0.60 mmol), WSC-HCl (0.625 mmol) and HOBt (0.625 mmol). The reaction mixture was monitored by HPLC. When the reaction had finished (4 h) the organic solution was washed with saturated aqueous $NaHCO_3$, dried and concentrated, and the residue was purified by preparative HPLC to afford compound 5 (0.30 mmol, 50%). MS(ES) m/z 604 (100% [M+H]$^+$).

e) N-[(1S)-1-((3aS,6S,6aS)-6-Fluoro-3-hexahydro-furo[3,2-b]pyrrole-4-carbonyl)-3-methyl-butyl]-4-[5methyl-2-(4-methyl-piperazin-1-yl)-thiazol-4-yl]-benzamide (6')

Compound 5' (0.21 mmol) was dissolved in neat trifluoroacetic acid (2 ml) and stirred at room temperature. The reaction was monitored closely by HPLC, to avoid cleaveage of the tertiary amide. As soon as the starting material disappeared (3 h 45 min) the TFA was removed under a stream of nitrogen, and the residue was partitioned between ethyl acetate and saturated aqueous $NaHCO_3$, the organic extracts were dried and concentrated under vacuum, and the residue was dissolved in acetonitrile-water 1:1 (2 ml) and freeze-dried overnight to afford compound 6' as a white solid (0.20 mmol, 94%). MS(ES) m/z 558 (10%, [M+H]$^+$), 576 (100%, [MH+H$_2$O]$^+$).

Biological Examples

Determination of Cathepsin K Proteolytic Catalytic Activity

Convenient assays for cathepsin K are carried out using human recombinant enzyme, such as that described in PDB.
ID BC016058 standard; mRNA; HUM; 1699 BP.
DE *Homo sapiens* cathepsin K (pycnodysostosis), mRNA (cDNA clone MGC:23107
RX MEDLINE;. RX PUBMED; 12477932.
DR RZPD; IRALp962G1234.
DR SWISS-PROT; P43235;

The recombinant cathepsin K can be expressed in a variety of commercially available expression systems including *E coli, Pichia* and *Baculovirus* systems. The purified enzyme is activated by removal of the prosequence by conventional methods.

Standard assay conditions for the determination of kinetic constants used a fluorogenic peptide substrate, typically H-D-Ala-Leu-Lys-AMC, and were determined in either 100 mM Mes/Tris, pH 7.0 containing 1 mM EDTA and 10 mM 2-mercaptoethanol or 100 mMNa phosphate, imM EDTA, 0.1% PEG4000 pH 6.5 or 100 mM Na acetate, pH 5.5 containing 5 mM EDTA and 20 mM cysteine, in each case optionally with 1M DTT as stabiliser. The enzyme concentration used was 5 nM. The stock substrate solution was prepared at 10 mM in DMSO. Screens were carried out at a fixed substrate concentration of 60 μM and detailed kinetic studies with doubling dilutions of substrate from 250 μM. The total DMSO concentration in the assay was kept below 3%. All assays were conducted at ambient temperature. Product fluorescence (excitation at 390 nm, emission at 460 nm) was monitored with a Labsystems Fluoroskan Ascent fluorescent plate reader. Product progress curves were generated over 15 minutes following generation of AMC product.

Inhibition Studies

Potential inhibitors are screened using the above assay with variable concentrations of test compound. Reactions were initiated by addition of enzyme to buffered solutions of substrate and inhibitor. $K_i$ values were calculated according to equation 1

$$v_0 = \frac{VS}{K_M\left(1+\frac{I}{K_i}\right)+S} \quad (1)$$

where $v_0$ is the velocity of the reaction, V is the maximal velocity, S is the concentration of substrate with Michaelis constant of $K_M$, and I is the concentration of inhibitor.

Compounds of the invention bearing the distinctive halogen substituent in the P1 group were assayed against the closest individualised compound of the abovementioned WO 02057270:

| Compound | Cathepsin K $K^1$ nM |
|---|---|
| 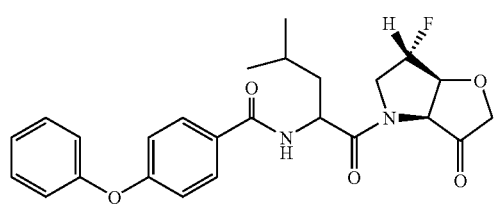 Prior art: Example 10 of WO 02057270 | 66* |
| Invention Example 6 | 5.3 |

It will be apparent that introduction of at least one halogen atom to P1, according to the invention has surprisingly resulted in an increase in potency.

*Note that the Ki indicated in WO 02057270 for the prior art compound is the less potent 0.1 micromolar, whereas the above trials reflect accurate side by side trials in the same assay system.

Abbreviations

| | | | |
|---|---|---|---|
| DMF | dimethylformamide | DCM | dichloromethane |
| TBDMS | tert-butyldimethylsilyl | RT | room temperature |
| THF | tetrahydrofuran | Ac | acetyl |
| TLC | thin layer chromatography | DMAP | dimethylaminopyridine |
| EtOAc | ethyl acetate | | |

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:
1. A compound of the formula II

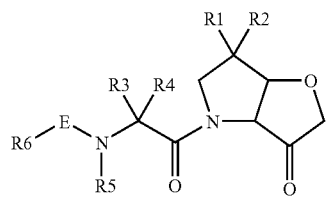

wherein
one of $R^1$ and $R^2$ is halo and the other is H or halo;
$R^3$ is $C_1$-$C_5$ straight or branched chain, optionally fluorinated, alkyl;
$R^4$ is H; or
$R^3$ together with $R^4$ defines
a spiro-$C_5$-$C_7$ cycloalkyl, optionally substituted with 1 to 3 substituents selected from halo, hydroxyl, $C_1$-$C_4$ alkyl or $C_1$-$C_4$ haloalkyl; or optionally bridged with a methylene group; or
a $C_4$-$C_6$ saturated heterocycle having a hetero atom selected from
O, NRa, S, S(=O)$_2$;
$R^5$ is independently selected from H or methyl;
E is —C(=O)—, —S(=O)$_m$—, —NR$^5$S(=O)$_m$—, —NR$^5$C(=O)—, —OC(=O)—,
$R^6$ is a stable, optionally substituted, monocyclic or bicyclic carbocycle or heterocycle wherein the or each ring has 4, 5 or 6 ring atoms and 0 to 3 hetero atoms selected from S, O and N and wherein the optional substituents comprise 1 to 3 members selected from $R^7$;
$R^7$ is independently selected from halo, oxo, nitrile, nitro, $C_1$-$C_4$ alkyl, —X—NRbR$^9$, —NRb—X'—R$^9$, NH$_2$CO—, —X—R$^9$, —X—O—R$^9$, —O—X'—R$^9$, —X—C(=O)R$^9$, —X—(C=O)NRaR$^9$, —X—NRbC(=O)R$^9$, —X—NHSO$_m$R$^9$, —X—S(=O)$_m$R$^9$, —X—C(=O)OR$^9$, —X—NRbC(=O)OR$^9$;
$R^9$ is independently H, $C_1$-$C_4$ alkyl, $C_3$-$C_6$ cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, phenyl, any of which is optionally substituted with $R^{10}$;
$R^{10}$ is independently selected from hydroxy, —X—R$^{9'}$, —X—NRbR$^{9'}$, —NRb—X'—R$^{9'}$, nitro, cyano, carboxy, oxo, $C_1$-$C_4$-alkoxy, $C_1$-$C_4$ alkanoyl, carbamoyl;
$R^{9'}$ is independently H, $C_1$-$C_4$ alkyl, $C_3$-$C_6$ cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, phenyl, any of which is optionally substituted with $R^{10'}$;
$R^{10'}$ is independently selected from hydroxy, nitro, cyano, carboxy, oxo, $C_1$-$C_4$ alkyl, $C_1$-$C_4$-alkoxy, $C_1$-$C_4$ alkanoyl, carbamoyl; or, where $R^6$ is a monocyclic group substituted directly or via methylene by an aryl or a 5 or 6 membered hetereoaryl moiety substituted by $R^{9'}$ which is a morpholinyl, piperidinyl or piperazinyl group, then $R^{10'}$ can additionally be fluoro, difluoro, or $C_1$-$C_3$alkyloxy$C_1$-$C_3$alkyl-; or, where $R^6$ is phenyl substituted by thiazol-4-yl, 5-methylthiazol-4-yl or thien-2-yl, any of which is substituted by morpholinylmethyl-, piperidinylmethyl-, piperazinylmethyl-, then $R^{10'}$ may additionally be fluoro, difluoro or $C_1$-$C_3$ alkyl-O—$C_1$-$C_3$alkyl-;

X is independently a bond or $C_1$-$C_4$ alkylenyl;

X' is independently $C_1$-$C_4$ alkylenyl;

Ra is independently H, $C_1$-$C_4$ alkyl or $CH_3C(=O)$;

Rb is independently H, or $C_1$-$C_4$ alkyl m is independently 0, 1 or 2;

or a pharmaceutically acceptable salt thereof.

2. A compound according to claim 1, wherein the stereochemistry is as depicted in the partial structure below:

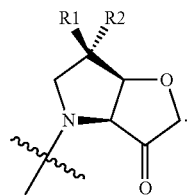

3. A compound compound according to claim 1, wherein the stereochemistry is as depicted in the partial structure below:

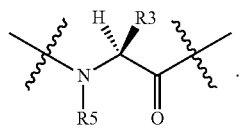

4. A compound according to claim 1, wherein $R^2$ is halo and $R^1$ is H.

5. A compound according to claim 4, wherein $R^2$ is fluoro.

6. A compound according to claim 1, wherein $R^1$ and $R^2$ are fluoro.

7. A compound according to claim 1, wherein $R^3$ is $C_1$-$C_4$ branched chain alkyl.

8. A compound according to claim 7, wherein $R^3$ is isobutyl.

9. A compound according to claim 1, wherein $R^3$ and $R^4$ together define spirocycloalkyl.

10. A compound according to claim 9, wherein $R^3$ and $R^4$ together define spirocyclohexyl.

11. A compound according to claim 1, wherein $R^5$ is H.

12. A compound according to claim 1, wherein E is —C(=O)—.

13. A compound according to claim 1, wherein $R^6$ is substituted phenyl.

14. A compound according to claim 13, wherein the substituent comprises —NRaRb, —CH$_2$NRaRb, —NRbR$^9$, —NRbC$_1$-C$_4$alkylR$^9$, $C_1$-$C_4$ straight or branched alkyl or —O—R$^9$.

15. A compound according to claim 14, wherein the substituent comprises —NH—CH$_2$-phenyl, —NHCH$_2$pyridyl or —NH-phenyl, wherein each phenyl or pyridyl ring is substituted with $C_1$-$C_4$-alkyl, —NRaRb, —NRbR$^9$ or —NRbC$_1$-C$_4$alkylR$^9$.

16. A compound according to claim 13, wherein the substituent comprises $C_3$-$C_6$ cycloalkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, phenyl, any of which is optionally substituted with $R^{10}$.

17. A compound according to claim 16, wherein the substituent is selected from indolinyl, pyranyl, thiopyranyl, pyrrolyl, oxazolyl, isoxazolyl, thiazolyl, imidazolyl, pyridinyl, pyrimidinyl, pyrazinyl, indolyl, any of which is optionally substituted with $R^{10}$.

18. A compound according to claim 17, wherein the substituent is thiazolyl, 5-methyl-thiazolyl or thienyl, optionally substituted with $R^{10}$.

19. A compound according to claim 18, wherein the substituent is thiazol-4-yl, 5-methylthiazol-4-yl or thien-2-yl, optionally substituted with $R^{10}$.

20. A compound according to claim 18, wherein the thiazolyl, 5-methylthiazolyl or theinyl is substituted with morpholinyl, morpholinylmethyl-, piperidinyl, piperidinylmethyl-, piperazinyl, piperazinylmethyl, any of which is substituted with $C_1$-$C_3$ alkyl, fluoro, difluoro or $C_1$-$C_3$ alkyl-O—$C_1$-$C_3$alkyl-.

21. A compound according to claim 20, wherein the substituent to the thiazolyl, 5-methylthiazolyl or thienyl is piperid-4-yl which is substituted with methyl, piperazinyl which is N-substituted with $C_1$-$C_3$ alkyl or methyloxyethyl-, -or piperid-1-ylmethyl-which is unsubstituted or 4-substituted with fluoro or di-fluoro.

22. A compound according to claim 13, wherein the substituent comprises a morpholine, piperidine or piperazine ring, optionally substituted with $R^{10}$.

23. A compound according to claim 22 comprising piperid-4-yl or N-piperazinyl, N-substituted with Ra or piperidin-1-yl which is 4-substituted with —NRaRb.

24. A compound according to claim 1, wherein $R^6$ is optionally substituted: benzothiazol or benzofuryl or benzoxazolyl.

25. A compound according to claim 24, wherein the substituent is –OR$^9$, —O—X'—R$^9$, —NRbR$^9$ or —NRb—X'—R$^9$.

26. A compound according to claim 25, wherein $R^9$ is piperid-4-yl, piperazin-1-yl or piperidin-1-yl or morpholino, any of which is substituted with $C_1$-$C_3$ alkyl.

27. A compound according to claim 26, wherein the optional substituent to $R^6$ is N-morpholinylethyloxy, N-methylpiperid-4-yloxy, or N-methylmorpholin-3-ylmethyloxy.

28. A pharmaceutical composition comprising a compound as defined in claim 1 and a pharmaceutically acceptable carrier or diluents therefor.

29. A compound according to claim 1 which is:

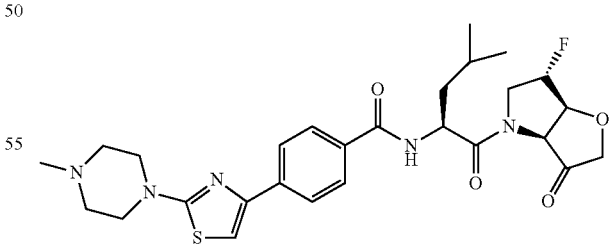

or a pharmaceutically acceptable salt thereof.

* * * * *